US011299531B2

(12) United States Patent
Zen et al.

(10) Patent No.: US 11,299,531 B2
(45) Date of Patent: Apr. 12, 2022

(54) FUSION PROTEIN COMPRISING A LIGAND BINDING DOMAIN OF VEGF AND PDGF

(71) Applicants: Allgenesis Biotherapeutics Inc., Taipei (TW); AP Biosciences, Inc., Taipei (TW)

(72) Inventors: Kevin Zen, Del Mar, CA (US); Pei-Tzu Wu, Taipei (TW); Jeng-Horng Her, Taipei (TW); Huang-Tsu Chen, Taipei (TW); Jiun-Shyang Leou, Taipei (TW); Ching-Hsuan Hsu, Taipei (TW)

(73) Assignees: Allgenesis Biotherapeutics Inc., Taipei (TW); AP Biosciences Inc., Taipei (TW)

( * ) Notice: Subject to any disclaimer, the term of this patent is extended or adjusted under 35 U.S.C. 154(b) by 428 days.

(21) Appl. No.: 15/542,692

(22) PCT Filed: Mar. 10, 2016

(86) PCT No.: PCT/US2016/021762
§ 371 (c)(1),
(2) Date: Jul. 11, 2017

(87) PCT Pub. No.: WO2016/145189
PCT Pub. Date: Sep. 15, 2016

(65) Prior Publication Data
US 2017/0369552 A1    Dec. 28, 2017

Related U.S. Application Data

(60) Provisional application No. 62/131,261, filed on Mar. 11, 2015.

(51) Int. Cl.
C07K 14/705    (2006.01)
C07K 14/71     (2006.01)
A61K 38/00     (2006.01)

(52) U.S. Cl.
CPC .............. *C07K 14/71* (2013.01); *A61K 38/00* (2013.01); *C07K 2319/30* (2013.01); *C07K 2319/70* (2013.01)

(58) Field of Classification Search
None
See application file for complete search history.

(56) References Cited

U.S. PATENT DOCUMENTS

2006/0234347 A1    10/2006    Harding et al.

FOREIGN PATENT DOCUMENTS

| CN | 102311502 A   | 1/2012  |
| WO | 2014160507 A1 | 10/2014 |
| WO | 2015109898 A1 | 7/2015  |

OTHER PUBLICATIONS

Int'l Search Report and Written Opinion dated Aug. 24, 2016 in Int'l Application No. PCT/US2016/021762.
Kudelka et al, "Emergence of Dual VEGF and PDGF Antagonists in the Treatment of Exudative Age-Related Macular Degeneration," Expert Review in Ophthalmology, vol. 8, No. 5, pp. 475-484 (2013).
Chakrabarti et al, "Current Protein-based Anti-angiogenic Therapeutics," Mini Reviews in Medicinal Chemistry, vol. 14, No. 3, pp. 291-312 (2014).
Zhang et al, "Ocular neovascularization: Implication of endogenous angiogenic inhibitors and potential therapy," Progress in Retinal and Eye Research, vol. 26, pp. 1-37 (2007).
Sullivan et al, "The VEGF family in cancer and antibody-based strategies for their inhibition," mAbs, vol. 2, Iss. 2, pp. 165-175 (2010).
Ueno et al, "Inhibition of PDGF ß Receptor Signal Transduction by Coexpression of a Truncated Receptor," Science, vol. 252, pp. 844-848 (1991).
Martin et al., "Ranibizumab and Bevacizumab for Treatment of Neovascular Age-Related Macular Degeneration: 2-Year Results: Comparison of Age-related Macular Degeneration Treatments Trials CATT) Research Group," Ophthalmology, vol. 119, No. 7, pp. 1388-1398 (2012).
Patel, "Combination Therapy for Age-Related Macular Degeneration," Retina, The Journal Of Retinal And Vitreous Diseases, vol. 29, No. 6, pp. S45-S48 (2009).
Reinmuth et al, "Induction of VEGF in perivascular cells defines a potential paracrine mechanism for endothelial cell survival," The FASEB Journal, vol. 15, No. 7, pp. 1239-1241 (2001) (published online, 19 pages).
Jo et al, "Inhibition of Platelet-Derived Growth Factor B Signaling Enhances the Efficacy of Anti-Vascular Endothelial Growth Factor Therapy in Multiple Models of Ocular Neovascularization," American Journal of Pathology, vol. 168, No. 6, pp. 2036-2053 (2006).
Leppänen et al, "Predimerization of Recombinant Platelet-Derived Growth Factor Receptor Extracellular Domains Increases Antagonistic Potency," Biochemistry, vol. 39, No. 9, pp. 2370-2375 (2000).
Lokker et al, "Functional Importance of Platelet-derived Growth Factor (PDGF) Receptor Extracellular immunoglobulin-like Domains," The Journal of Biological Chemistry, vol. 272, No. 52, pp. 33037-33044 (1997).
Heidaran et al, "ß PDGFR-IgG chimera demonstrates that human ß PDGFR Ig-like domains 1 to 3 are sufficient for high affinity PDGF BB binding," The FASEB Journal, vol. 9, No. 1, pp. 140-145 (1995).

(Continued)

*Primary Examiner* — Michael D Pak
(74) *Attorney, Agent, or Firm* — Ice Miller LLP

(57) ABSTRACT

Fusion proteins containing a PDGF binding portion, a VEGF binding portion, and an Fc antibody region are described. Also described are nucleic acids encoding the fusion proteins, compositions comprising the fusion proteins, and methods of using the fusion proteins for treating or preventing clinical conditions characterized by abnormal angiogenesis, such as vascular permeability, edema or inflammation.

18 Claims, 11 Drawing Sheets
Specification includes a Sequence Listing.

(56) References Cited

OTHER PUBLICATIONS

Dugel, "Anti-PDGF Combination Therapy in Neovascular Age-related Macular Degeneration: Results of a Phase 2b Study," Retina Today, pp. 65-71 (Mar. 2013).
Daniel et al, "Risk of Scar in the Comparison of Age-related Macular Degeneration Treatments Trials," Ophthalmology, vol. 121, No. 3, pp. 656-666 (2014).
Duan et al, "A Functional Soluble Extracellular Region of the Platelet-derived Growth Factor (PDGF) ß-Receptor Antagonizes PDGF-stimulated Responses," The Journal of Biological Chemistry, vol. 266, No. 1, pp. 413-418 (1991).
Bloch et al, "Subfoveal Fibrosis in Eyes With Neovascular Age-Related Macular Degeneration Treated With Intravitreal Ranibizumab," American Journal of Opthalmology, vol. 156, No. 1, pp. 116-124 (2013).
Bhisitkul, "Vascular endothelial growth factor biology: clinical implications for ocular treatments," British Journal of Ophthalmology, vol. 90, pp. 1542-1547 (2006).
Benjamin et al, "A plasticity window for blood vessel remodelling is defined by pericyte coverage of the preformed endothelial network and is regulated by PDGF-B and VEGF," Development, vol. 125, pp. 1591-1598 (1998).
Andrae et al, "Role of platelet-derived growth factors in physiology and medicine," Genes & Development, vol. 22, pp. 1276-1312 (2008).

SEQUENCE LISTING

<160> NUMBER OF SEQ ID NOS: 50

<210> SEQ ID NO 1
<211> LENGTH: 897

```
<212> TYPE: DNA
<213> ORGANISM: Homo sapiens

<400> SEQUENCE: 1
cagggcctgg tcgtcacacc cccggggcca gagcttgtcc tcaatgtctc cagcaccttc      60
gttctgacct gctcgggttc agctccggtg gtgtgggaac ggatgtccca ggagccccca     120
caggaaatgg ccaaggccca ggatggcacc ttctccagcg tgctcacact gaccaacctc     180
actgggctag acacgggaga atactttgc acccacaatg actcccgtgg actggagacc      240
gatgagcgga aacggctcta catctttgtg ccagatccca ccgtgggctt cctccctaat     300
gatgccgagg aactattcat ctttctcacg gaaataactg agatcaccat tccatgccga     360
gtaacagacc cacagctggt ggtgacactg cacgagaaga aggggacgt tgcactgcct      420 gtcccctatg atcaccaacg tggcttttt ggtatctttg aggacagaag ctacatctgc      480
aaaaccacca ttggggacag ggaggtggat tctgatgcct actatgtcta cagactccag     540
gtgtcatcca tcaacgtctc tgtgaacgca gtgcagactg tggtccgcca gggtgagaac     600
atcaccctca tgtgcattgt gatcgggaat gaggtggtca acttcgagtg gacatacccc     660
cgcaaagaaa gtgggcggct ggtggagccg gtgactgact tcctcttgga tatgccttac     720
cacatccgct ccatcctgca catccccagt gccgagttag aagactcggg gacctacacc     780
tgcaatgtga cggagagtgt gaatgaccat caggatgaaa aggccatcaa catcaccgtg     840
gttgagagcg gctacgtgcg gctcctggga gaggtgggca cactacaatt tgctgag       897

<210> SEQ ID NO 2
<211> LENGTH: 299
<212> TYPE: PRT
<213> ORGANISM: Homo sapiens

<400> SEQUENCE: 2

Gln Gly Leu Val Val Thr Pro Pro Gly Pro Glu Leu Val Leu Asn Val
 1               5                  10                  15

Ser Ser Thr Phe Val Leu Thr Cys Ser Gly Ser Ala Pro Val Val Trp
            20                  25                  30

Glu Arg Met Ser Gln Glu Pro Pro Gln Glu Met Ala Lys Ala Gln Asp
        35                  40                  45

Gly Thr Phe Ser Ser Val Leu Thr Leu Thr Asn Leu Thr Gly Leu Asp
    50                  55                  60

Thr Gly Glu Tyr Phe Cys Thr His Asn Asp Ser Arg Gly Leu Glu Thr
65                  70                  75                  80

Asp Glu Arg Lys Arg Leu Tyr Ile Phe Val Pro Asp Pro Thr Val Gly
                85                  90                  95

Phe Leu Pro Asn Asp Ala Glu Glu Leu Phe Ile Phe Leu Thr Glu Ile
            100                 105                 110

Thr Glu Ile Thr Ile Pro Cys Arg Val Thr Asp Pro Gln Leu Val Val
        115                 120                 125

Thr Leu His Glu Lys Lys Gly Asp Val Ala Leu Pro Val Pro Tyr Asp
    130                 135                 140

His Gln Arg Gly Phe Phe Gly Ile Phe Glu Asp Arg Ser Tyr Ile Cys
145                 150                 155                 160

Lys Thr Thr Ile Gly Asp Arg Glu Val Asp Ser Asp Ala Tyr Tyr Val
                165                 170                 175

Tyr Arg Leu Gln Val Ser Ser Ile Asn Val Ser Val Asn Ala Val Gln
            180                 185                 190
```

Thr Val Val Arg Gln Gly Glu Asn Ile Thr Leu Met Cys Ile Val Ile
            195                 200                 205

Gly Asn Glu Val Val Asn Phe Glu Trp Thr Tyr Pro Arg Lys Glu Ser
    210                 215                 220

Gly Arg Leu Val Glu Pro Val Thr Asp Phe Leu Leu Asp Met Pro Tyr
225                 230                 235                 240

His Ile Arg Ser Ile Leu His Ile Pro Ser Ala Glu Leu Glu Asp Ser
                245                 250                 255

Gly Thr Tyr Thr Cys Asn Val Thr Glu Ser Val Asn Asp His Gln Asp
            260                 265                 270

Glu Lys Ala Ile Asn Ile Thr Val Val Glu Ser Gly Tyr Val Arg Leu
        275                 280                 285

Leu Gly Glu Val Gly Thr Leu Gln Phe Ala Glu
        290                 295

<210> SEQ ID NO 3
<211> LENGTH: 891
<212> TYPE: DNA
<213> ORGANISM: Artificial Sequence
<220> FEATURE:
<223> OTHER INFORMATION: Coding sequence for modified PID

<400> SEQUENCE: 3
ctggtcgtga cacctcccgg acccgagctg gtgctcaacg tctcctccac ctttgtgctg      60
acatgcagcg gcagcgctcc tgtggtctgg aacggatgt cccaggagcc tccccaggaa     120
atggccaagg cccaggacgg caccttttcc agcgtcctca cactcaccaa cctgacaggc     180
ctggacaccg gcgagtactt tgcacccac aatgactcca ggggactgga aaccgatgag     240
cggaagcggc tctacatttt cgtccccgac cccaccgtcg gatttctgcc taatgacgct     300
gaagagctgt ttatcttcct gacagagatc accgaaatca ccatcccctg tcgggtcacc     360
gatccccagc tggtggtcac actgcacgag aagaagggag atgtcgccct gcctgtgcct     420
tatgaccatc agaggggctt ttccggcatt ttcgaggaca ggagctacat ctgcaaaacc     480
accatcggag accgggaggt cgacagcgat gcctattacg tctaccggct ccaggtctcc     540
tccatcaatg tgagcgtgaa tgctgtccag acagtggtcc ggcagggcga aatatcaca      600 ctgatgtgca ttgtcattgg caacgaggtg gtcaacttcg agtggaccta tcctaggaag     660
gagagcggcc ggctcgtcga acctgtgacc gacttcctcc tggacatgcc ttaccacatt     720
cggtccatcc tgcacattcc tagcgccgag ctggaggaca gcggaaccta cacctgcaac     780
gtgaccgagt ccgtgaatga ccaccaggat gagaaggcca tcaacatcac agtcgtggag     840
agcggatacg tcaggctgct cggagaagtc ggcacactgc agttcgccga g              891

<210> SEQ ID NO 4
<211> LENGTH: 891
<212> TYPE: DNA
<213> ORGANISM: Artificial Sequence
<220> FEATURE:
<223> OTHER INFORMATION: Coding sequence for modified PID

<400> SEQUENCE: 4
ctggtcgtca cacccccggg gccagagctt gtcctcaatg tctccagcac cttcgttctg      60
acctgctcgg gttcagctcc ggtggtgtgg aacggatgt cccaggagcc cccacaggaa     120
atggccaagg cccaggatgg caccttctcc agcgtgctca cactgaccaa cctcactggg     180
ctagacacgg gagaatactt tgcacccac aatgactccc gtggactgga gaccgatgag     240

```
cggaaacggc tctacatctt tgtgccagat cccaccgtgg gcttcctccc taatgatgcc    300
gaggaactat tcatctttct cacggaaata actgagatca ccattccatg ccgagtaaca    360
gacccacagc tggtggtgac actgcacgag aagaaagggg acgttgcact gcctgtcccc    420
tatgatcacc aacgtggctt ttccggtatc tttgaggaca gaagctacat ctgcaaaacc    480
accattgggg acagggaggt ggattctgat gcctactatg tctacagact ccaggtgtca    540
tccatcaacg tctctgtgaa cgcagtgcag actgtggtcc gccagggtga gaacatcacc    600
ctcatgtgca ttgtgatcgg gaatgaggtg gtcaacttcg agtggacata ccccgcaaa    660 gaaagtgggc ggctggtgga gccggtgact gacttcctct tggatatgcc ttaccacatc    720
cgctccatcc tgcacatccc cagtgccgag ttagaagact cggggaccta cacctgcaat    780
gtgacggaga gtgtgaatga ccatcaggat gaaaaggcca tcaacatcac cgtggttgag    840
agcggctacg tgcggctcct gggagaggtg ggcacactac aatttgctga g              891
```

```
<210> SEQ ID NO 5
<211> LENGTH: 297
<212> TYPE: PRT
<213> ORGANISM: Artificial Sequence
<220> FEATURE:
<223> OTHER INFORMATION: Modified PID sequence

<400> SEQUENCE: 5

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255
```

```
Tyr Thr Cys Asn Val Thr Glu Ser Val Asn Asp His Gln Asp Glu Lys
            260                 265                 270

Ala Ile Asn Ile Thr Val Val Glu Ser Gly Tyr Val Arg Leu Leu Gly
        275                 280                 285

Glu Val Gly Thr Leu Gln Phe Ala Glu
        290                 295

<210> SEQ ID NO 6
<211> LENGTH: 612
<212> TYPE: DNA
<213> ORGANISM: Artificial Sequence
<220> FEATURE:
<223> OTHER INFORMATION: Coding sequence for VID

<400> SEQUENCE: 6
gacactggta gacctttgt tgaaatgtat tctgaaattc ctgaaattat tcatatgact      60
gaaggaagag aacttgttat tccttgtaga gttacttctc ctaatattac tgttactctt    120
aagaagtttc ctcttgatac tcttattcct gatggaaaga gaattatttg ggattctaga    180
aagggattta ttatttctaa tgctacttat aaggaaattg gacttcttac ttgtgaagct    240
actgttaatg gacatcttta taagactaat tatcttactc atagacaaac taataccatc    300
atcgacgtgg ttctgagtcc gtctcatgga attgaactat ctgttggaga aaagcttgtc    360
ttaaattgta cagcaagaac tgaactaaat gtggggatta cttcaactg ggaatacccct    420 tcttcgaagc atcagcataa gaaacttgta aaccgagacc taaaaccca gtctgggagt    480 gagatgaaga aattcttgag caccctgact atagatggtg taacccggag tgaccaagga    540
ttgtacacct gtgcagcatc cagtgggctg atgaccaaga gaacagcac atttgtcagg    600 gtccatgaaa aa                                                       612

<210> SEQ ID NO 7
<211> LENGTH: 204
<212> TYPE: PRT
<213> ORGANISM: Artificial Sequence
<220> FEATURE:
<223> OTHER INFORMATION: VID sequence

<400> SEQUENCE: 7

Asp Thr Gly Arg Pro Phe Val Glu Met Tyr Ser Glu Ile Pro Glu Ile
1               5                  10                  15

Ile His Met Thr Glu Gly Arg Glu Leu Val Ile Pro Cys Arg Val Thr
            20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
    50                  55                  60

Ile Ser Asn Ala Thr Tyr Lys Glu Ile Gly Leu Leu Thr Cys Glu Ala
65                  70                  75                  80

Thr Val Asn Gly His Leu Tyr Lys Thr Asn Tyr Leu Thr His Arg Gln
                85                  90                  95

Thr Asn Thr Ile Ile Asp Val Val Leu Ser Pro Ser His Gly Ile Glu
            100                 105                 110

Leu Ser Val Gly Glu Lys Leu Val Leu Asn Cys Thr Ala Arg Thr Glu
        115                 120                 125

Leu Asn Val Gly Ile Asp Phe Asn Trp Glu Tyr Pro Ser Ser Lys His
    130                 135                 140
```

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
            180                 185                 190

Lys Lys Asn Ser Thr Phe Val Arg Val His Glu Lys
            195                 200

<210> SEQ ID NO 8
<211> LENGTH: 609
<212> TYPE: DNA
<213> ORGANISM: Artificial Sequence
<220> FEATURE:
<223> OTHER INFORMATION: Coding sequence for modified VID

<400> SEQUENCE: 8

```
ggaaggccct tcgtggagat gtacagcgag attcctgaga ttatccacat gaccgaggga      60
cgggaactgg tgattccctg ccgggtcacc agccccaaca tcaccgtgac cctcaagaag     120
ttcccccctgg acaccctgat ccctgacggc aaaaggatta tctgggacag ccggaagggc     180
tttatcatca gcaatgccac atacaaggag attggactcc tgacctgcga ggctacagtc     240
aacggacacc tgtacaagac caactacctg acccaccggc agaccaatac catcatcgac     300
gtggtgctga gccccagcca cggaattgag ctgagcgtgg agaaaaaact cgtgctcaac     360
tgcacagccc ggaccgaact caatgtcgga atcgacttca ctgggaata ccccagctcc     420
aagcaccagc acaagaagct ggtcaaccgg gatctcaaga cccagtccgg cagcgaaatg     480
aagaagttcc tcagcaccct gaccatcgat ggcgtcacaa ggagcgatca gggactctac     540
acctgcgccg ctagctccgg actcatgacc aagaagaact ccacatttgt ccgggtgcac     600
gaaaagtga                                                            609
```

<210> SEQ ID NO 9
<211> LENGTH: 606
<212> TYPE: DNA
<213> ORGANISM: Artificial Sequence
<220> FEATURE:
<223> OTHER INFORMATION: Coding sequence for modified VID

<400> SEQUENCE: 9

```
ggtagacctt tgttgaaat gtattctgaa attcctgaaa ttattcatat gactgaagga       60
agagaacttg ttattccttg tagagttact tctcctaata ttactgttac tcttaagaag    120
tttcctcttg atactcttat tcctgatgga aagagaatta tttgggattc tagaaaggga    180
tttattattt ctaatgctac ttataaggaa attggacttc ttacttgtga agctactgtt    240
aatggacatc tttataagac taattatctt actcatagac aaactaatac catcatcgac    300
gtggttctga gtccgtctca tggaattgaa ctatctgttg agaaaagct tgtcttaaat     360
tgtacagcaa gaactgaact aaatgtgggg attgacttca ctgggaata cccttcttcg    420
aagcatcagc ataagaaact tgtaaccga gacctaaaaa cccagtctgg gagtgagatg     480
aagaaattct tgagcaccct gactatagat ggtgtaaccc ggagtgacca aggattgtac    540
acctgtgcag catccagtgg gctgatgacc aagaagaaca gcacatttgt cagggtccat    600
gaaaaa                                                               606
```

<210> SEQ ID NO 10
<211> LENGTH: 202

<212> TYPE: PRT
<213> ORGANISM: Artificial Sequence
<220> FEATURE:
<223> OTHER INFORMATION: Modified VID sequence

<400> SEQUENCE: 10

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys
        195                 200
```

<210> SEQ ID NO 11
<211> LENGTH: 681
<212> TYPE: DNA
<213> ORGANISM: Homo sapiens

<400> SEQUENCE: 11

```
gacaaaactc acacatgtcc accgtgtcca gcacctgaac tcctgggtgg accgtcagtc     60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaagagc    660
ctctccctgt ctccgggtaa a                                              681
```

<210> SEQ ID NO 12
<211> LENGTH: 227
<212> TYPE: PRT
<213> ORGANISM: Homo sapiens

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 13
<211> LENGTH: 678
<212> TYPE: DNA
<213> ORGANISM: Artificial Sequence
<220> FEATURE:
<223> OTHER INFORMATION: Coding sequence for Fc sequence of Fusion
    Protein 6

<400> SEQUENCE: 13
gataagaccc acacctgtcc tccttgtcct gctcctgagc tcctcggcgg acctagcgtg      60
ttcctgtttc ccctaagcc taaagacacc ctcatgatca gccggacccc cgaggtcaca     120
tgcgtggtgg tcgacgtctc ccatgaggat cccgaggtga agttcaattg gtacgtcgac     180
ggcgtcgagg tccacaatgc caaaaccaaa ccccgggagg agcagtacaa cagcacctat     240
agggtggtca gcgtcctgac cgtgctgcac caagactggc tgaacggcaa ggagtacaaa     300
tgcaaagtca gcaataaggc cctccccgcc cccattgaga agaccatctc caaggctaag     360
ggccaaccta gggagcccca ggtgtacacc ctgcctccca gccgggatga gctgacaaag     420
aaccaggtga gcctcacctg tctggtgaag ggcttttacc cctccgatat tgccgtggag     480

```
tgggaaagca acggacagcc tgagaacaac tacaagacaa ccccccctgt cctggacagc      540
gatggctcct tcttcctgta cagcaagctg acagtggata gagccggtg gcagcaggga      600 aacgtcttta gctgcagcgt gatgcatgag gccctgcaca atcactacac ccagaagtcc      660
ctgtccctga gccctggc                                                    678
```

<210> SEQ ID NO 14
<211> LENGTH: 678
<212> TYPE: DNA
<213> ORGANISM: Artificial Sequence
<220> FEATURE:
<223> OTHER INFORMATION: Coding sequence for Fc sequence of Fusion
      Protein 4

<400> SEQUENCE: 14

```
gacaaaactc acacatgtcc accgtgtcca gcacctgaac tcctgggtgg accgtcagtc       60
ttcctcttcc cccaaaaacc caaggacacc ctcatgatct cccggacccc tgaggtcaca      120
tgcgtggtgg tggacgtgag ccacgaagac cctgaggtca agttcaactg gtacgtggac      180
ggcgtggagg tgcataatgc caagacaaag ccgcgggagg agcagtacaa cagcacgtac      240
cgtgtggtca gcgtcctcac cgtcctgcac caggactggc tgaatggcaa ggagtacaag      300
tgcaaggtct ccaacaaagc cctcccagcc cccatcgaga aaaccatctc caaagccaaa      360
gggcagcccc gagaaccaca ggtgtacacc ctgcccccat cccgggatga gctgaccaag      420
aaccaggtca gcctgacctg cctggtcaaa ggcttctatc cagcgacat cgccgtggag      480 tgggagagca atgggcagcc ggagaacaac tacaagacca cgcctcccgt gctggactcc      540
gacggctcct tcttcctcta cagcaagctc accgtggaca agagcaggtg gcagcagggg      600
aacgtcttct catgctccgt gatgcatgag gctctgcaca accactacac gcagaagagc      660
ctctccctgt ctccgggt                                                    678
```

<210> SEQ ID NO 15
<211> LENGTH: 226
<212> TYPE: PRT
<213> ORGANISM: Artificial Sequence
<220> FEATURE:
<223> OTHER INFORMATION: Modified Fc sequence of fusion proteins

<400> SEQUENCE: 15

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 16
<211> LENGTH: 6
<212> TYPE: DNA
<213> ORGANISM: Artificial Sequence
<220> FEATURE:
<223> OTHER INFORMATION: Coding sequence of a linker sequence

<400> SEQUENCE: 16 gccagc                                                              6

<210> SEQ ID NO 17
<211> LENGTH: 6
<212> TYPE: DNA
<213> ORGANISM: Artificial Sequence
<220> FEATURE:
<223> OTHER INFORMATION: Coding sequence of a linker sequence

<400> SEQUENCE: 17 gctagc                                                              6

<210> SEQ ID NO 18
<211> LENGTH: 2
<212> TYPE: PRT
<213> ORGANISM: Artificial Sequence
<220> FEATURE:
<223> OTHER INFORMATION: linker sequence

<400> SEQUENCE: 18

Ala Ser
1

<210> SEQ ID NO 19
<211> LENGTH: 18
<212> TYPE: DNA
<213> ORGANISM: Artificial Sequence
<220> FEATURE:
<223> OTHER INFORMATION: Coding sequence of a linker sequence

<400> SEQUENCE: 19
ggaggaggcg gtggatct                                                18

<210> SEQ ID NO 20
<211> LENGTH: 6
<212> TYPE: PRT
<213> ORGANISM: Artificial Sequence
<220> FEATURE:
<223> OTHER INFORMATION: linker sequence

<400> SEQUENCE: 20

Gly Gly Gly Gly Gly Ser

-continued

<210> SEQ ID NO 21
<211> LENGTH: 6
<212> TYPE: DNA
<213> ORGANISM: Artificial Sequence
<220> FEATURE:
<223> OTHER INFORMATION: Coding sequence of a linker sequence

<400> SEQUENCE: 21 ggaggc                                                                    6

<210> SEQ ID NO 22
<211> LENGTH: 2
<212> TYPE: PRT
<213> ORGANISM: Artificial Sequence
<220> FEATURE:
<223> OTHER INFORMATION: linker sequence

<400> SEQUENCE: 22

Gly Gly
1

<210> SEQ ID NO 23
<211> LENGTH: 45
<212> TYPE: DNA
<213> ORGANISM: Artificial Sequence
<220> FEATURE:
<223> OTHER INFORMATION: Coding sequence of a linker sequence

<400> SEQUENCE: 23
ggcggcggcg gcagcggcgg aggcggatcc ggcggaggcg gctcc              45

<210> SEQ ID NO 24
<211> LENGTH: 15
<212> TYPE: PRT
<213> ORGANISM: Artificial Sequence
<220> FEATURE:
<223> OTHER INFORMATION: linker sequence

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 9
<212> TYPE: DNA
<213> ORGANISM: Artificial Sequence
<220> FEATURE:
<223> OTHER INFORMATION: Coding sequence of a linker sequence

<400> SEQUENCE: 25 ggagacacc                                                                 9

<210> SEQ ID NO 26
<211> LENGTH: 3
<212> TYPE: PRT
<213> ORGANISM: Artificial Sequence
<220> FEATURE:
<223> OTHER INFORMATION: linker sequence

<400> SEQUENCE: 26

Gly Asp Thr
1

<210> SEQ ID NO 27

```
<211> LENGTH: 6
<212> TYPE: DNA
<213> ORGANISM: Artificial Sequence
<220> FEATURE:
<223> OTHER INFORMATION: Coding sequence of a linker sequence

<400> SEQUENCE: 27 ggtgga                                                                    6

<210> SEQ ID NO 28
<211> LENGTH: 2
<212> TYPE: PRT
<213> ORGANISM: Artificial Sequence
<220> FEATURE:
<223> OTHER INFORMATION: linker sequence

<400> SEQUENCE: 28

Gly Gly
1

<210> SEQ ID NO 29
<211> LENGTH: 45
<212> TYPE: DNA
<213> ORGANISM: Artificial Sequence
<220> FEATURE:
<223> OTHER INFORMATION: Coding sequence of a linker sequence

<400> SEQUENCE: 29
ggaggcggtg gatctggtgg cggtggaagc ggaggtggag gttcc             45

<210> SEQ ID NO 30
<211> LENGTH: 15
<212> TYPE: PRT
<213> ORGANISM: Artificial Sequence
<220> FEATURE:
<223> OTHER INFORMATION: linker sequence

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 9
<212> TYPE: DNA
<213> ORGANISM: Artificial Sequence
<220> FEATURE:
<223> OTHER INFORMATION: Coding sequence of a linker sequence

<400> SEQUENCE: 31 ggagacact                                                                 9

<210> SEQ ID NO 32
<211> LENGTH: 3
<212> TYPE: PRT
<213> ORGANISM: Artificial Sequence
<220> FEATURE:
<223> OTHER INFORMATION: linker sequence

<400> SEQUENCE: 32

Gly Asp Thr
1

<210> SEQ ID NO 33
<211> LENGTH: 60
<212> TYPE: DNA
<213> ORGANISM: Artificial Sequence
<220> FEATURE:
```

<223> OTHER INFORMATION: Coding sequence of a signal peptide sequence

<400> SEQUENCE: 33
atggagacag acacactcct gctatgggta ctgcttcttt gggttcccgg atccactggc    60

<210> SEQ ID NO 34
<211> LENGTH: 20
<212> TYPE: PRT
<213> ORGANISM: Artificial Sequence
<220> FEATURE:
<223> OTHER INFORMATION: Signal peptide sequence

<400> SEQUENCE: 34

Met Glu Thr Asp Thr Leu Leu Leu Trp Val Leu Leu Leu Trp Val Pro
1               5                   10                  15

Gly Ser Thr Gly
            20

<210> SEQ ID NO 35
<211> LENGTH: 57
<212> TYPE: DNA
<213> ORGANISM: Artificial Sequence
<220> FEATURE:
<223> OTHER INFORMATION: Coding sequence of a signal peptide sequence

<400> SEQUENCE: 35
atggagtttg gcctgtcctg gctcttcctc gtggctatcc tgaagggcgt gcagtgt    57

<210> SEQ ID NO 36
<211> LENGTH: 19
<212> TYPE: PRT
<213> ORGANISM: Artificial Sequence
<220> FEATURE:
<223> OTHER INFORMATION: Signal peptide sequence

<400> SEQUENCE: 36

Met Glu Phe Gly Leu Ser Trp Leu Phe Leu Val Ala Ile Leu Lys Gly
1               5                   10                  15

Val Gln Cys

<210> SEQ ID NO 37
<211> LENGTH: 2217
<212> TYPE: DNA
<213> ORGANISM: Artificial Sequence
<220> FEATURE:
<223> OTHER INFORMATION: Coding sequence of Fusion Protein 1 sequence

<400> SEQUENCE: 37
gacactggaa gacctttgt tgaaatgtat tctgaaattc ctgaaattat tcatatgact    60
gaaggaagag aacttgttat tccttgtaga gttacttctc ctaatattac tgttactctt   120
aagaagtttc ctcttgatac tcttattcct gatggaaaga gaattatttg ggattctaga   180
aagggattta tatttctaa tgctactat aaggaaattg acttcttac ttgtgaagct   240
actgttaatg gacatctta taagactaat tatcttactc atagacaaac taataccatc   300
atcgacgtgg ttctgagtcc gtctcatgga attgaactat ctgttggaga aaagcttgtc   360
ttaaattgta cagcaagaac tgaactaaat gtggggattg acttcaactg gaatacccct   420
tcttcgaagc atcagcataa gaaacttgta aaccgagacc taaaaacccca gtctgggagt   480
gagatgaaga aattcttgag caccctgact atagatggtg taacccggag tgaccaagga   540
ttgtacacct gtgcagcatc cagtgggctg atgaccaaga gaacagcac atttgtcagg   600

| | |
|---|---|
| gtccatgaaa aagacaaaac tcacacatgt ccaccgtgtc cagcacctga actcctgggt | 660 |
| ggaccgtcag tcttcctctt ccccccaaaa cccaaggaca ccctcatgat ctcccggacc | 720 |
| cctgaggtca catgcgtggt ggtggacgtg agccacgaag accctgaggt caagttcaac | 780 |
| tggtacgtgg acggcgtgga ggtgcataat gccaagacaa agccgcggga ggagcagtac | 840 |
| aacagcacgt accgtgtggt cagcgtcctc accgtcctgc accaggactg gctgaatggc | 900 |
| aaggagtaca agtgcaaggt ctccaacaaa gccctcccag cccccatcga gaaaaccatc | 960 |
| tccaaagcca aagggcagcc ccgagaacca caggtgtaca ccctgccccc atcccgggat | 1020 |
| gagctgacca agaaccaggt cagcctgacc tgcctggtca aaggcttcta tcccagcgac | 1080 |
| atcgccgtgg agtgggagag caatgggcag ccggagaaca actacaagac cacgcctccc | 1140 |
| gtgctggact ccgacggctc cttcttcctc tacagcaagc tcaccgtgga caagagcagg | 1200 |
| tggcagcagg ggaacgtctt ctcatgctcc gtgatgcatg aggctctgca caaccactac | 1260 |
| acgcagaaga gcctctccct gtctccgggt aaaggtggag gaggcggtgg atccggatct | 1320 |
| cagggcctgg tcgtcacacc cccggggcca gagcttgtcc tcaatgtctc cagcaccttc | 1380 |
| gttctgacct gctcgggttc agctccggtg gtgtgggaac ggatgtccca ggagccccca | 1440 |
| caggaaatgg ccaaggccca ggatggcacc ttctccagcg tgctcacact gaccaacctc | 1500 |
| actgggctag acacgggaga atacttttgc acccacaatg actcccgtgg actggagacc | 1560 |
| gatgagcgga acggctctca catctttgtg ccagatccca ccgtgggctt cctccctaat | 1620 |
| gatgccgagg aactattcat ctttctcacg gaaataactg agatcaccat tccatgccga | 1680 |
| gtaacagacc cacagctggt ggtgacactg acgagaagaa aagggacgt tgcactgcct | 1740 |
| gtcccctatg atcaccaacg tggcttttttt ggtatctttg aggacagaag ctacatctgc | 1800 |
| aaaaccacca ttggggacag ggaggtggat tctgatgcct actatgtcta cagactccag | 1860 |
| gtgtcatcca tcaacgtctc tgtgaacgca gtgcagactg tggtccgcca gggtgagaac | 1920 |
| atcaccctca tgtgcattgt gatcgggaat gaggtggtca acttcgagtg gacataccec | 1980 |
| cgcaaagaaa gtgggcggct ggtggagccg gtgactgact tcctcttgga tatgccttac | 2040 |
| cacatccgct ccatcctgca catccccagt gccgagttag aagactcggg gacctacacc | 2100 |
| tgcaatgtga cggagagtgt gaatgaccat caggatgaaa aggccatcaa catcaccgtg | 2160 |
| gttgagagcg gctacgtgcg gctcctggga gaggtgggca cactacaatt tgctgag | 2217 |

<210> SEQ ID NO 38
<211> LENGTH: 739
<212> TYPE: PRT
<213> ORGANISM: Artificial Sequence
<220> FEATURE:
<223> OTHER INFORMATION: Fusion Protein 1 sequence

<400> SEQUENCE: 38

```
Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
            20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
    50                  55                  60

Ile Ser Asn Ala Thr Tyr Lys Glu Ile Gly Leu Leu Thr Cys Glu Ala
65                  70                  75                  80
```

-continued

```
Thr Val Asn Gly His Leu Tyr Lys Thr Asn Tyr Leu Thr His Arg Gln
                 85                  90                  95

Thr Asn Thr Ile Ile Asp Val Val Leu Ser Pro Ser His Gly Ile Glu
            100                 105                 110

Leu Ser Val Gly Glu Lys Leu Val Leu Asn Cys Thr Ala Arg Thr Glu
            115                 120                 125

Leu Asn Val Gly Ile Asp Phe Asn Trp Glu Tyr Pro Ser Ser Lys His
            130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
            180                 185                 190

Lys Lys Asn Ser Thr Phe Val Arg Val His Glu Lys Asp Lys Thr His
            195                 200                 205

Thr Cys Pro Pro Cys Pro Ala Pro Glu Leu Leu Gly Gly Pro Ser Val
        210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys
            260                 265                 270

Thr Lys Pro Arg Glu Glu Gln Tyr Asn Ser Thr Tyr Arg Val Val Ser
            275                 280                 285

Val Leu Thr Val Leu His Gln Asp Trp Leu Asn Gly Lys Glu Tyr Lys
            290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Asp Glu Leu Thr Lys Asn Gln Val Ser Leu Thr Cys Leu
            340                 345                 350

Val Lys Gly Phe Tyr Pro Ser Asp Ile Ala Val Glu Trp Glu Ser Asn
            355                 360                 365

Gly Gln Pro Glu Asn Asn Tyr Lys Thr Thr Pro Pro Val Leu Asp Ser
        370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys Gly
            420                 425                 430

Gly Gly Gly Gly Ser Gly Ser Gln Gly Leu Val Val Thr Pro Pro
            435                 440                 445

Gly Pro Glu Leu Val Leu Asn Val Ser Ser Thr Phe Val Leu Thr Cys
        450                 455                 460

Ser Gly Ser Ala Pro Val Val Trp Glu Arg Met Ser Gln Glu Pro Pro
465                 470                 475                 480

Gln Glu Met Ala Lys Ala Gln Asp Gly Thr Phe Ser Ser Val Leu Thr
                485                 490                 495

Leu Thr Asn Leu Thr Gly Leu Asp Thr Gly Glu Tyr Phe Cys Thr His
```

```
                    500                 505                 510
Asn Asp Ser Arg Gly Leu Glu Thr Asp Glu Arg Lys Arg Leu Tyr Ile
            515                 520                 525

Phe Val Pro Asp Pro Thr Val Gly Phe Leu Pro Asn Asp Ala Glu Glu
        530                 535                 540

Leu Phe Ile Phe Leu Thr Glu Ile Thr Glu Ile Thr Ile Pro Cys Arg
545                 550                 555                 560

Val Thr Asp Pro Gln Leu Val Val Thr Leu His Glu Lys Lys Gly Asp
                565                 570                 575

Val Ala Leu Pro Val Pro Tyr Asp His Gln Arg Gly Phe Phe Gly Ile
            580                 585                 590

Phe Glu Asp Arg Ser Tyr Ile Cys Lys Thr Thr Ile Gly Asp Arg Glu
        595                 600                 605

Val Asp Ser Asp Ala Tyr Tyr Val Tyr Arg Leu Gln Val Ser Ser Ile
    610                 615                 620

Asn Val Ser Val Asn Ala Val Gln Thr Val Val Arg Gln Gly Glu Asn
625                 630                 635                 640

Ile Thr Leu Met Cys Ile Val Ile Gly Asn Glu Val Val Asn Phe Glu
                645                 650                 655

Trp Thr Tyr Pro Arg Lys Glu Ser Gly Arg Leu Val Glu Pro Val Thr
            660                 665                 670

Asp Phe Leu Leu Asp Met Pro Tyr His Ile Arg Ser Ile Leu His Ile
        675                 680                 685

Pro Ser Ala Glu Leu Glu Asp Ser Gly Thr Tyr Thr Cys Asn Val Thr
    690                 695                 700

Glu Ser Val Asn Asp His Gln Asp Glu Lys Ala Ile Asn Ile Thr Val
705                 710                 715                 720

Val Glu Ser Gly Tyr Val Arg Leu Leu Gly Val Gly Thr Leu Gln
                725                 730                 735

Phe Ala Glu

<210> SEQ ID NO 39
<211> LENGTH: 2250
<212> TYPE: DNA
<213> ORGANISM: Artificial Sequence
<220> FEATURE:
<223> OTHER INFORMATION: Coding sequence of Fusion Protein 2 sequence

<400> SEQUENCE: 39
cagggcctgg tcgtcacacc cccggggcca gagcttgtcc tcaatgtctc cagcaccttc      60
gttctgacct gctcgggttc agctccggtg gtgtgggaac ggatgtccca ggagccccca     120
caggaaatgg ccaaggccca ggatggcacc ttctccagcg tgctcacact gaccaacctc     180
actgggctag acacgggaga atactttgc acccacaatg actcccgtgg actggagacc     240
gatgagcgga acggctcta catctttgtg ccagatccca ccgtgggctt cctccctaat     300
gatgccgagg aactattcat ctttctcacg gaaataactg agatcaccat tccatgccga     360
gtaacagacc cacagctggt ggtgacactg cacgagaaga aggggacgt tgcactgcct     420 gtcccctatg atcaccaacg tggcttttt ggtatcttg aggacagaag ctacatctgc     480
aaaaccacca ttgggacag ggaggtggat tctgatgcct actatgtcta cagactccag     540
gtgtcatcca tcaacgtctc tgtgaacgca gtgcagactg tggtccgcca gggtgagaac     600
atcaccctca tgtgcattgt gatcgggaat gaggtggtca acttcgagtg acatacccc     660 cgcaaagaaa gtgggcggct ggtggagccg gtgactgact cctcttggga tatgccttac     720
```

```
cacatccgct ccatcctgca catccccagt gccgagttag aagactcggg gacctacacc    780
tgcaatgtga cggagagtgt gaatgaccat caggatgaaa aggccatcaa catcaccgtg    840
gttgagagcg gctacgtgcg gctcctggga gaggtgggca cactacaatt tgctgaggct    900
agcgacaaaa ctcacacatg tccaccgtgt ccagcacctg aactcctggg tggaccgtca    960
gtcttcctct ccccccaaa acccaaggac accctcatga tctcccggac ccctgaggtc   1020
acatgcgtgg tggtggacgt gagccacgaa gaccctgagg tcaagttcaa ctggtacgtg   1080
gacggcgtgg aggtgcataa tgccaagaca aagccgcggg aggagcagta caacagcacg   1140
taccgtgtgg tcagcgtcct caccgtcctg caccaggact ggctgaatgg caaggagtac   1200
aagtgcaagg tctccaacaa agccctccca gcccccatcg agaaaaccat ctccaaagcc   1260
aaagggcagc cccgagaacc acaggtgtac accctgcccc catcccggga tgagctgacc   1320
aagaaccagg tcagcctgac ctgcctggtc aaaggcttct atcccagcga catcgccgtg   1380
gagtgggaga gcaatgggca gccggagaac aactacaaga ccacgcctcc cgtgctggac   1440
tccgacggct ccttcttcct ctacagcaag ctcaccgtgg acaagagcag gtggcagcag   1500
gggaacgtct tctcatgctc cgtgatgcat gaggctctgc acaaccacta cacgcagaag   1560
agcctctccc tgtctccggg taaaggtgga ggaggcggtg gatctggtgg cggtggaagc   1620
ggaggtggag gttccggaga cactggtaga cctttttgttg aaatgtattc tgaaattcct   1680
gaaattattc atatgactga aggaagagaa cttgttattc cttgtagagt tacttctcct   1740
aatattactg ttactcttaa gaagtttcct cttgatactc ttattcctga tggaaagaga   1800
attatttggg attctagaaa gggatttatt atttctaatg ctacttataa ggaaattgga   1860
cttcttactt gtgaagctac tgttaatgga catctttata agactaatta tcttactcat   1920
agacaaacta ataccatcat cgacgtggtt ctgagtccgt ctcatggaat tgaactatct   1980
gttggagaaa agcttgtctt aaattgtaca gcaagaactg aactaaatgt ggggattgac   2040
ttcaactggg aataccttc ttcgaagcat cagcataaga aacttgtaaa ccgagaccta   2100
aaaacccagt ctgggagtga gatgaagaaa ttcttgagca ccctgactat agatggtgta   2160
acccggagtg accaaggatt gtacacctgt gcagcatcca gtgggctgat gaccaagaag   2220
aacagcacat ttgtcagggt ccatgaaaaa                                   2250
```

<210> SEQ ID NO 40
<211> LENGTH: 750
<212> TYPE: PRT
<213> ORGANISM: Artificial Sequence
<220> FEATURE:
<223> OTHER INFORMATION: Fusion Protein 2 sequence

<400> SEQUENCE: 40

Gln Gly Leu Val Val Thr Pro Pro Gly Pro Glu Leu Val Leu Asn Val
1               5                   10                  15

Ser Ser Thr Phe Val Leu Thr Cys Ser Gly Ser Ala Pro Val Val Trp
            20                  25                  30

Glu Arg Met Ser Gln Glu Pro Pro Gln Glu Met Ala Lys Ala Gln Asp
        35                  40                  45

Gly Thr Phe Ser Ser Val Leu Thr Leu Thr Asn Leu Thr Gly Leu Asp
    50                  55                  60

Thr Gly Glu Tyr Phe Cys Thr His Asn Asp Ser Arg Gly Leu Glu Thr
65                  70                  75                  80

Asp Glu Arg Lys Arg Leu Tyr Ile Phe Val Pro Asp Pro Thr Val Gly

-continued

```
                        85                  90                  95
Phe Leu Pro Asn Asp Ala Glu Glu Leu Phe Ile Phe Leu Thr Glu Ile
                    100                 105                 110

Thr Glu Ile Thr Ile Pro Cys Arg Val Thr Asp Pro Gln Leu Val Val
            115                 120                 125

Thr Leu His Glu Lys Lys Gly Asp Val Ala Leu Pro Val Pro Tyr Asp
        130                 135                 140

His Gln Arg Gly Phe Phe Gly Ile Phe Glu Asp Arg Ser Tyr Ile Cys
145                 150                 155                 160

Lys Thr Thr Ile Gly Asp Arg Glu Val Asp Ser Asp Ala Tyr Tyr Val
                165                 170                 175

Tyr Arg Leu Gln Val Ser Ser Ile Asn Val Ser Val Asn Ala Val Gln
                180                 185                 190

Thr Val Val Arg Gln Gly Glu Asn Ile Thr Leu Met Cys Ile Val Ile
            195                 200                 205

Gly Asn Glu Val Val Asn Phe Glu Trp Thr Tyr Pro Arg Lys Glu Ser
        210                 215                 220

Gly Arg Leu Val Glu Pro Val Thr Asp Phe Leu Leu Asp Met Pro Tyr
225                 230                 235                 240

His Ile Arg Ser Ile Leu His Ile Pro Ser Ala Glu Leu Glu Asp Ser
                245                 250                 255

Gly Thr Tyr Thr Cys Asn Val Thr Glu Ser Val Asn Asp His Gln Asp
                260                 265                 270

Glu Lys Ala Ile Asn Ile Thr Val Val Glu Ser Gly Tyr Val Arg Leu
            275                 280                 285

Leu Gly Glu Val Gly Thr Leu Gln Phe Ala Glu Ala Ser Asp Lys Thr
        290                 295                 300

His Thr Cys Pro Pro Cys Pro Ala Pro Glu Leu Leu Gly Gly Pro Ser
305                 310                 315                 320

Val Phe Leu Phe Pro Pro Lys Pro Lys Asp Thr Leu Met Ile Ser Arg
                325                 330                 335

Thr Pro Glu Val Thr Cys Val Val Val Asp Val Ser His Glu Asp Pro
            340                 345                 350

Glu Val Lys Phe Asn Trp Tyr Val Asp Gly Val Glu Val His Asn Ala
        355                 360                 365

Lys Thr Lys Pro Arg Glu Glu Gln Tyr Asn Ser Thr Tyr Arg Val Val
        370                 375                 380

Ser Val Leu Thr Val Leu His Gln Asp Trp Leu Asn Gly Lys Glu Tyr
385                 390                 395                 400

Lys Cys Lys Val Ser Asn Lys Ala Leu Pro Ala Pro Ile Glu Lys Thr
                405                 410                 415

Ile Ser Lys Ala Lys Gly Gln Pro Arg Glu Pro Gln Val Tyr Thr Leu
            420                 425                 430

Pro Pro Ser Arg Asp Glu Leu Thr Lys Asn Gln Val Ser Leu Thr Cys
        435                 440                 445

Leu Val Lys Gly Phe Tyr Pro Ser Asp Ile Ala Val Glu Trp Glu Ser
    450                 455                 460

Asn Gly Gln Pro Glu Asn Asn Tyr Lys Thr Thr Pro Pro Val Leu Asp
465                 470                 475                 480

Ser Asp Gly Ser Phe Phe Leu Tyr Ser Lys Leu Thr Val Asp Lys Ser
                485                 490                 495

Arg Trp Gln Gln Gly Asn Val Phe Ser Cys Ser Val Met His Glu Ala
            500                 505                 510
```

Leu His Asn His Tyr Thr Gln Lys Ser Leu Ser Leu Ser Pro Gly Lys
            515                 520                 525

Gly Gly Gly Gly Gly Ser Gly Gly Gly Gly Ser Gly Gly Gly Gly
530                 535                 540

Ser Gly Asp Thr Gly Arg Pro Phe Val Glu Met Tyr Ser Glu Ile Pro
545                 550                 555                 560

Glu Ile Ile His Met Thr Glu Gly Arg Glu Leu Val Ile Pro Cys Arg
                565                 570                 575

Val Thr Ser Pro Asn Ile Thr Val Thr Leu Lys Lys Phe Pro Leu Asp
            580                 585                 590

Thr Leu Ile Pro Asp Gly Lys Arg Ile Ile Trp Asp Ser Arg Lys Gly
        595                 600                 605

Phe Ile Ile Ser Asn Ala Thr Tyr Lys Glu Ile Gly Leu Leu Thr Cys
    610                 615                 620

Glu Ala Thr Val Asn Gly His Leu Tyr Lys Thr Asn Tyr Leu Thr His
625                 630                 635                 640

Arg Gln Thr Asn Thr Ile Ile Asp Val Val Leu Ser Pro Ser His Gly
                645                 650                 655

Ile Glu Leu Ser Val Gly Glu Lys Leu Val Leu Asn Cys Thr Ala Arg
            660                 665                 670

Thr Glu Leu Asn Val Gly Ile Asp Phe Asn Trp Glu Tyr Pro Ser Ser
        675                 680                 685

Lys His Gln His Lys Lys Leu Val Asn Arg Asp Leu Lys Thr Gln Ser
    690                 695                 700

Gly Ser Glu Met Lys Lys Phe Leu Ser Thr Leu Thr Ile Asp Gly Val
705                 710                 715                 720

Thr Arg Ser Asp Gln Gly Leu Tyr Thr Cys Ala Ala Ser Ser Gly Leu
                725                 730                 735

Met Thr Lys Lys Asn Ser Thr Phe Val Arg Val His Glu Lys
            740                 745                 750

<210> SEQ ID NO 41
<211> LENGTH: 2301
<212> TYPE: DNA
<213> ORGANISM: Artificial Sequence
<220> FEATURE:
<223> OTHER INFORMATION: Coding sequence of Fusion Protein 6 sequence

<400> SEQUENCE: 41 atggagtttg␣␣cctgtcctg␣gctcttcctc␣gtggctatcc␣tgaagggcgt␣gcagtgtctg␣␣␣␣␣60 gtcgtgacac␣ctcccggacc␣cgagctggtg␣ctcaacgtct␣cctccacctt␣gtgctgaca␣␣␣120 tgcagcggca␣cgctcctgt␣ggtctgggaa␣cggatgtccc␣aggagcctcc␣ccaggaaatg␣␣␣180 gccaaggccc␣aggacggcac␣cttttccagc␣gtcctcacac␣tcaccaacct␣gacaggcctg␣␣␣240 gacaccggcg␣agtactttg␣cacccacaat␣gactccaggg␣gactggaaac␣cgatgagcgg␣␣␣300 aagcggctct␣acattttcgt␣ccccgacccc␣accgtcggat␣ttctgcctaa␣tgacgctgaa␣␣␣360 gagctgttta␣tcttcctgac␣agagatcacc␣gaaatcacca␣tcccctgtcg␣ggtcaccgat␣␣␣420 ccccagctgg␣tggtcacact␣gcacgagaag␣aagggagatg␣tcgccctgcc␣tgtgccttat␣␣␣480 gaccatcaga␣ggggctttc␣cggcattttc␣gaggacagga␣gctacatctg␣caaaaccacc␣␣␣540 atcggagacc␣gggaggtcga␣cagcgatgcc␣tattacgtct␣accggctcca␣ggtctcctcc␣␣␣600 atcaatgtga␣gcgtgaatgc␣tgtccagaca␣gtggtccggc␣agggcgagaa␣atcacactg␣␣␣␣660 atgtgcattg␣tcattggcaa␣cgaggtggtc␣aacttcgagt␣ggacctatcc␣taggaaggag␣␣␣720

```
agcggccggc tcgtcgaacc tgtgaccgac ttcctcctgg acatgcctta ccacattcgg    780
tccatcctgc acattcctag cgccgagctg gaggacagcg aacctacac ctgcaacgtg     840 accgagtccg tgaatgacca ccaggatgag aaggccatca acatcacagt cgtggagagc    900
ggatacgtca ggctgctcgg agaagtcggc acactgcagt tcgccgaggc cagcgataag    960
acccacacct gtcctccttg tcctgctcct gagctcctcg gcggacctag cgtgttcctg   1020 tttccccta agcctaaaga cacctcatg atcagccgga ccccgaggt cacatgcgtg      1080 gtggtcgacg tctcccatga ggatcccgag gtgaagttca attggtacgt cgacggcgtc   1140
gaggtccaca atgccaaaac caaacccgg gaggagcagt acaacagcac ctataggtg     1200 gtcagcgtcc tgaccgtgct gcaccaagac tggctgaacg gcaaggagta caaatgcaaa   1260
gtcagcaata aggccctccc cgcccccatt gagaagacca tctccaaggc taagggccaa   1320
cctagggagc cccaggtgta caccctgcct cccagccggg atgagctgac aaagaaccag   1380
gtgagcctca cctgtctggt gaagggcttt taccctccg atattgccgt ggagtgggaa    1440
agcaacggac agcctgagaa caactacaag acaacccccc ctgtcctgga cagcgatggc   1500
tccttcttcc tgtacagcaa gctgacagtg gataagagcc ggtggcagca gggaaacgtc   1560
tttagctgca gcgtgatgca tgaggccctg cacaatcact acacccagaa gtccctgtcc   1620
ctgagccctg gcgaggcgg cggcggcggc agcggcggag cggatccgg cggaggcggc     1680 tccggagaca ccggaaggcc cttcgtggag atgtacagcg agattcctga gattatccac   1740
atgaccgagg acgggaact ggtgattccc tgccgggtca ccagcccaa catcaccgtg      1800 accctcaaga agttccccct ggacaccctg atccctgacg gcaaaaggat tatctgggac   1860
agccggaagg gctttatcat cagcaatgcc acatacaagg agattggact cctgacctgc   1920
gaggctacag tcaacggaca cctgtacaag accaactacc tgacccaccg gcagaccaat   1980
accatcatcg acgtggtgct gagccccagc cacggaattg agctgagcgt gggagaaaaa   2040
ctcgtgctca actgcacagc ccggaccgaa ctcaatgtcg gaatcgactt caactgggaa   2100
taccccagct ccaagcacca gcacaagaag ctggtcaacc gggatctcaa gacccagtcc   2160
ggcagcgaaa tgaagaagtt cctcagcacc ctgaccatcg atggcgtcac aaggagcgat   2220
cagggactct acacctgcgc cgctagctcc ggactcatga ccaagaagaa ctccacattt   2280
gtccgggtgc acgaaaagtg a                                             2301
```

<210> SEQ ID NO 42
<211> LENGTH: 766
<212> TYPE: PRT
<213> ORGANISM: Artificial Sequence
<220> FEATURE:
<223> OTHER INFORMATION: Fusion Protein 6 sequence

<400> SEQUENCE: 42

```
Met Glu Phe Gly Leu Ser Trp Leu Phe Leu Val Ala Ile Leu Lys Gly
 1               5                  10                  15

Val Gln Cys Leu Val Val Thr Pro Pro Gly Pro Glu Leu Val Leu Asn
             20                  25                  30

Val Ser Ser Thr Phe Val Leu Thr Cys Ser Gly Ser Ala Pro Val Val
         35                  40                  45

Trp Glu Arg Met Ser Gln Glu Pro Pro Gln Glu Met Ala Lys Ala Gln
     50                  55                  60

Asp Gly Thr Phe Ser Ser Val Leu Thr Leu Thr Asn Leu Thr Gly Leu
 65                  70                  75                  80
```

-continued

Asp Thr Gly Glu Tyr Phe Cys Thr His Asn Asp Ser Arg Gly Leu Glu
                85                  90                  95

Thr Asp Glu Arg Lys Arg Leu Tyr Ile Phe Val Pro Asp Pro Thr Val
            100                 105                 110

Gly Phe Leu Pro Asn Asp Ala Glu Glu Leu Phe Ile Phe Leu Thr Glu
        115                 120                 125

Ile Thr Glu Ile Thr Ile Pro Cys Arg Val Thr Asp Pro Gln Leu Val
    130                 135                 140

Val Thr Leu His Glu Lys Lys Gly Asp Val Ala Leu Pro Val Pro Tyr
145                 150                 155                 160

Asp His Gln Arg Gly Phe Ser Gly Ile Phe Glu Asp Arg Ser Tyr Ile
                165                 170                 175

Cys Lys Thr Thr Ile Gly Asp Arg Glu Val Asp Ser Asp Ala Tyr Tyr
            180                 185                 190

Val Tyr Arg Leu Gln Val Ser Ser Ile Asn Val Ser Val Asn Ala Val
        195                 200                 205

Gln Thr Val Val Arg Gln Gly Glu Asn Ile Thr Leu Met Cys Ile Val
    210                 215                 220

Ile Gly Asn Glu Val Val Asn Phe Glu Trp Thr Tyr Pro Arg Lys Glu
225                 230                 235                 240

Ser Gly Arg Leu Val Glu Pro Val Thr Asp Phe Leu Leu Asp Met Pro
                245                 250                 255

Tyr His Ile Arg Ser Ile Leu His Ile Pro Ser Ala Glu Leu Glu Asp
            260                 265                 270

Ser Gly Thr Tyr Thr Cys Asn Val Thr Glu Ser Val Asn Asp His Gln
        275                 280                 285

Asp Glu Lys Ala Ile Asn Ile Thr Val Val Glu Ser Gly Tyr Val Arg
    290                 295                 300

Leu Leu Gly Glu Val Gly Thr Leu Gln Phe Ala Glu Ala Ser Asp Lys
305                 310                 315                 320

Thr His Thr Cys Pro Pro Cys Pro Ala Pro Glu Leu Leu Gly Gly Pro
                325                 330                 335

Ser Val Phe Leu Phe Pro Pro Lys Pro Lys Asp Thr Leu Met Ile Ser
            340                 345                 350

Arg Thr Pro Glu Val Thr Cys Val Val Val Asp Val Ser His Glu Asp
        355                 360                 365

Pro Glu Val Lys Phe Asn Trp Tyr Val Asp Gly Val Glu Val His Asn
    370                 375                 380

Ala Lys Thr Lys Pro Arg Glu Glu Gln Tyr Asn Ser Thr Tyr Arg Val
385                 390                 395                 400

Val Ser Val Leu Thr Val Leu His Gln Asp Trp Leu Asn Gly Lys Glu
                405                 410                 415

Tyr Lys Cys Lys Val Ser Asn Lys Ala Leu Pro Ala Pro Ile Glu Lys
            420                 425                 430

Thr Ile Ser Lys Ala Lys Gly Gln Pro Arg Glu Pro Gln Val Tyr Thr
        435                 440                 445

Leu Pro Pro Ser Arg Asp Glu Leu Thr Lys Asn Gln Val Ser Leu Thr
    450                 455                 460

Cys Leu Val Lys Gly Phe Tyr Pro Ser Asp Ile Ala Val Glu Trp Glu
465                 470                 475                 480

Ser Asn Gly Gln Pro Glu Asn Asn Tyr Lys Thr Thr Pro Pro Val Leu
                485                 490                 495

Asp Ser Asp Gly Ser Phe Phe Leu Tyr Ser Lys Leu Thr Val Asp Lys
                500                 505                 510

Ser Arg Trp Gln Gln Gly Asn Val Phe Ser Cys Ser Val Met His Glu
            515                 520                 525

Ala Leu His Asn His Tyr Thr Gln Lys Ser Leu Ser Leu Ser Pro Gly
        530                 535                 540

Gly Gly Gly Gly Gly Gly Ser Gly Gly Gly Gly Ser Gly Gly Gly Gly
545                 550                 555                 560

Ser Gly Asp Thr Gly Arg Pro Phe Val Glu Met Tyr Ser Glu Ile Pro
                565                 570                 575

Glu Ile Ile His Met Thr Glu Gly Arg Glu Leu Val Ile Pro Cys Arg
            580                 585                 590

Val Thr Ser Pro Asn Ile Thr Val Thr Leu Lys Lys Phe Pro Leu Asp
        595                 600                 605

Thr Leu Ile Pro Asp Gly Lys Arg Ile Ile Trp Asp Ser Arg Lys Gly
    610                 615                 620

Phe Ile Ile Ser Asn Ala Thr Tyr Lys Glu Ile Gly Leu Leu Thr Cys
625                 630                 635                 640

Glu Ala Thr Val Asn Gly His Leu Tyr Lys Thr Asn Tyr Leu Thr His
                645                 650                 655

Arg Gln Thr Asn Thr Ile Ile Asp Val Val Leu Ser Pro Ser His Gly
            660                 665                 670

Ile Glu Leu Ser Val Gly Glu Lys Leu Val Leu Asn Cys Thr Ala Arg
        675                 680                 685

Thr Glu Leu Asn Val Gly Ile Asp Phe Asn Trp Glu Tyr Pro Ser Ser
    690                 695                 700

Lys His Gln His Lys Lys Leu Val Asn Arg Asp Leu Lys Thr Gln Ser
705                 710                 715                 720

Gly Ser Glu Met Lys Lys Phe Leu Ser Thr Leu Thr Ile Asp Gly Val
                725                 730                 735

Thr Arg Ser Asp Gln Gly Leu Tyr Thr Cys Ala Ala Ser Ser Gly Leu
            740                 745                 750

Met Thr Lys Lys Asn Ser Thr Phe Val Arg Val His Glu Lys
        755                 760                 765

<210> SEQ ID NO 43
<211> LENGTH: 2307
<212> TYPE: DNA
<213> ORGANISM: Artificial Sequence
<220> FEATURE:
<223> OTHER INFORMATION: Coding sequence of Fusion Proteins 3 and 4
      sequence

<400> SEQUENCE: 43
atggagacag acacactcct gctatgggta ctgcttcttt gggttcccgg atccactggc      60
cagggcctgg tcgtcacacc cccgggggcca gagcttgtcc tcaatgtctc cagcaccttc     120
gttctgacct gctcgggttc agctccggtg gtgtgggaac ggatgtccca ggagccccca     180
caggaaatgg ccaaggccca ggatggcacc ttctccagcg tgctcacact gaccaacctc     240
actgggctag acacgggaga atacttttgc acccacaatg actcccgtgg actgagagacc     300 gatgagcgga acggctcta catctttgtg ccagatccca ccgtgggctt cctccctaat       360
gatgccgagg aactattcat ctttctcacg gaaataactg agatcaccat tccatgccga      420
gtaacagacc acagctggt ggtgacactg acgagaaga aaggggacgt tgcactgcct        480
gtcccctatg atcaccaacg tggctttttcc ggtatctttg aggacagaag ctacatctgc     540

```
aaaaccacca ttggggacag ggaggtggat tctgatgcct actatgtcta cagactccag      600
gtgtcatcca tcaacgtctc tgtgaacgca gtgcagactg tggtccgcca gggtgagaac      660
atcaccctca tgtgcattgt gatcgggaat gaggtggtca acttcgagtg gacataccccc    720 cgcaaagaaa gtgggcggct ggtggagccg gtgactgact tcctcttgga tatgccttac      780
cacatccgct ccatcctgca catccccagt gccgagttag aagactcggg gacctacacc      840
tgcaatgtga cggagagtgt gaatgaccat caggatgaaa aggccatcaa catcaccgtg      900
gttgagagcg gctacgtgcg gctcctggga gaggtgggca cactacaatt tgctgaggct      960
agcgacaaaa ctcacacatg tccaccgtgt ccagcacctg aactcctggg tggaccgtca      1020
gtcttcctct ccccccaaa acccaaggac accctcatga tctcccggac ccctgaggtc       1080
acatgcgtgg tggtggacgt gagccacgaa gaccctgagg tcaagttcaa ctggtacgtg      1140
gacggcgtgg aggtgcataa tgccaagaca agccgcggg aggagcagta caacagcacg       1200
taccgtgtgg tcagcgtcct caccgtcctg caccaggact ggctgaatgg caaggagtac      1260
aagtgcaagg tctccaacaa agccctccca gcccccatcg agaaaaccat ctccaaagcc      1320
aaagggcagc cccgagaacc acaggtgtac accctgcccc catcccggga tgagctgacc      1380
aagaaccagg tcagcctgac ctgcctggtc aaaggcttct atcccagcga catcgccgtg      1440
gagtgggaga gcaatgggca gccggagaac aactacaaga ccacgcctcc cgtgctggac      1500
tccgacggct ccttcttcct ctacagcaag ctcaccgtgg acaagagcag gtggcagcag      1560
gggaacgtct tctcatgctc cgtgatgcat gaggctctgc acaaccacta cacgcagaag      1620
agcctctccc tgtctccggg tggtggagga ggcggtggat ctggtggcgg tggaagcgga      1680
ggtggaggtt ccggagacac tggtagacct tttgttgaaa tgtattctga aattcctgaa      1740
attattcata tgactgaagg aagagaactt gttattcctt gtagagttac ttctcctaat      1800
attactgtta ctcttaagaa gtttcctctt gatactctta ttcctgatgg aaagagaatt      1860
atttgggatt ctagaaaggg atttattatt tctaatgcta cttataagga aattggactt      1920
cttacttgtg aagctactgt taatggacat ctttataaga ctaattatct tactcataga      1980
caaactaata ccatcatcga cgtggttctg agtccgtctc atggaattga actatctgtt      2040
ggagaaaagc ttgtcttaaa ttgtacagca agaactgaac taaatgtggg gattgacttc      2100
aactgggaat ccttcttc gaagcatcag cataagaaac ttgtaaaccg agacctaaaa       2160
acccagtctg ggagtgagat gaagaaattc ttgagcaccc tgactataga tggtgtaacc      2220
cggagtgacc aaggattgta cacctgtgca gcatccagtg ggctgatgac caagaagaac      2280
agcacatttg tcagggtcca tgaaaaa                                           2307
```

<210> SEQ ID NO 44
<211> LENGTH: 769
<212> TYPE: PRT
<213> ORGANISM: Artificial Sequence
<220> FEATURE:
<223> OTHER INFORMATION: Fusion Protein 3 or 4 plus a signal peptide
      sequence

<400> SEQUENCE: 44

Met Glu Thr Asp Thr Leu Leu Leu Trp Val Leu Leu Leu Trp Val Pro
1               5                   10                  15

Gly Ser Thr Gly Gln Gly Leu Val Val Thr Pro Pro Gly Pro Glu Leu
            20                  25                  30

Val Leu Asn Val Ser Ser Thr Phe Val Leu Thr Cys Ser Gly Ser Ala

```
            35                  40                  45
Pro Val Val Trp Glu Arg Met Ser Gln Glu Pro Gln Glu Met Ala
 50                  55                  60
Lys Ala Gln Asp Gly Thr Phe Ser Ser Val Leu Thr Leu Thr Asn Leu
 65                      70                  75                  80
Thr Gly Leu Asp Thr Gly Glu Tyr Phe Cys Thr His Asn Asp Ser Arg
                     85                  90                  95
Gly Leu Glu Thr Asp Glu Arg Lys Arg Leu Tyr Ile Phe Val Pro Asp
                100                 105                 110
Pro Thr Val Gly Phe Leu Pro Asn Asp Ala Glu Glu Leu Phe Ile Phe
                115                 120                 125
Leu Thr Glu Ile Thr Glu Ile Thr Ile Pro Cys Arg Val Thr Asp Pro
            130                 135                 140
Gln Leu Val Val Thr Leu His Glu Lys Lys Gly Asp Val Ala Leu Pro
145                 150                 155                 160
Val Pro Tyr Asp His Gln Arg Gly Phe Ser Gly Ile Phe Glu Asp Arg
                165                 170                 175
Ser Tyr Ile Cys Lys Thr Thr Ile Gly Asp Arg Glu Val Asp Ser Asp
                180                 185                 190
Ala Tyr Tyr Val Tyr Arg Leu Gln Val Ser Ser Ile Asn Val Ser Val
                195                 200                 205
Asn Ala Val Gln Thr Val Val Arg Gln Gly Glu Asn Ile Thr Leu Met
210                 215                 220
Cys Ile Val Ile Gly Asn Glu Val Val Asn Phe Glu Trp Thr Tyr Pro
225                 230                 235                 240
Arg Lys Glu Ser Gly Arg Leu Val Glu Pro Val Thr Asp Phe Leu Leu
                245                 250                 255
Asp Met Pro Tyr His Ile Arg Ser Ile Leu His Ile Pro Ser Ala Glu
                260                 265                 270
Leu Glu Asp Ser Gly Thr Tyr Thr Cys Asn Val Thr Glu Ser Val Asn
                275                 280                 285
Asp His Gln Asp Glu Lys Ala Ile Asn Ile Thr Val Val Glu Ser Gly
            290                 295                 300
Tyr Val Arg Leu Leu Gly Glu Val Gly Thr Leu Gln Phe Ala Glu Ala
305                 310                 315                 320
Ser Asp Lys Thr His Thr Cys Pro Pro Cys Pro Ala Pro Glu Leu Leu
                325                 330                 335
Gly Gly Pro Ser Val Phe Leu Phe Pro Pro Lys Pro Lys Asp Thr Leu
                340                 345                 350
Met Ile Ser Arg Thr Pro Glu Val Thr Cys Val Val Val Asp Val Ser
                355                 360                 365
His Glu Asp Pro Glu Val Lys Phe Asn Trp Tyr Val Asp Gly Val Glu
                370                 375                 380
Val His Asn Ala Lys Thr Lys Pro Arg Glu Glu Gln Tyr Asn Ser Thr
385                 390                 395                 400
Tyr Arg Val Val Ser Val Leu Thr Val Leu His Gln Asp Trp Leu Asn
                    405                 410                 415
Gly Lys Glu Tyr Lys Cys Lys Val Ser Asn Lys Ala Leu Pro Ala Pro
                420                 425                 430
Ile Glu Lys Thr Ile Ser Lys Ala Lys Gly Gln Pro Arg Glu Pro Gln
                435                 440                 445
Val Tyr Thr Leu Pro Pro Ser Arg Asp Glu Leu Thr Lys Asn Gln Val
                450                 455                 460
```

```
Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
            485                 490                 495

Pro Val Leu Asp Ser Asp Gly Ser Phe Phe Leu Tyr Ser Lys Leu Thr
        500                 505                 510

Val Asp Lys Ser Arg Trp Gln Gln Gly Asn Val Phe Ser Cys Ser Val
    515                 520                 525

Met His Glu Ala Leu His Asn His Tyr Thr Gln Lys Ser Leu Ser Leu
530                 535                 540

Ser Pro Gly Gly Gly Gly Gly Gly Ser Gly Gly Gly Gly Ser Gly Gly
545                 550                 555                 560

Gly Gly Ser Gly Asp Thr Gly Arg Pro Phe Val Glu Met Tyr Ser
            565                 570                 575

Glu Ile Pro Glu Ile Ile His Met Thr Glu Gly Arg Glu Leu Val Ile
        580                 585                 590

Pro Cys Arg Val Thr Ser Pro Asn Ile Thr Val Thr Leu Lys Lys Phe
    595                 600                 605

Pro Leu Asp Thr Leu Ile Pro Asp Gly Lys Arg Ile Ile Trp Asp Ser
610                 615                 620

Arg Lys Gly Phe Ile Ile Ser Asn Ala Thr Tyr Lys Glu Ile Gly Leu
625                 630                 635                 640

Leu Thr Cys Glu Ala Thr Val Asn Gly His Leu Tyr Lys Thr Asn Tyr
            645                 650                 655

Leu Thr His Arg Gln Thr Asn Thr Ile Ile Asp Val Val Leu Ser Pro
        660                 665                 670

Ser His Gly Ile Glu Leu Ser Val Gly Glu Lys Leu Val Leu Asn Cys
    675                 680                 685

Thr Ala Arg Thr Glu Leu Asn Val Gly Ile Asp Phe Asn Trp Glu Tyr
690                 695                 700

Pro Ser Ser Lys His Gln His Lys Lys Leu Val Asn Arg Asp Leu Lys
705                 710                 715                 720

Thr Gln Ser Gly Ser Glu Met Lys Lys Phe Leu Ser Thr Leu Thr Ile
            725                 730                 735

Asp Gly Val Thr Arg Ser Asp Gln Gly Leu Tyr Thr Cys Ala Ala Ser
        740                 745                 750

Ser Gly Leu Met Thr Lys Lys Asn Ser Thr Phe Val Arg Val His Glu
    755                 760                 765

Lys

<210> SEQ ID NO 45
<211> LENGTH: 1353
<212> TYPE: DNA
<213> ORGANISM: Artificial Sequence
<220> FEATURE:
<223> OTHER INFORMATION: Coding sequence of VEGF Trap sequence

<400> SEQUENCE: 45
atggagacag acacactcct gctatgggta ctgctgctct gggttccagg gtcgactggc      60
gacactggaa gacctttgt tgaaatgtat tctgaaattc ctgaaattat tcatatgact     120
gaaggaagag aacttgttat tccttgtaga gttacttctc ctaatattac tgttactctt     180
aagaagtttc ctcttgatac tcttattcct gatggaaaga gaattatttg ggattctaga     240
aagggattta ttatttctaa tgctacttat aaggaaattg gacttcttac ttgtgaagct     300
```

-continued

```
actgttaatg gacatcttta taagactaat tatcttactc atagacaaac taataccatc      360
atcgacgtgg ttctgagtcc gtctcatgga attgaactat ctgttggaga aaagcttgtc      420
ttaaattgta cagcaagaac tgaactaaat gtggggattg acttcaactg ggaatacccc      480
tcttcgaagc atcagcataa gaaacttgta accgagacc taaaaaccca gtctgggagt      540
gagatgaaga aattcttgag caccctgact atagatggtg taacccggag tgaccaagga      600
ttgtacacct gtcagcatc cagtgggctg atgaccaaga agaacagcac atttgtcagg      660
gtccatgaaa aagacaaaac tcacacatgt ccaccgtgtc cagcacctga actcctgggt      720
ggaccgtcag tcttcctctt cccccccaaaa cccaaggaca ccctcatgat ctcccggacc      780
cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcccag cccccatcga gaaaaccatc     1020
tccaaagcca agggcagcc cgagaaccaa caggtgtaca ccctgccccc atcccgggat     1080
gagctgacca gaaccaggt cagcctgacc tgcctggtca aaggcttcta tcccagcgac     1140
atcgccgtgg agtgggagag caatgggcag ccggagaaca actacaagac cacgcctccc     1200
gtgctggact ccgacggctc cttcttcctc tacagcaagc tcaccgtgga caagagcagg     1260
tggcagcagg ggaacgtctt ctcatgctcc gtgatgcatg aggctctgca caaccactac     1320
acgcagaaga gcctctcccct gtctccgggt aaa                                 1353
```

<210> SEQ ID NO 46
<211> LENGTH: 451
<212> TYPE: PRT
<213> ORGANISM: Artificial Sequence
<220> FEATURE:
<223> OTHER INFORMATION: VEGF Trap sequence Plus a signal sequence

<400> SEQUENCE: 46

```
Met Glu Thr Asp Thr Leu Leu Leu Trp Val Leu Leu Leu Trp Val Pro
1               5                   10                  15

Gly Ser Thr Gly Asp Thr Gly Arg Pro Phe Val Glu Met Tyr Ser Glu
                20                  25                  30

Ile Pro Glu Ile Ile His Met Thr Glu Gly Arg Glu Leu Val Ile Pro
            35                  40                  45

Cys Arg Val Thr Ser Pro Asn Ile Thr Val Thr Leu Lys Lys Phe Pro
        50                  55                  60

Leu Asp Thr Leu Ile Pro Asp Gly Lys Arg Ile Ile Trp Asp Ser Arg
65                  70                  75                  80

Lys Gly Phe Ile Ile Ser Asn Ala Thr Tyr Lys Glu Ile Gly Leu Leu
                85                  90                  95

Thr Cys Glu Ala Thr Val Asn Gly His Leu Tyr Lys Thr Asn Tyr Leu
            100                 105                 110

Thr His Arg Gln Thr Asn Thr Ile Ile Asp Val Val Leu Ser Pro Ser
        115                 120                 125

His Gly Ile Glu Leu Ser Val Gly Glu Lys Leu Val Leu Asn Cys Thr
    130                 135                 140

Ala Arg Thr Glu Leu Asn Val Gly Ile Asp Phe Asn Trp Glu Tyr Pro
145                 150                 155                 160

Ser Ser Lys His Gln His Lys Lys Leu Val Asn Arg Asp Leu Lys Thr
                165                 170                 175
```

Gln Ser Gly Ser Glu Met Lys Lys Phe Leu Ser Thr Leu Thr Ile Asp
            180                 185                 190

Gly Val Thr Arg Ser Asp Gln Gly Leu Tyr Thr Cys Ala Ala Ser Ser
            195                 200                 205

Gly Leu Met Thr Lys Lys Asn Ser Thr Phe Val Arg Val His Glu Lys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
            435                 440                 445

Pro Gly Lys
    450

<210> SEQ ID NO 47
<211> LENGTH: 1644
<212> TYPE: DNA
<213> ORGANISM: Artificial Sequence
<220> FEATURE:
<223> OTHER INFORMATION: Coding sequence of PDGF Trap sequence

<400> SEQUENCE: 47
atggagacag acacactcct gctatgggta ctgcttcttt gggttcccgg atccactggc    60
cagggcctgg tcgtcacacc cccggggcca gagcttgtcc tcaatgtctc cagcaccttc   120
gttctgacct gctcgggttc agctccggtg gtgtgggaac ggatgtccca ggagccccca   180
caggaaatgg ccaaggccca ggatggcacc ttctccagcg tgctcacact gaccaacctc   240
actgggctag acacgggaga atactttgc acccacaatg actcccgtgg actggagacc   300
gatgagcgga acggctcta catctttgtg ccagatccca ccgtgggctt cctccctaat   360
gatgccgagg aactattcat ctttctcacg gaaataactg agatcaccat tccatgccga   420

```
gtaacagacc cacagctggt ggtgacactg cacgagaaga aaggggacgt tgcactgcct    480
gtcccctatg atcaccaacg tggctttttt ggtatctttg aggacagaag ctacatctgc    540
aaaaccacca ttggggacag ggaggtggat tctgatgcct actatgtcta cagactccag    600
gtgtcatcca tcaacgtctc tgtgaacgca gtgcagactg tggtccgcca gggtgagaac    660
atcaccctca tgtgcattgt gatcgggaat gaggtggtca acttcgagtg gacatacccc    720
cgcaaagaaa gtgggcggct ggtggagccg gtgactgact tcctcttgga tatgccttac    780
cacatccgct ccatcctgca catccccagt gccgagttag aagactcggg gacctacacc    840
tgcaatgtga cggagagtgt gaatgaccat caggatgaaa aggccatcaa catcaccgtg    900
gttgagagcg gctacgtgcg gctcctggga gaggtgggca cactacaatt tgctgaggct    960
agcgacaaaa ctcacacatg tccaccgtgt ccagcacctg aactcctggg tggaccgtca   1020
gtcttcctct tccccccaaa acccaaggac accctcatga tctcccggac ccctgaggtc   1080
acatgcgtgg tggtggacgt gagccacgaa gaccctgagg tcaagttcaa ctggtacgtg   1140
gacggcgtgg aggtgcataa tgccaagaca aagccgcggg aggagcagta caacagcacg   1200
taccgtgtgg tcagcgtcct caccgtcctg caccaggact ggctgaatgg caaggagtac   1260
aagtgcaagg tctccaacaa agccctccca gcccccatcg agaaaaccat ctccaaagcc   1320
aaagggcagc cccgagaacc acaggtgtac accctgcccc catcccggga tgagctgacc   1380
aagaaccagg tcagcctgac ctgcctggtc aaaggcttct atcccagcga catcgccgtg   1440
gagtgggaga gcaatgggca gccggagaac aactacaaga ccacgcctcc cgtgctggac   1500
tccgacggct ccttcttcct ctacagcaag ctcaccgtgg acaagagcag gtggcagcag   1560
gggaacgtct tctcatgctc cgtgatgcat gaggctctgc acaaccacta cacgcagaag   1620
agcctctccc tgtctccggg taaa                                          1644
```

<210> SEQ ID NO 48
<211> LENGTH: 548
<212> TYPE: PRT
<213> ORGANISM: Artificial Sequence
<220> FEATURE:
<223> OTHER INFORMATION: PDGF Trap sequence plus a signal sequence

<400> SEQUENCE: 48

```
Met Glu Thr Asp Thr Leu Leu Leu Trp Val Leu Leu Trp Val Pro
1               5                   10                  15

Gly Ser Thr Gly Gln Gly Leu Val Val Thr Pro Pro Gly Pro Glu Leu
            20                  25                  30

Val Leu Asn Val Ser Ser Thr Phe Val Leu Thr Cys Ser Gly Ser Ala
        35                  40                  45

Pro Val Val Trp Glu Arg Met Ser Gln Glu Pro Pro Gln Glu Met Ala
    50                  55                  60

Lys Ala Gln Asp Gly Thr Phe Ser Ser Val Leu Thr Leu Thr Asn Leu
65                  70                  75                  80

Thr Gly Leu Asp Thr Gly Glu Tyr Phe Cys Thr His Asn Asp Ser Arg
                85                  90                  95

Gly Leu Glu Thr Asp Glu Arg Lys Arg Leu Tyr Ile Phe Val Pro Asp
            100                 105                 110

Pro Thr Val Gly Phe Leu Pro Asn Asp Ala Glu Glu Leu Phe Ile Phe
        115                 120                 125

Leu Thr Glu Ile Thr Glu Ile Thr Ile Pro Cys Arg Val Thr Asp Pro
    130                 135                 140
```

-continued

```
Gln Leu Val Val Thr Leu His Glu Lys Lys Gly Asp Val Ala Leu Pro
145                 150                 155                 160

Val Pro Tyr Asp His Gln Arg Gly Phe Phe Gly Ile Phe Glu Asp Arg
            165                 170                 175

Ser Tyr Ile Cys Lys Thr Thr Ile Gly Asp Arg Glu Val Asp Ser Asp
            180                 185                 190

Ala Tyr Tyr Val Tyr Arg Leu Gln Val Ser Ser Ile Asn Val Ser Val
            195                 200                 205

Asn Ala Val Gln Thr Val Val Arg Gln Gly Glu Asn Ile Thr Leu Met
            210                 215                 220

Cys Ile Val Ile Gly Asn Glu Val Val Asn Phe Glu Trp Thr Tyr Pro
225                 230                 235                 240

Arg Lys Glu Ser Gly Arg Leu Val Glu Pro Val Thr Asp Phe Leu Leu
            245                 250                 255

Asp Met Pro Tyr His Ile Arg Ser Ile Leu His Ile Pro Ser Ala Glu
            260                 265                 270

Leu Glu Asp Ser Gly Thr Tyr Thr Cys Asn Val Thr Glu Ser Val Asn
            275                 280                 285

Asp His Gln Asp Glu Lys Ala Ile Asn Ile Thr Val Val Glu Ser Gly
            290                 295                 300

Tyr Val Arg Leu Leu Gly Glu Val Gly Thr Leu Gln Phe Ala Glu Ala
305                 310                 315                 320

Ser Asp Lys Thr His Thr Cys Pro Pro Cys Pro Ala Pro Glu Leu Leu
            325                 330                 335

Gly Gly Pro Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
            355                 360                 365

His Glu Asp Pro Glu Val Lys Phe Asn Trp Tyr Val Asp Gly Val Glu
            370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
            405                 410                 415

Gly Lys Glu Tyr Lys Cys Lys Val Ser Asn Lys Ala Leu Pro Ala Pro
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Arg Asp Glu Leu Thr Lys Asn Gln Val
            450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
            485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
            515                 520                 525

Met His Glu Ala Leu His Asn His Tyr Thr Gln Lys Ser Leu Ser Leu
            530                 535                 540

Ser Pro Gly Lys
545
```

<210> SEQ ID NO 49
<211> LENGTH: 2250
<212> TYPE: DNA
<213> ORGANISM: Artificial Sequence
<220> FEATURE:
<223> OTHER INFORMATION: Coding sequence of Fusion Protein 5 sequence

<400> SEQUENCE: 49

```
cagggcctgg tcgtgacacc tcccggaccc gagctggtgc tcaacgtctc ctccaccttt      60
gtgctgacat gcagcggcag cgctcctgtg gtctgggaac ggatgtccca ggagcctccc     120
caggaaatgg ccaaggccca ggacggcacc ttttccagcg tcctcacact caccaacctg     180
acaggcctgg acaccggcga gtactttgc acccacaatg actccagggg actggaaacc     240
gatgagcgga agcggctcta cattttcgtc cccgacccca ccgtcggatt tctgcctaat     300
gacgctgaag agctgtttat cttcctgaca gagatcaccg aaatcaccat ccctgtcgg     360 gtcaccgatc cccagctggt ggtcacactg cacgagaaga agggagatgt cgccctgcct     420
gtgccttatg accatcagag gggcttttcc ggcattttcg aggacaggag ctacatctgc     480
aaaaccacca tcggagaccg ggaggtcgac agcgatgcct attacgtcta ccggctccag     540
gtctcctcca tcaatgtgag cgtgaatgct gtccagacag tggtccggca gggcgagaat     600
atcacactga tgtgcattgt cattggcaac gaggtggtca acttcgagtg gacctatcct     660
aggaaggaga gcggccggct cgtcgaacct gtgaccgact cctcctggga catgccttac     720
cacattcggt ccatcctgca cattcctagc gccgagctgg aggacagcgg aacctacacc     780
tgcaacgtga ccgagtccgt gaatgaccac caggatgaga aggccatcaa catcacagtc     840
gtggagagcg gatacgtcag gctgctcgga gaagtcggca cactgcagtt cgccgaggcc     900
agcgataaga cccacacctg tcctccttgt cctgctcctg agctcctcgg cggacctagc     960
gtgttcctgt tccccctaa gcctaaagac accctcatga tcagccggac ccccgaggtc    1020
acatgcgtgg tggtcgacgt ctcccatgag gatcccgagg tgaagttcaa ttggtacgtc    1080
gacggcgtcg aggtccacaa tgccaaaacc aaaccccggg aggagcagta caacagcacc    1140
tatagggtgg tcagcgtcct gaccgtgctg caccaagact ggctgaacgg caaggagtac    1200
aaatgcaaag tcagcaataa ggcccctccc gccccccattg agaagaccat ctccaaggct    1260
aagggccaac ctagggagcc ccaggtgtac accctgcctc ccagccggga tgagctgaca    1320
aagaaccagg tgagcctcac ctgtctggtg aagggctttt accctccga tattgccgtg    1380 gagtgggaaa gcaacggaca gcctgagaac aactacaaga caacccccccc tgtcctggac    1440 agcgatggct ccttcttcct gtacagcaag ctgacagtgg ataagagccg gtggcagcag    1500
ggaaacgtct ttagctgcag cgtgatgcat gaggccctgc acaatcacta cacccagaag    1560
tccctgtccc tgagccctgg cggaggcggc ggcggcggca gcggcggagg cggatccggc    1620
ggaggcggct ccggagacac cggaaggccc ttcgtggaga tgtacagcga gattcctgag    1680
attatccaca tgaccgaggg acgggaactg gtgattccct gccgggtcac cagccccaac    1740
atcaccgtga ccctcaagaa gttccccctg gacacctga tccctgacgg caaaaggatt    1800
atctgggaca gccggaaggg cttttatcat cagcaatgcca catacaagga gattggactc    1860
ctgacctgcg aggctacagt caacggacac ctgtacaaga ccaactacct gacccaccgg    1920
cagaccaata ccatcatcga cgtggtgctg agccccagcc acggaattga gctgagcgtg    1980
ggagaaaaac tcgtgctcaa ctgcacagcc cggaccgaac tcaatgtcgg aatcgacttc    2040
aactgggaat accccagctc caagcaccag cacaagaagc tggtcaaccg ggatctcaag    2100
```

```
acccagtccg gcagcgaaat gaagaagttc ctcagcaccc tgaccatcga tggcgtcaca    2160
aggagcgatc agggactcta cacctgcgcc gctagctccg gactcatgac caagaagaac    2220
tccacatttg tccgggtgca cgaaaagtga                                      2250
```

<210> SEQ ID NO 50
<211> LENGTH: 768
<212> TYPE: PRT
<213> ORGANISM: Artificial Sequence
<220> FEATURE:
<223> OTHER INFORMATION: Fusion Protein 5 plus a signal peptide sequence

<400> SEQUENCE: 50

```
Met Glu Phe Gly Leu Ser Trp Leu Phe Leu Val Ala Ile Leu Lys Gly
1               5                   10                  15

Val Gln Cys Gln Gly Leu Val Val Thr Pro Pro Gly Pro Glu Leu Val
            20                  25                  30

Leu Asn Val Ser Ser Thr Phe Val Leu Thr Cys Ser Gly Ser Ala Pro
        35                  40                  45

Val Val Trp Glu Arg Met Ser Gln Glu Pro Pro Gln Glu Met Ala Lys
    50                  55                  60

Ala Gln Asp Gly Thr Phe Ser Ser Val Leu Thr Leu Thr Asn Leu Thr
65                  70                  75                  80

Gly Leu Asp Thr Gly Glu Tyr Phe Cys Thr His Asn Asp Ser Arg Gly
                85                  90                  95

Leu Glu Thr Asp Glu Arg Lys Arg Leu Tyr Ile Phe Val Pro Asp Pro
            100                 105                 110

Thr Val Gly Phe Leu Pro Asn Asp Ala Glu Glu Leu Phe Ile Phe Leu
        115                 120                 125

Thr Glu Ile Thr Glu Ile Thr Ile Pro Cys Arg Val Thr Asp Pro Gln
    130                 135                 140

Leu Val Val Thr Leu His Glu Lys Lys Gly Asp Val Ala Leu Pro Val
145                 150                 155                 160

Pro Tyr Asp His Gln Arg Gly Phe Ser Gly Ile Phe Glu Asp Arg Ser
                165                 170                 175

Tyr Ile Cys Lys Thr Thr Ile Gly Asp Arg Glu Val Asp Ser Asp Ala
            180                 185                 190

Tyr Tyr Val Tyr Arg Leu Gln Val Ser Ser Ile Asn Val Ser Val Asn
        195                 200                 205

Ala Val Gln Thr Val Val Arg Gln Gly Glu Asn Ile Thr Leu Met Cys
    210                 215                 220

Ile Val Ile Gly Asn Glu Val Val Asn Phe Glu Trp Thr Tyr Pro Arg
225                 230                 235                 240

Lys Glu Ser Gly Arg Leu Val Glu Pro Val Thr Asp Phe Leu Leu Asp
                245                 250                 255

Met Pro Tyr His Ile Arg Ser Ile Leu His Ile Pro Ser Ala Glu Leu
            260                 265                 270

Glu Asp Ser Gly Thr Tyr Thr Cys Asn Val Thr Glu Ser Val Asn Asp
        275                 280                 285

His Gln Asp Glu Lys Ala Ile Asn Ile Thr Val Val Glu Ser Gly Tyr
    290                 295                 300

Val Arg Leu Leu Gly Glu Val Gly Thr Leu Gln Phe Ala Glu Ala Ser
305                 310                 315                 320

Asp Lys Thr His Thr Cys Pro Pro Cys Pro Ala Pro Glu Leu Leu Gly
                325                 330                 335
```

```
Gly Pro Ser Val Phe Leu Phe Pro Pro Lys Pro Lys Asp Thr Leu Met
                340                 345                 350

Ile Ser Arg Thr Pro Glu Val Thr Cys Val Val Val Asp Val Ser His
            355                 360                 365

Glu Asp Pro Glu Val Lys Phe Asn Trp Tyr Val Asp Gly Val Glu Val
        370                 375                 380

His Asn Ala Lys Thr Lys Pro Arg Glu Glu Gln Tyr Asn Ser Thr Tyr
385                 390                 395                 400

Arg Val Val Ser Val Leu Thr Val Leu His Gln Asp Trp Leu Asn Gly
                405                 410                 415

Lys Glu Tyr Lys Cys Lys Val Ser Asn Lys Ala Leu Pro Ala Pro Ile
            420                 425                 430

Glu Lys Thr Ile Ser Lys Ala Lys Gly Gln Pro Arg Glu Pro Gln Val
        435                 440                 445

Tyr Thr Leu Pro Pro Ser Arg Asp Glu Leu Thr Lys Asn Gln Val Ser
    450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Val Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
        515                 520                 525

His Glu Ala Leu His Asn His Tyr Thr Gln Lys Ser Leu Ser Leu Ser
    530                 535                 540

Pro Gly Gly Gly Gly Gly Gly Ser Gly Gly Gly Ser Gly Gly
545                 550                 555                 560

Gly Gly Ser Gly Asp Thr Gly Arg Pro Phe Val Glu Met Tyr Ser Glu
                565                 570                 575

Ile Pro Glu Ile Ile His Met Thr Glu Gly Arg Glu Leu Val Ile Pro
            580                 585                 590

Cys Arg Val Thr Ser Pro Asn Ile Thr Val Thr Leu Lys Lys Phe Pro
        595                 600                 605

Leu Asp Thr Leu Ile Pro Asp Gly Lys Arg Ile Ile Trp Asp Ser Arg
    610                 615                 620

Lys Gly Phe Ile Ile Ser Asn Ala Thr Tyr Lys Glu Ile Gly Leu Leu
625                 630                 635                 640

Thr Cys Glu Ala Thr Val Asn Gly His Leu Tyr Lys Thr Asn Tyr Leu
                645                 650                 655

Thr His Arg Gln Thr Asn Thr Ile Ile Asp Val Val Leu Ser Pro Ser
            660                 665                 670

His Gly Ile Glu Leu Ser Val Gly Glu Lys Leu Val Leu Asn Cys Thr
        675                 680                 685

Ala Arg Thr Glu Leu Asn Val Gly Ile Asp Phe Asn Trp Glu Tyr Pro
    690                 695                 700

Ser Ser Lys His Gln His Lys Lys Leu Val Asn Arg Asp Leu Lys Thr
705                 710                 715                 720

Gln Ser Gly Ser Glu Met Lys Lys Phe Leu Ser Thr Leu Thr Ile Asp
                725                 730                 735

Gly Val Thr Arg Ser Asp Gln Gly Leu Tyr Thr Cys Ala Ala Ser Ser
            740                 745                 750
```

```
Gly Leu Met Thr Lys Lys Asn Ser Thr Phe Val Arg Val His Glu Lys
        755                 760                 765
```

FUSION PROTEIN COMPRISING A LIGAND BINDING DOMAIN OF VEGF AND PDGF

CROSS REFERENCE TO RELATED APPLICATION

This application is a Section 371 of International Application No. PCT/US2016/021762, filed Mar. 10, 2016, which was published in the English Language on Sep. 15, 2016 under International Publication No. WO 2016/145189 A1, which claims priority under 35 U.S.C. § 119(e) to U.S. Provisional Application No. 62/131,261, filed Mar. 11, 2015, and the disclosures of which are herein incorporated by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "688947-3WO_ST25", creation date of Mar. 3, 2016, and having a size of about 88.9 k bytes. The sequence listing submitted via EFS-Web is part of the specification and is herein incorporated by reference in its entirety.

FIELD OF THE INVENTION

The invention relates to fusion proteins comprising a PDGF binding portion, a VEGF binding portion, and an Fc antibody region, nucleic acids and expression vectors encoding the fusion proteins, recombinant cells thereof, and compositions comprising the fusion proteins. Methods of using the fusion proteins to inhibit PDGF and VEGF functions are also provided.

BACKGROUND OF THE INVENTION

Angiogenesis, the formation of new blood vessels from pre-existing blood vessels, is a normal and vital process involved in fetal development and tissue repair. Angiogenesis is highly regulated by both angiogenic and anti-angiogenic factors, and it involves endothelial cell migration and proliferation, vessel maturation and remodeling, and degradation of the extracellular matrix. Although it is an important process in normal growth and development, angiogenesis also plays a key role in tumor growth, ischemia and inflammation.

During rapid uncontrolled ocular angiogenesis, vascular permeability is increased, leading to vascular fragility and leakiness that results in hemorrhage and accumulation of fluids and protein exudates, and ultimately resulting in either vascular insufficiency or vascular overgrowth. Ocular angiogenesis can occur in a spectrum of ocular disorders such as age-related macular degeneration (AMD), proliferative diabetic neuropathy (PDR), and corneal neovascularization. Both AMD and PDR can result in impairment of the structure and function of retinal neurons, ultimately causing vision loss. If left untreated, the abnormal blood vessels can lead to fibrous scarring, causing irreversible damage to retinal function that can eventually result in blindness (Zhang and Ma, Prog Retin Eye Res. 2007 January; 26(1): 1-37). Corneal neovascularization can similarly lead to a reduction in cornea transparency and vision loss.

Vascular endothelial growth factor (VEGF) plays an important role in angiogenesis. The human VEGF family contains 6 members: VEGF-A VEGF-B, VEGF-C, VEGF-D, VEGF-E and placental growth factor (PlGF). In addition, multiple isoforms of VEGF-A, VEGF-B and PlGF are generated through alternative RNA splicing (Sullivan and Brekken, MAbs. 2010 March-April; 2(2):165-75). VEGF-A is the prototypic member of the family and is the most well characterized. VEGF-A has been shown to serve as a mitogenic factor to endothelial cells, promote endothelial cell survival and proliferation, induce cell migration and increase microvascular permeability. The VEGF family of proteins activate the VEGF signaling pathway by binding to the extracellular region of cell surface VEGF receptors (VEGFRs) to activate the VEGF signaling pathway.

There are three types of VEGFR proteins: VEGFR1, VEGFR2, and VEGFR3, and each contains an extracellular region comprising seven immunoglobulin (Ig)-like domains. The extracellular regions of VEGFRs bind to different VEGF proteins. For example, VEGFR-1 (Flt-1) binds to VEGF-A, VEGF-B, and PlGF, and can function as a decoy receptor for VEGFs or as a regulator of VEGFR-2. VEGFR-2 (KDR/Flk-1) binds all VEGF isoforms and is the predominant mediator of VEGF-induced angiogenesis signaling. VEGFR-3 (Flt-4) binds VEGF-C and VEGF-D, but not VEGF-A, and functions as a mediator of lymphangiogenesis.

The high molecular weight variants $VEGF_{206}$ and $VEGF_{189K}$ are tightly bound to the extracellular membrane and do not interact with the VEGF receptors. While $VEGF_{165}$ is the predominant soluble variant, $VEGF_{121}$ and $VEGF_{145}$ are also soluble variants that bind to VEGFR1 and VEGFR2 receptors, as does the degradation product $VEGF_{110}$ (Bhisitkuk, Br J Ophthalmol. 2006 December; 90(12):1542-7).

Blocking VEGF activity with antibodies, soluble VEGF receptors, or inhibitors of VEGF tyrosine kinase activity are strategies that have been used to treat angiogenic-type disorders, such as AMD. Although anti-VEGF therapy generally stabilizes or improves visual function, it has been reported that sub-retinal scarring, or fibrosis, develops in approximately half of all treated eyes within two years of anti-VEGF treatment (Daniel et al., Ophthalmology. 2014 March; 121(3):656-66). In addition, targeting only VEGF prevents the formation of new blood vesicles, but it has no effect on newly-established blood vessels.

Recent data suggests that pericytes may play a role in anti-VEGF resistance, stabilization of new vessels, and scarring. Pericytes interact with endothelial cells and contribute to the establishment of the blood-retinal barrier. Importantly, pericytes provide survival signals to neovascular endothelial cells, making them resistant to VEGF depletion therapy (Benjamin et al., Development. 1998 May; 125(9):1591-8; Patel, Retina. 2009 June; 29(6 Suppl): S45-8). Platelet-derived growth factor (PDGF) controls pericytes, driving their recruitment, proliferation and survival, and regulating the maturation of new vessels.

The human PDGF family contains four members: PDGF-A, PDGF-B, PDGF-C and PDGF-D. The four PDGF proteins form either homo- or heterodimers (for example, PDGF-AA, PDGF-AB, PDGF-BB, PDGF-CC and PDGF-DD), and they are inactive in their monomeric forms. The dimeric proteins bind to the extracellular region of cell surface PDGF receptors (PDGFRs) to activate the PDGF signaling pathway.

There are two types of PDGF receptors, PDGFR-α and PDGFR-β that form homo- or heterodimers (for example, PDGFR-αα, PDGFR-ββ and PDGFR-αβ) and contain extracellular regions comprising five Ig-like domains. The ligand-binding sites of the receptors are located to the first three Ig-like domains (D1 to D3).

The extracellular regions of the PDGFR dimers bind to different PDGF proteins. For example, PDGFR-αα specifically interacts with PDGF-AA, PDGF-AB, PDGF-BB and PDGF-CC. PDGFR-αβ specifically interacts with PDGF-AB, PDGF-BB, PDGF-CC and PDGF-DD. PDGFR-ββ specifically interacts with PDGF-BB, and PDGF-DD. PDGF-BB, the only PDGF that can bind to all three receptor dimer forms with high affinity, has been shown to be able to induce pericytes proliferation and migration both in vitro and in vivo. An extracellular region consisting of all five Ig-like domains of PDGFR-β (D1 to D5) was previously shown to antagonize responses stimulated by PDGF-B (Duan et al., J Biol Chem. 1991 Jan. 5; 266(1):413-8; Ueno et al., Science. 1991 May 10; 252(5007):844-8). Studies using PDGFRβ-Fc chimeric proteins demonstrated that D1 to D3 of human PDGFR-β are sufficient for high-affinity PDGF-B ligand binding (Heidaran et al., FASEB J. 1995 January; 9(1):140-5; Lokker et al., J Biol Chem. 1997 Dec. 26; 272(52):33037-44). Additionally, pre-dimerization of D1 to D3 of PDGFR-β fused to glutathione S-transferase (GST) improved binding affinity to PDGF-BB ligand compared to recombinant PDGFR-β D1-D3 protein (Leppanen et al., Biochemistry. 2000 Mar. 7; 39(9):2370-5).

While the current anti-VEGF therapies are highly effective, intensive patient monitoring and frequent treatment are required to achieve optimal results. In addition, because these agents target symptoms of the disease and not the underlying cause, treatment must continue indefinitely. With suboptimal treatment, existing choroidal neovascular lesions (CNVs) will continue to grow and eventually mature into fibrotic scars leading to irreversible vision loss (Martin et al., Ophthalmology 2012; 119:1388-1398; Bloch et al., Am J Ophthalmol. 2013 July; 156(1):116-124; Daniel et al., Ophthalmology. 2014 March; 121(3):656-66). Agents that are able to block neovascularization and cause involution of the immature vasculature within the neovascular choroidal lesions have the potential to eliminate the source of the vascular leak and fibrosis, reducing or eliminating the need for intensive patient monitoring and continuous treatment.

Recently, a fusion protein comprising, from N-terminus to C-terminus, an extracellular portion of a PDGF receptor, an extracellular portion of a VEGF receptor, and a multimerization domain has been described (U.S. Patent Application Publication No. 2014/0315804). The fusion protein binds both PDGF and VEGF and inhibits their activities.

Despite the progress described in the art of dual inhibitors of PDGF and VEGF, there is a need in the art for improved formulations and treatments of angiogenic-type disorders.

BRIEF SUMMARY OF THE INVENTION

The invention satisfies this need by providing novel fusion proteins that simultaneously bind to both VEGF and PDGF, targeting both signaling pathways at the same time. The fusion proteins have been generated by fusing extracellular ligand binding domains derived from VEGF and PDGF receptors to a half-life prolonging Fc domain from IgG1. In specific embodiments of the invention, all of the components of the fusion proteins are of human origin and are therefore expected to be useful as non-immunogenic therapeutics in humans. The fusion proteins are able to inhibit both VEGF- and PDGF-dependent cell growth in vitro, and they are able to reduce VEGF-induced retinal leakiness in an animal model.

There is increasing evidence that angiogenesis can occur in the absence of VEGF signaling, and that pericytes supply VEGF and other cell survival factors to the proliferating endothelial cells, conferring anti-VEGF resistance (Reinmuth et al., FASEB J. 2001 May; 15(7):1239-41). A pericyte origin has also been suggested for myofibroblasts in scarring tissue and tumors. The PDGF signaling pathway is responsible for pericyte recruitment, survival and maturation (Andrae et al., Genes Dev. 2008 May 15; 22(10):1276-312). Inhibition of PDGF receptor signaling by antibodies was shown to enhance the therapeutic effect of anti-VEGF treatment in multiple mouse models of ocular neovascularization (Jo et al., Am J Pathol. 2006 June; 168(6):2036-53). A large phase 2 clinical trial of the anti-PDGF agent E10030 in combination with an anti-VEGF agent showed superior results over anti-VEGF monotherapy (Dugel, Retina Today, March 2013, 65-71). Thus, the fusion proteins of the invention are efficacious in treating angiogenic-type disorders, such as AMD and cancer. An additional benefit of the fusion proteins is that there is no need to inject two separate compositions, i.e. of an anti-PDGF agent and an anti-VEGF agent. Instead, a single composition comprising a fusion protein of both agents allows for a single injection, thereby decreasing the risk to patients for infections and injection trauma.

In one general aspect, the invention relates to a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a); and wherein the fusion protein is capable of binding to a VEGF-A molecule and a PDGF-BB molecule and inhibiting the activity of the VEGFR1, VEGFR2 and the activity of the PDGFR.

In an embodiment of the invention, the extracellular ligand binding domain of a VEGF receptor is capable of binding to a VEGF ligand, and comprises one or more of Ig-like domains D1-D7 of one or more VEGF receptors. Preferably, the extracellular ligand binding domain of the VEGF receptor comprises an Ig-like domain D2 of a first VEGF receptor and an Ig-like domain D3 of a second VEGF receptor, wherein the first and second VEGF receptors are the same or different VEGF receptors. In one embodiment, the extracellular ligand binding domain of the VEGF receptor comprises an Ig-like domain D2 of a VEGFR1 and an Ig-like domain D3 of a VEGFR2. In another embodiment, the extracellular ligand binding domain of the VEGF receptor comprises an amino acid sequence having at least 90% sequence identity to SEQ ID NO: 7. More preferably, the extracellular ligand binding domain of the VEGF receptor comprises the amino acid sequence selected from the group consisting of SEQ ID NOs: 7 and 10.

In an embodiment of the invention, the extracellular ligand binding domain of a PDGF receptor is capable of binding to a PDGF ligand and comprises one or more of Ig-like domains D1-D5 of one or more PDGF receptors. Preferably, the extracellular ligand binding domain of the PDGF receptor comprises Ig-like domains D1-D3 of one or more PDGF receptors. In one embodiment, the extracellular ligand binding domain of the PDGF receptor comprises an amino acid sequence having at least 90% sequence identity to SEQ ID NO: 2. More preferably, the extracellular ligand binding domain of the PDGF receptor present comprises the amino acid sequence selected from the group consisting of SEQ ID NOs: 2 and 5.

In an embodiment of the invention, the Fc region of the antibody comprises a CH2 and a CH3 region of IgG1. Preferably, the Fc region of the antibody comprises an amino acid sequence having at least 90% sequence identity to SEQ ID NO: 12. More preferably, the Fc region of the antibody comprises the amino acid sequence selected from the group consisting of SEQ ID NOs: 12 and 15.

In a preferred embodiment of the invention, the fusion protein comprises (a) an Ig-like domain D2 of a VEGFR1 and an Ig-like domain D3 of a VEGFR2, (b) an Fc region of the antibody comprises a CH2 and a CH3 region of IgG1, and (c) an Ig-like domains D1 to D3 of a PDGFRβ, wherein the fusion protein is arranged from N-terminus to C-terminus in an order selected from the group consisting of (a)-(b)-(c) and (c)-(b)-(a), more preferably in an order of (c)-(b)-(a).

In an embodiment of the invention, the fusion protein further comprises a linker peptide between the Fc region and the first or second peptide at the C-terminus of the fusion protein, and optionally a second linker peptide between the second or first peptide at the N-terminus of the fusion protein and the Fc region.

In an embodiment of the invention, the fusion protein further comprises a signal peptide operably linked to the N-terminus of the fusion protein.

In another general aspect, the invention relates to an isolated nucleic acid molecule encoding a fusion protein of the invention.

In another general aspect, the invention relates to an expression vector comprising a nucleic acid molecule encoding a fusion protein of the invention.

In another general aspect, the invention relates to a recombinant host cell comprising a nucleic acid molecule encoding a fusion protein of the invention.

In another general aspect, the invention relates to a method of obtaining a fusion protein of the invention. The method comprises: (1) culturing a host cell comprising a nucleic acid molecule encoding the fusion protein under a condition that the fusion protein is produced; and (2) recovering the fusion protein produced by the host cell.

In another general aspect, the invention relates to a pharmaceutical composition comprising a fusion protein of the invention and a pharmaceutically acceptable carrier.

In another general aspect, the invention relates to a pharmaceutical composition comprising a nucleic acid molecule encoding a fusion protein of the invention and a pharmaceutically acceptable carrier.

In another general aspect, the invention relates to a method of reducing the activity of the VEGFR and the activity of the PDGFR, the method comprising administering to a subject in need thereof an effective amount of a fusion protein of the invention.

In another general aspect, the invention relates to a method of treating or preventing a clinical condition selected from the group consisting of tissue vascularization, vascular permeability, edema and inflammation, the method comprising administering to a subject in need thereof an effective amount of a fusion protein according to an embodiment of the invention.

In another general aspect, the invention relates to a method of treating or preventing a clinical condition selected from the group consisting of choroidal neovascularization (CNV), wet age-related macular degeneration (AMD) and geographic atrophy, the method comprising administering to a subject in need thereof an effective amount of the fusion protein of according to embodiments of the invention.

In an embodiment of the invention, the fusion protein is administered as an isolated protein or as an expression vector.

In an embodiment of the invention, the clinical condition is selected from the group consisting of brain edema, stroke, cancer, psoriasis, arthritis, asthma, generalized edema associated with burns, ascites and pleural effusion associated with tumors, inflammation or trauma, chronic airway inflammation, capillary leak syndrome, sepsis, kidney disease associated with increased leakage of protein, rheumatoid arthritis, inflammatory arthritis, osteoarthritis, atherosclerosis, psoriasis, ocular inflammation and/or ocular angiogenesis, including aged-related macular degeneration, proliferative and nonproliferative diabetic retinopathy, corneal neovascularization, rubeosis iridis and neovascular glaucoma.

In another general aspect, the invention relates to a dimeric antagonist for PDGF and VEGF comprising a fusion protein of the invention.

In another general aspect, the invention relates to a protein conjugate comprising a fusion protein of the invention bound to at least one ligand selected from the group consisting of PDGF-BB and VEGF-A.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings.

DETAILED DESCRIPTION OF THE INVENTION

Figure 1:
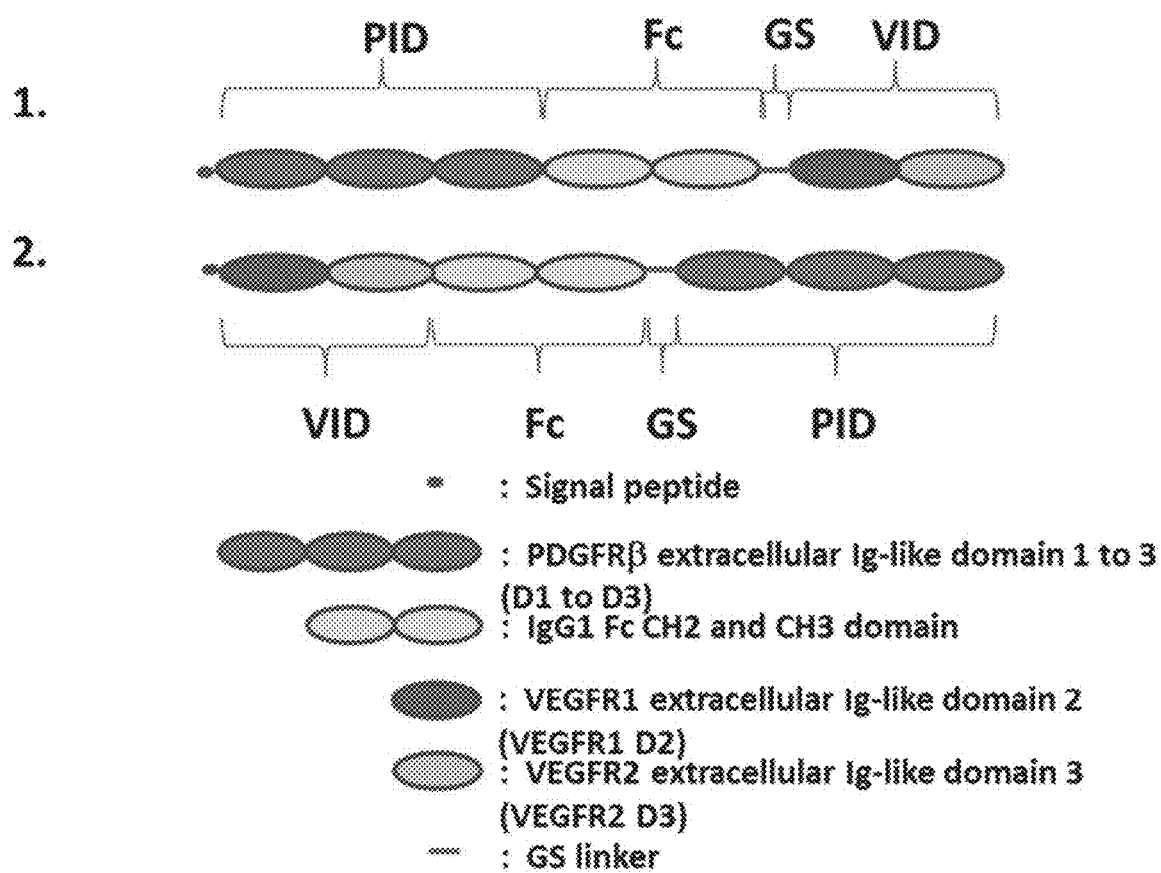
FIG. 1 shows the structural design of exemplary bi-functional fusion proteins according to embodiments of the invention, Fusion Protein 2 (top) and Fusion Protein 1 (bottom), designed to inhibit both PDGF and VEGF pathways simultaneously: PDGFR extracellular Ig-like domain (PID) represents the extracellular Ig-like domains D1 to D3 of PDGFRβ; Fc represents IgG1 CH2 and CH3 domains; VEGFR extracellular Ig-like domain (VID) represents the extracellular Ig-like domain D2 of VEGFR1 and the extracellular Ig-like domain D3 of VEGFR2.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

The invention relates to a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a); and wherein the fusion protein is capable of binding to a VEGF-A and a PDGF-BB and inhibiting the activity of the VEGFR1, VEGFR2 and the activity of the PDGFR.

It is surprisingly discovered during the present invention that the orientation of the extracellular ligand binding domains of the VEGF and PDGF receptors with respect to the other components in the fusion protein, such as the antibody Fc region, has an impact on the binding affinity of the fusion protein for the VEGF and PDGF ligands. A fusion protein according to an embodiment of the invention, has optimized affinity of the fusion protein for both of the ligands and may have an increased efficacy of the fusion proteins.

As used herein, the phrase "fusion protein" refers to a protein having two or more portions covalently linked together, where each of the portions is derived from different proteins.

As used herein, the term "VEGF" refers to any vascular endothelial growth factor protein that regulates the VEGF signaling pathway. Thus, the term VEGF can refer to VEGF-A VEGF-B, VEGF-C, VEGF-D, VEGF-E, PlGF, or isoforms thereof.

As used herein, the terms "VEGF receptor" and "VEGFR" refer to any receptor that binds to a VEGF ligand. Thus, the term VEGF receptor can refer to a VEGFR1, VEGFR2 or VEGFR3.

As used herein, the phrase "extracellular ligand binding domain" refers to any region of a receptor protein that is located on the outside of the cell and is able to bind to its ligand.

Accordingly, the extracellular ligand binding domain of the VEGF receptor that is present in the fusion protein of the invention can be from any VEGFR, including, but not limited to, VEGFR1, VEGFR2, and VEGFR3. The seven extracellular IgG-like domains of the VEGFR proteins are numbered 1, 2, 3, 4, 5, 6 and 7, from the N- to C-terminus of the extracellular region, and are alternatively referred to as D1, D2, D3, D4, D5, D6 and D7. The extracellular ligand binding domain of a VEGFR that is present in the fusion protein of the invention can comprise one or more of any of the seven IgG-like domains from the extracellular region of one or more of any VEGFR protein. For example, the extracellular ligand binding domain of a VEGF receptor that is present in the fusion protein of the invention can be one or more of D1, D2, D3, D4, D5, D6, or D7 from one or more of VEGFR1, VEGFR2, or VEGFR3.

In a preferred embodiment, the extracellular ligand binding domain of the VEGF receptor that is present in the fusion protein comprises an Ig-like domain D2 of a VEGFR1 and an Ig-like domain D3 of a VEGFR2. Preferably, the extracellular ligand binding domains of the VEGFR comprises one or more mutations that increases its binding to a VEGF. In a more preferred embodiment, the extracellular ligand binding domain of the VEGF receptor that is present in the fusion protein comprises an amino acid sequence having at least 90% identity to SEQ ID NO: 7. In an even more preferred embodiment, the extracellular ligand binding domain of the VEGF receptor that is present in the fusion protein comprises the amino acid sequence selected from the group consisting of SEQ ID NOs: 7 and 10.

The extracellular ligand binding domain of the VEGF receptor that is present in the fusion protein of the invention can be from any animal, such as a human or another suitable mammal, such as a mouse, rabbit, rat, pig, dog, or a primate. In a preferred embodiment, the VEGFR is from a human.

As used herein, the term "PDGF" refers to any plasma-derived growth factor protein that regulates the PDGF signaling pathway. Thus, the term PDGF can refer to PDGF-A, PDGF-B, PDGF-C or PDGF-D.

As used herein, the terms "PDGF receptor" and "PDGFR" refer to any receptor that binds to a PDGF ligand.

The extracellular ligand binding domain of the PDGF receptor that is present in the fusion protein of the invention can be from any PDGFR, including, but not limited to, PDGFR-α and PDGFR-β. The five extracellular IgG-like domains of the PDGFR proteins are numbered 1, 2, 3, 4 and 5, from the N- to C-terminus of the extracellular region and are alternatively referred to as D1, D2, D3, D4 and D5. The extracellular ligand binding domain of a PDGFR that is present in the fusion protein of the invention can be one or more of any of the five IgG-like domains from the extracellular region of one or more of any PDGFR protein. For example, the extracellular ligand binding domain of a PDGF receptor that is present in the fusion protein of the invention can be one or more of D1, D2, D3, D4, or D5 from one or more of PDGFR-α or PDGFR-β.

In a preferred embodiment, the extracellular ligand binding domain of the PDGF receptor that is present in the fusion protein comprises Ig-like domains D1 to D3 of a PDGFRβ. Preferably, the extracellular ligand binding domains of the PDGFR comprises one or more mutations that increases its binding to a PDGF. In a more preferred embodiment, the extracellular ligand binding domain of the PDGF receptor that is present in the fusion protein comprises an amino acid sequence having at least 90% identity to SEQ ID NO: 2. In an even more preferred embodiment, the extracellular ligand binding domain of the PDGF receptor that is present in the fusion protein comprises the amino acid sequence selected from the group consisting of SEQ ID NOs: 2 and 5.

The extracellular ligand binding domain of the PDGF receptor that is present in the fusion protein of the invention can be from any animal, such as a human or another suitable mammal, such as a mouse, rabbit, rat, pig, dog, or a primate. In a preferred embodiment, the PDGFR is from a human.

As used herein, the term "Fc region" of an antibody refers to the "fragment, crystallizable" region of an antibody that is composed of two heavy chains that comprise two or three constant domains, depending on the class of the antibody. The term is used to define a C-terminal region of an immunoglobulin heavy chain that contains at least a portion of the constant region. The term includes both native and variant Fc regions. The Fc region of an antibody can serve as a multimerization domain, which is a domain that promotes the association of subunits into multimers, such as dimers, trimers, tetramers, etc. Preferably, the Fc region comprises one or more mutations that promote the association of subunits into multimers.

The Fc region of an antibody that is present in the fusion protein of the invention can be from any isotype (e.g., IgG, IgM, IgA, IgD or IgE), any subclass (e.g., IgG1, IgG2, IgG3, IgG4, IgA1, IgA2, etc.), any allotype, or any engineered mutant, such as knob and hole Fc fragments. In a preferred embodiment, the Fc region of an antibody that is present in the fusion protein of the invention comprises a CH2 and a CH3 region of IgG1. In a more preferred embodiment, the Fc region of an antibody that is present in the fusion protein of the invention comprises an amino acid sequence having at least 90% identity to SEQ ID NO: 12. In an even more preferred embodiment, the Fc region of an antibody that is present in the fusion protein of the invention comprises the amino acid sequence selected from the group consisting of SEQ ID NOs: 12 and 15.

The Fc region of an antibody that is present in the fusion protein of the invention can be from any animal, such as a human or another suitable mammal, such as a mouse, rabbit, rat, pig, dog, or a primate. In a preferred embodiment, the Fc region is from a human antibody.

According to embodiments of the invention, components of the fusion protein can be linked by a linking moiety such as a peptide linker. Preferably, the linker increases flexibility of the fusion protein components, helps insure correct folding, minimizes steric hindrance and does not interfere significantly with the structure of each functional component within the fusion protein. In some embodiments, the peptide linker comprises 2 to 20 amino acids. In some embodiments, the peptide linker comprises 2, 3, 4, 5, 6, 7, 8, 9, 10, 11, 12, 13, 14, 15, 16, 17, 18, 19, or 20 amino acids. Preferably, the fusion protein comprises a first linker peptide between the Fc region and the first or second peptide at the C-terminus of the fusion protein, and optionally a second linker peptide between the second or first peptide at the N-terminus of the fusion protein and the Fc region. In preferred embodiments of the invention, the first linker peptide comprises one or more amino acid sequences selected from the group consisting of SEQ ID NOs: 20, 22, 24, 26, 28, 30 and 32, and the second linker peptide comprises an amino acid sequence of SEQ ID NO: 18.

According to embodiments of the invention, the fusion protein further comprises a signal peptide linked to N-terminus of the fusion protein to ensure the secretion of the fusion protein from the cell. Any signal peptide that is recognized and processed by host cells can be used. In preferred embodiments, the signal peptide includes but is not limited to an amino acid sequence of SEQ ID NOs: 34 or 36.

In a preferred embodiment, the fusion protein of the invention comprises an amino acid sequence having at least 90% identity to SEQ ID NO: 38 or at least 90% identity to SEQ ID NO: 40, preferably at least 90% identity to amino acids number 20 to 766 of SEQ ID NO: 42, amino acids number 21 to 769 of SEQ ID NO: 44 or amino acids number 20 to 768 of SEQ ID NO: 50. The fusion protein can include one or more mutations or single nucleotide polymorphisms (SNPs) in the VEGF receptor domains and/or PDGF receptor domains. There can also include one or more mutations or SNPs that occur at the Fc region of an antibody in accordance with embodiments of the invention.

In a more preferred embodiment, the fusion protein of the invention comprises an amino acid sequence selected from the group consisting of SEQ ID NO: 38, SEQ ID NO: 40, amino acids 20-766 of SEQ ID NO: 42, and amino acids 21-769 of SEQ ID NO:44 and amino acids 20-768 of SEQ ID NO: 50.

In a general aspect, the fusion protein of the invention binds to a VEGF and a PDGF and inhibits the activity of the VEGF and the PDGF receptors. As used herein, the term "binds to" refers to the binding of an extracellular domain of a receptor protein to a ligand that results in one or more of inhibiting, blocking, neutralizing, reducing, abrogating or interfering with the ligand's activities. In certain embodiments, the extracellular domain of a VEGF or a PDGF receptor protein inhibits ligand activities by binding to the ligand, i.e., VEGF or PDGF, respectively, and sequestering the ligand from binding to other molecules, such as other VEGF receptors and PDGF receptors. In certain other embodiments, the extracellular domain of a VEGF or a PDGF receptor protein inhibits ligand activities by binding to the ligand, i.e., VEGF or PDGF, respectively, and preventing the ligand from triggering downstream signaling events in the cells.

As used herein, the term "inhibition" or "inhibit" in the context of ligand activity as used herein refers to a property of an extracellular domain of a receptor protein that reduces the activity of the ligand as analyzed by various functional assays, including, but not limited to, binding assays, cell growth assays, competitive binding assays, and in vivo assays.

The fusion proteins or components of the fusion protein disclosed herein can be characterized or assessed for biological activities including, but not limited to, affinity to a target binding partner (e.g., a PDGF and/or VEGF family protein), competitive binding (e.g., blocking a PDGF or VEGF from binding to a PDGFR or VEGFR), inhibitory activity (e.g., inhibiting the activation of PDGF or VEGF signaling pathways), inhibition of cell proliferation, inhibition of tumor growth, and inhibition of angiogenesis (e.g., inhibition of choroidal neovascularization). In some embodiments, the fusion proteins or fusion protein components disclosed herein can be assessed for biological activity in vivo or in vitro.

The invention also provides an isolated nucleic acid molecule encoding a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a). According to embodiments of the invention, the nucleic acid molecule encoding the fusion protein can be codon-optimized for expression in a particular type of host cell, such as Chinese hamster ovary cells. According to preferred embodiments of the invention, the nucleic acid molecule encoding the fusion protein comprises a nucleotide sequence selected from the group consisting of SEQ ID NOs: 37, 39, 41, 43 and 49.

According to other embodiments of the invention, the nucleic acid molecule encoding the fusion protein can be in an expression vector. Expression vectors include, but are not limited to, vectors for recombinant protein expression and vectors for delivery of nucleic acids into a subject for expression in a tissue of the subject, such as viral vectors. Examples of viral vectors suitable for use with the invention include, but are not limited to adenoviral vectors, adeno-associated virus vectors, lentiviral vectors, etc. The vector can also be a non-viral vector. Examples of non-viral vectors include, but are not limited to plasmids, bacterial artificial chromosomes, yeast artificial chromosomes, bacteriophages, etc. The vector may include any element to establish a conventional function of an expression vector, for example, a promoter, ribosome binding element, terminator, enhancer, selection marker, or an origin of replication.

According to other embodiments of the invention, the nucleic acid molecule encoding the fusion protein can be codon optimized for improved recombinant expression from a desired host cell using methods known in the art in view of the present disclosure.

The invention also provides a host cell comprising a nucleic acid molecule encoding a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a). Host cells include, but are not limited to, host cells for recombinant protein expression and host cells for delivery of the nucleic acid into a subject for expression in a tissue of the subject. Examples of host cells suitable for use with the invention include, but are not limited to Chinese hamster ovary (CHO) cells, Human Embryonic Kidney 293 (HEK-293), etc.

The invention also provides a method of producing a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a). In a general aspect, the method comprises (1) culturing a host cell comprising a nucleic acid molecule encoding the fusion protein under a condition that the fusion protein is produced; and (2) recovering the fusion protein produced by the host cell. The fusion protein can be purified further using methods known in the art.

In some embodiments, the fusion protein is expressed in host cells and purified therefrom using a combination of one or more standard purification techniques, including, but not limited to, Protein A affinity chromatography, Protein G affinity chromatography, buffer exchange, size exclusion chromatography, ultrafiltration, and dialysis.

The invention also provides a pharmaceutical composition comprising a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a). Compositions of the invention comprise a therapeutically effective amount of the fusion protein.

The term "therapeutically effective amount" means an amount of a therapeutically active compound needed to elicit the desired biological or clinical effect. According to embodiments of the invention, "a therapeutically effective amount" is an amount sufficient to effect beneficial or desired results, including clinical results. A therapeutically effective amount can be administered in one or more administrations. In terms of a disease state, an effective amount is an amount sufficient to ameliorate, stabilize, or delay development of a disease. According to specific embodiments of the invention, a therapeutically effective amount is an amount of a fusion protein needed to treat or prevent a disorder characterized by abnormal angiogenesis, such as a disease characterized by vascular permeability, edema, inflammation, retinopathies, fibrosis or cancer.

In some embodiments, the pharmaceutical composition comprising a fusion protein comprises a fusion protein formulated in a buffer at a protein concentration from about 0.5 to about 100 mg/mL, preferably about 40 to about 80 mg/mL, such as about 40, 50, 60, 70 or 80 mg/mL, most preferably about 40±about 5 mg/mL. In other preferred embodiments, the fusion protein is formulated in a buffer at a protein concentration of more than about 40 mg/mL, preferably about 80±about 10 mg/mL.

In particular embodiments, the buffer is a phosphate buffer with a pH of about 6.5 to 8, more preferably about 7 to 7.5, even more preferably about 7.2. The phosphate buffer comprises about 5 to 20 mM sodium phosphate, such as 5, 10, 15 or 20 mM sodium phosphate, more preferably about 10 mM sodium phosphate; about 20 to 60 mM sodium chloride, more preferably about 40 mM sodium chloride; about 1 to 10% weight-per-volume (w/v) sucrose, more preferably about 5% w/v sucrose; and about 0.01 to 0.05% w/v of a surfactant, more preferably about 0.03% w/v polysorbate 20.

In other particular embodiments, the buffer is a histidine buffer with a pH of about 5 to 8, more preferably about 6 to 7, most preferably about 6.8. The histidine buffer comprises about 10 to 50 mM histidine, such as 10, 20, 30, 40 or 50 mM histidine, more preferably about 25 mM histidine; about 10 to 30 mM sodium chloride, such as 10, 20 or 30 mM sodium chloride, more preferably about 20 mM sodium chloride; about 1 to 10% w/v sucrose, such as 1, 2, 4, 6, 8 or 10% w/v sucrose, more preferably about 6% w/v sucrose; and about 0.01 to 0.05% w/v of a surfactant, more preferably about 0.03% w/v polysorbate 20.

The invention also provides a composition comprising a nucleic acid molecule encoding a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a), preferably in an order of (c)-(b)-(a).

Compositions comprising a nucleic acid molecule encoding a fusion protein of the invention can comprise a delivery vehicle for introduction of the nucleic acid molecule into a cell for expression of the fusion protein. Examples of nucleic acid delivery vehicles include liposomes, biocompatible polymers, including natural polymers and synthetic polymers, lipoproteins, polypeptides, polysaccharides, lipopolysaccharides, artificial viral envelopes, metal particles, and bacteria, viruses, such as baculoviruses, adenoviruses and retroviruses, bacteriophages, cosmids, plasmids, fungal vectors and other recombination vehicles typically used in the art which have been described for expression in a variety of eukaryotic hosts.

The invention also relates to use of the pharmaceutical compositions described herein to treat or prevent a condition, disease or disorder characterized by abnormal angiogenesis, such as a disease characterized by neovascularization, vascular permeability, edema, or inflammation, retinopathies, fibrosis or cancer. According to embodiments of the invention, a method of treating a condition, disease or disorder characterized by abnormal angiogenesis in a subject comprises administering to the subject in need of the treatment a pharmaceutical compositions of the invention. Any of the pharmaceutical compositions described herein can be used in a method of the invention, including pharmaceutical compositions comprising the fusion protein or pharmaceutical compositions comprising a nucleic acid encoding the fusion protein. Preferably, a pharmaceutical composition of the invention is administered to a subject via the vitreous, conjunctiva, tenon, retrobulbar, or sclera for ophthalmology-related diseases, and into blood or tissues for systemic diseases.

As used herein, "subject" means any animal, preferably a mammal, most preferably a human, who will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

A "condition, disease or disorder characterized by abnormal angiogenesis" or an "angiogenic-type disorder" as used herein, shall have the same meaning, and refers to any disorder related to abnormal blood vessel production, including excessive, insufficient, or abnormal angiogenesis. Examples of angiogenic-type disorders that can be treated according to a method of the invention include, but are not limited to, diseases characterized by neovascularization, vascular permeability, edema, or inflammation. These include, but are not limited to, ocular inflammation and/or ocular angiogenesis, including aged-related macular degeneration (such as wet AMD, dry AMD or geographic atrophy), proliferative and nonproliferative diabetic retinopathy, ocular disease characterized by neovascularization (such as corneal neovascularization or choroidal neovascularization), uveitis (such as anterior uveitis or posterior uveitis), retinitis pigmentosa, diabetic retinopathy, rubeosis iridis, neovascular glaucoma, inflammatory disease, rheumatoid arthritis, inflammatory arthritis, osteoarthritis, autoimmune disease, and cancer. In preferred embodiments of the invention, the angiogenic-type disorder to be treated is retinopathies, fibrosis or cancer.

In other embodiments, the angiogenic-type disorder that can be treated according to a method of the invention include, but are not limited to, brain edema, stroke, psoriasis, asthma, generalized edema associated with burns, ascites and pleural effusion associated with tumors, inflammation or trauma, chronic airway inflammation, capillary leak syndrome, sepsis, kidney disease associated with increased leakage of protein.

The terms "treat," "treating," and "treatment" as used herein refer to administering a composition to a subject to achieve a desired therapeutic or clinical outcome in the subject. In one embodiment, the terms "treat," "treating," and "treatment" refer to administering a pharmaceutical composition of the invention to reduce, alleviate or slow the progression or development of an angiogenic-type disorder, such as vascular permeability, edema or inflammation. In yet another embodiment, the terms "treat," "treating," and "treatment" refer to administering a pharmaceutical composition of the invention to inhibit or reduce corneal neovascularization and/or leaky vasculature in the eye. In yet another embodiment, the terms "treat," "treating," and "treatment" refer to administering a pharmaceutical composition of the invention to slow the progression or development of new blood vessels in the cornea (i.e., corneal neovascularization) or site of interest. In particular embodiments of the invention, when used with reference to AMD, the terms "treat," "treating," and "treatment" refer to preventing or reducing VEGF-induced retinal leakiness, and to preventing or reducing ocular scarring and fibrosis related to angiogenesis. In particular embodiments of the invention, when used with reference to cancer, the terms "treat," "treating," and "treatment" refer to reducing the proliferation of, de-differentiation of, or spread of cancerous cells. Treating a tumor according to the present invention includes a reduction in tumor size, a reduction in tumor growth, and a reduction in tumor metastasis. As used herein, the term "tumor" refers to abnormal tissue masses, and includes both benign and malignant masses.

According to embodiments of the invention, a pharmaceutical composition can be administered by any method known to those skilled in the art in view of the present disclosure, such as by topical administration, intravitreous injection, suprachoroidal or subconjunctival injection. In a preferred embodiment, the ophthalmic formulation is intravitreally administered. The pharmaceutical composition can be administered to any part of the eye, and is preferably administered to the vitreous of the eye for the treatment of angiogenic-type disorders. The pharmaceutical composition can be administered to any part of the body, and is preferably administered to the blood or tissue/organ for the treatment of angiogenic-type disorders.

Parameters such as the dosage amount, frequency of administration, and duration of administration of a pharmaceutical composition to a subject according to an embodiment of the invention are not limited in any particular way. The optimum values of such parameters can depend on a variety of factors, such as the subject to be treated, the particular angiogenic-type disease to be treated, the severity of the disease, etc., and one of ordinary skill in the art will be able to determine the optimum values for such parameters in order to achieve the desired therapeutic or clinical outcome. For example, a pharmaceutical composition can be administered once per day, or more than once per day, such as twice, three times, four times, etc. An exemplary and non-limiting dosing regimen comprises administering a pharmaceutical composition intravitreally once for a duration of one month.

In other embodiments, the invention may be administered together with other anti-angiogenic agents, such as anti-hepatocyte growth factor (HGF), anti-HGF receptor (HGFR), anti-fibroblast growth factor (FGF), anti-FGF receptor (FGFR), anti-inflammatory (corticosteroid, non-steroidal anti-inflammatory drugs), immunomodulatory, antibiotic, and anti-cancer agents.

In a general aspect, the invention provides a dimeric antagonist for PDGF and VEGF comprising the fusion protein of the invention. Each fusion protein in the dimer comprises any fusion protein disclosed herein. In one embodiment, the dimeric fusion protein comprises two identical fusion proteins of the invention. In another embodiment, the dimeric fusion protein comprises two different fusion proteins of the invention. In another embodiment, the dimeric fusion protein comprises at least one fusion protein comprising the amino acid sequence selected from the group consisting of SEQ ID NO: 38, SEQ ID NO: 40, amino acids 20-766 of SEQ ID NO: 42, amino acids 21-769 of SEQ ID NO:44 and amino acids 20-768 of SEQ ID NO: 50, or an amino acid sequence having at least 90% identity to the amino acid sequence selected from the group consisting of SEQ ID NOs: 38, SEQ ID NO:40, amino acids 20-766 of SEQ ID NO: 42, amino acids 21-769 of SEQ ID NO:44 and amino acids 20-768 of SEQ ID NO: 50.

In another general aspect, the invention provides a protein conjugate comprising the fusion protein of the invention bound to at least one ligand selected from the group consisting of PDGF and VEGF.

EMBODIMENTS

Embodiment 1 is a fusion protein comprising (a) a first peptide comprising an extracellular ligand binding domain of a VEGF receptor, (b) an Fc region of an antibody, and (c) a second peptide comprising an extracellular ligand binding domain of a PDGF receptor; wherein the fusion protein is arranged from N-terminus to C-terminus in an order selected from the group consisting of (a)-(b)-(c) and (c)-(b)-(a); and wherein the fusion protein is capable of binding to a VEGF and a PDGF and inhibiting the activity of the VEGF and the activity of the PDGF.

Embodiment 2 is a fusion protein according to embodiment 1, wherein the extracellular ligand binding domain of a VEGF receptor is capable of binding to a VEGF ligand and comprises one or more selected from the group consisting of Ig-like domains D1-D7 of a VEGF receptor.

Embodiment 3 is a fusion protein according to embodiment 1, wherein the extracellular ligand binding domain of a PDGF receptor is capable of binding to a PDGF ligand and comprises one or more selected from the group consisting of Ig-like domains D1-D5 of a PDGF receptor.

Embodiment 4 is a fusion protein according to embodiment 1, wherein (a) the extracellular ligand binding domain of the VEGF receptor comprises an Ig-like domain D2 of a first VEGFR, preferably VEGFR1, and an Ig-like domain D3 of a second VEGFR, preferably VEGFR2; (b) the Fc region of the antibody comprises a CH2 and a CH3 region of IgG1; and (c) the extracellular ligand binding domain of the PDGF receptor comprises Ig-like domains D1 to D3 of a PDGFR, preferably PDGFRβ.

Embodiment 5 is a fusion protein according to embodiment 4, wherein: (a) the extracellular ligand binding domain of the VEGF receptor comprises an amino acid sequence having at least 90% identity to SEQ ID NO: 7; (b) the Fc region of the antibody comprises an amino acid sequence having at least 90% identity to SEQ ID NO: 12; and (c) the extracellular ligand binding domain of PDGF receptor comprises an amino acid sequence having at least 90% identity to SEQ ID NO: 2.

Embodiment 6 is a fusion protein according to embodiment 5, wherein: (a) the extracellular ligand binding domain of VEGF receptor comprises the amino acid sequence selected from the group consisting of SEQ ID NOs: 7 and 10; (b) the Fc region of the antibody comprises the amino acid sequence selected from the group consisting of SEQ ID NOs: 12 and 15; and (c) the extracellular ligand binding domain of PDGF receptor comprises the amino acid sequence selected from the group consisting of SEQ ID NOs: 2 and 5.

Embodiment 7 is a fusion protein according to any of embodiments 1 to 6, further comprising a first linker peptide between the Fc region and the first or second peptide at the C-terminus of the fusion protein, and optionally a second linker peptide between the second or first peptide at the N-terminus of the fusion protein and the Fc region.

Embodiment 8 is a fusion protein according to embodiment 7, wherein the first linker peptide comprises one or more amino acid sequences selected from the group consisting of SEQ ID NOs: 20, 22, 24, 26, 28, 30 and 32, and the second linker peptide comprises an amino acid sequence of SEQ ID NO: 18.

Embodiment 9 is a fusion protein according to embodiments 1 to 8, wherein the fusion protein further comprises a signal peptide linked to the N-terminus of the fusion protein.

Embodiment 10 is a fusion protein according to embodiment 9, wherein the signal peptide comprises an amino acid sequence selected from the group consisting of SEQ ID NOs: 34 and 36.

Embodiment 11 is a fusion protein according to any of embodiments 1-10, wherein the fusion protein is arranged from N-terminus to C-terminus in an order of (c)-(b)-(a);

Embodiment 12 is a fusion protein comprising an amino acid sequence having at least 90% identity to SEQ ID NO: 38 or 40 or having at least 90% identity to amino acids 20-766 of SEQ ID NO: 42, amino acids 21-769 of SEQ ID NO: 44 or amino acids 20-768 of SEQ ID NO: 50.

Embodiment 13 is a fusion protein according to embodiment 12, comprising an amino acid sequence selected from the group consisting of SEQ ID NO: 38, SEQ ID NO: 40, amino acids 20-766 of SEQ ID NO: 42, amino acids 21-769 of SEQ ID NO: 44 and amino acids 20-768 of SEQ ID NO: 50.

Embodiment 14 is an isolated nucleic acid molecule encoding the fusion protein of any one of embodiments 1 to 13.

Embodiment 15 is an isolated nucleic acid molecule according to embodiment 14, wherein the fusion protein further comprises a signal peptide linked to the N-terminus of the fusion protein.

Embodiment 16 is an isolated nucleic acid molecule according to embodiment 15, wherein the signal peptide comprises an amino acid sequence selected from the group consisting of SEQ ID NOs: 34 and 36.

Embodiment 17 is an isolated nucleic acid molecule according to any of embodiments 14-16, wherein the nucleic acid molecule comprises a nucleotide sequence selected from the group consisting of SEQ ID NOs: 37, 39, 41, 43 and 49.

Embodiment 18 is an expression vector comprising a nucleic acid molecule encoding the fusion protein of any one of embodiments 1 to 13.

Embodiment 19 is an expression vector according to embodiment 18, wherein the nucleic acid molecule comprises a nucleotide sequence selected from the group consisting of SEQ ID NOs: 37, 39, 41, 43 and 49.

Embodiment 20 is a host cell comprising a nucleic acid molecule encoding the fusion protein of any one of embodiments 1 to 13.

Embodiment 21 is a method of producing the fusion protein of any one of embodiments 1 to 13, comprising: (1) culturing a host cell comprising a nucleic acid molecule encoding the fusion protein of any one of embodiments 1 to 13 under a condition that the fusion protein is produced; and (2) recovering the fusion protein produced by the host cell.

Embodiment 22 is a pharmaceutical composition comprising the fusion protein of any one of embodiments 1 to 13 and a pharmaceutically acceptable carrier.

Embodiment 23 is a pharmaceutical composition according to embodiment 22, wherein the composition comprises 40 to 80 mg/mL of the fusion protein formulated in a buffer comprising about 5-100 mM histidine, about 1-10% w/v sucrose, and about 0.005-0.1% w/v polysorbate 20, at a pH of about 6.3 to 7.3.

Embodiment 24 is a pharmaceutical composition comprising a nucleic acid molecule encoding the fusion protein of any one of embodiments 1 to 13 and a pharmaceutically acceptable carrier such as a lipid carrier (e.g., Lipofectamine), chemicals (e.g., polyethyleneimine), or an electroporation buffer.

Embodiment 25 is a pharmaceutical composition according to embodiment 24, wherein the composition comprises plasmids with expression cassette and a pharmaceutically acceptable carrier such as a lipid carrier (e.g., Lipofectamine), chemicals (e.g., polyethyleneimine), or an electroporation buffer.

Embodiment 26 is a method of treating or preventing a clinical condition selected from the group consisting of neovascularization, vascular permeability, edema and inflammation, the method comprising administering to a subject in need thereof an effective amount of the fusion protein of any one of embodiments 1 to 13, or the pharmaceutical composition of any of Embodiments 22-25.

Embodiment 27 is the method of embodiment 26, wherein the fusion protein is administered as an isolated protein in the pharmaceutical composition of any of Embodiments 22-23.

Embodiment 28 is the method of embodiment 26, wherein the fusion protein is administered in the pharmaceutical composition of any of Embodiments 24 and 25.

Embodiment 29 is a method of any one of embodiments 26 to 28, wherein the clinical condition is selected from the group consisting of brain edema, stroke, cancer, psoriasis, arthritis, asthma, generalized edema associated with burns, ascites and pleural effusion associated with tumors, inflammation or trauma, chronic airway inflammation, capillary leak syndrome, sepsis, kidney disease associated with increased leakage of protein, ocular inflammation and/or ocular angiogenesis, including aged-related macular degeneration, diabetic retinopathy, uveitis and corneal neovascularization.

Embodiment 30 is a method of treating or preventing a clinical condition selected from the group consisting of choroidal neovascularization (CNV), wet age-related macular degeneration (AMD) and geographic atrophy, the method comprising administering to a subject in need thereof an effective amount of the fusion protein of any one of embodiments 1 to 13, or the pharmaceutical composition of any of Embodiments 22-25.

Embodiment 31 is the method of embodiment 30, wherein the fusion protein is administered as an isolated protein in the pharmaceutical composition of any of Embodiments 22-23.

Embodiment 32 is the method of embodiment 30, wherein the fusion protein is administered in the pharmaceutical composition of any of Embodiments 24 and 25.

Embodiment 33 is a dimeric antagonist for PDGF and VEGF comprising the fusion protein of any one of embodiments 1 to 13.

Embodiment 34 is a protein conjugate comprising the fusion protein of any one of embodiments 1 to 13 bound to at least one ligand selected from the group consisting of PDGF and VEGF.

EXAMPLES

The following examples of the invention are to further illustrate the nature of the invention. It should be understood that the following examples do not limit the invention and that the scope of the invention is to be determined by the appended claims.

Example 1—Generation, Expression and Purification and Analysis of Fusion Proteins A PDGFR extracellular Ig-like domain (PID) (SEQ ID NO: 2) (Heidaran et al., FASEB J. 1995 January; 9(1):140-5; Lokker et al., J Biol Chem. 1997 Dec. 26; 272(52):33037-44) having the Ig-like domains D1-D3 of PDGFRβ, and a VEGFR extracellular Ig-like domain (VID) (SEQ ID NO: 7) having the Ig-like domain D2 of VEGFR-1 (VEGFR-1_D2) and the Ig-like domain D3 of VEGFR-2 (VEGFR-2 D3) (Holash, J., et al, PNAS, 2002, 99 (17): 11393-98) were incorporated into fusion proteins. A short flexible peptide linker, GGGGGS (SEQ ID NO: 20) was placed between the C-terminus of the Fc region (SEQ ID NO: 12) and the N-terminal module (either PID or VID) to ensure correct folding and minimize steric hindrance. A signal peptide (e.g., SEQ ID NO: 34 or SEQ ID NO: 36) was included to ensure that the produced Fusion Protein 2 or Fusion Protein 1 would be secreted. The Fc region of human IgG1 was incorporated to cause dimerization of the fusion protein, mimicking in vivo receptor dimerization, and to allow for easy purification of the expressed fusion proteins.

Figure 2A:
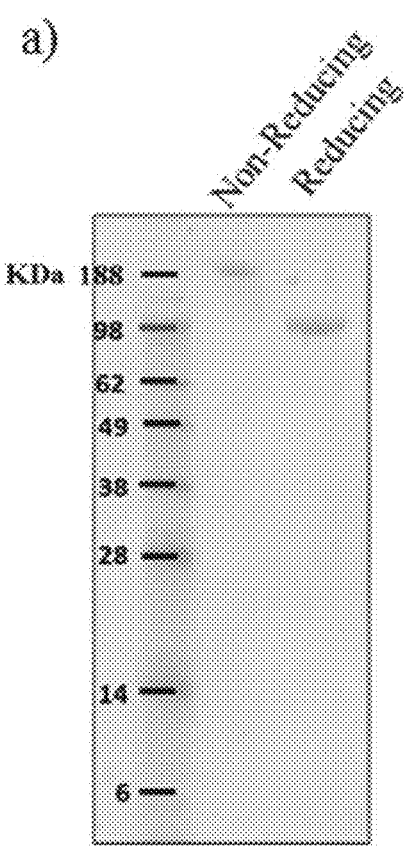
FIG. 2A and FIG. 2B show SDS-PAGE gel analysis of the purified bi-functional Fc Fusion Proteins 1 and 2, respectively.
Figure 2B:
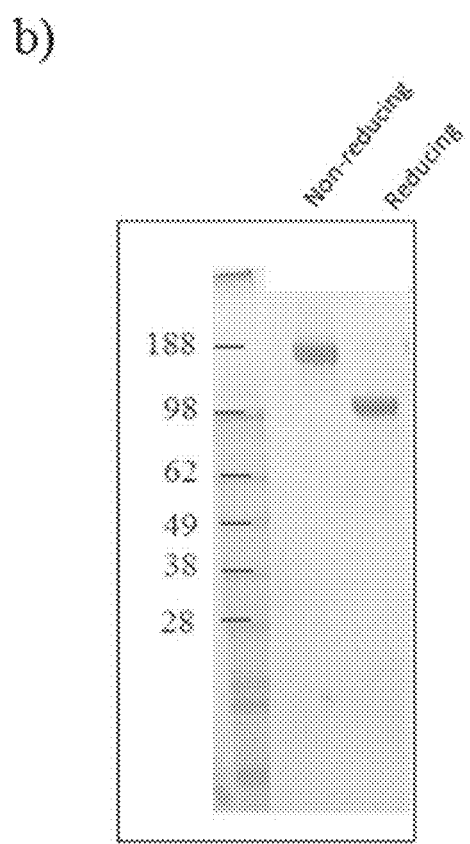
Figure 2C:
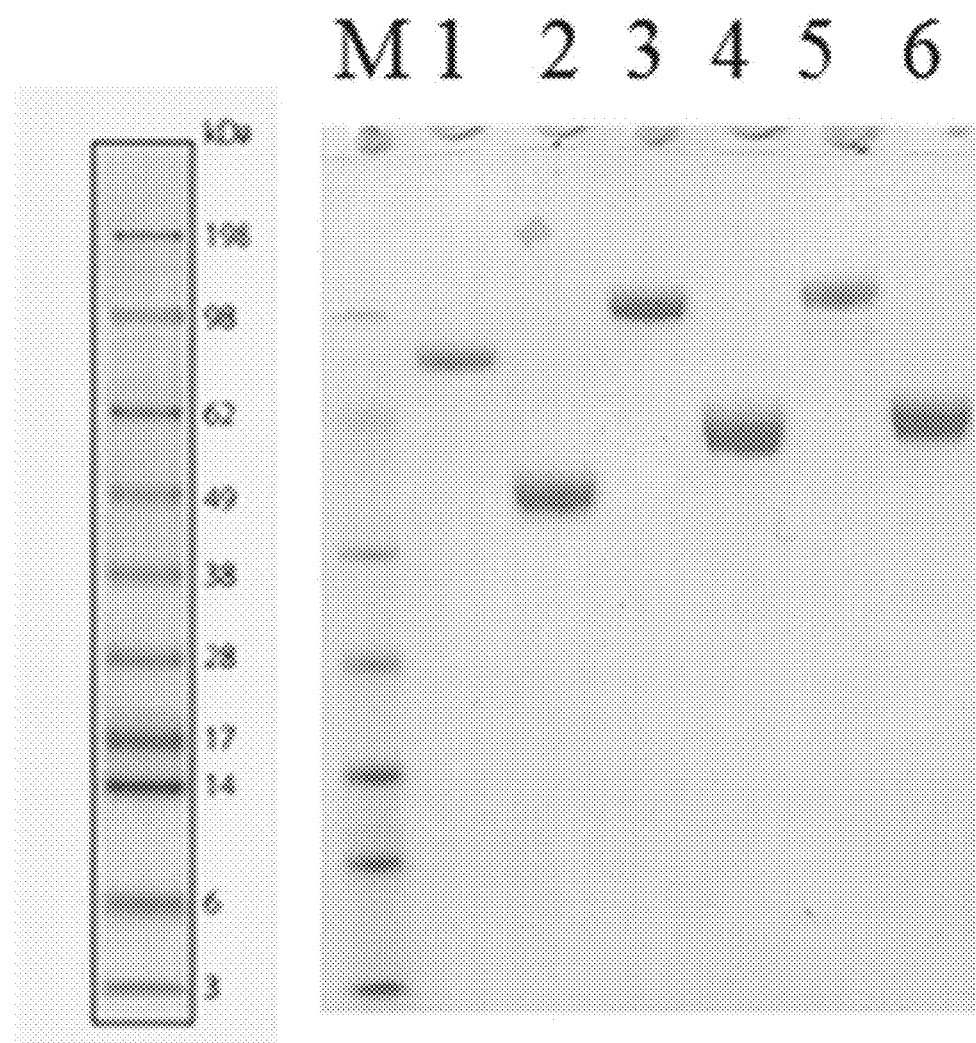
FIG. 2C shows SDS-PAGE gel analysis of the non-reduced and reduced purified bi-functional Fc fusion proteins, respectively: Lane M=marker, Lanes 1 (non-reduced) and 2 (reduced)=Positive Control 2; Lanes 3 (non-reduced) and 4 (reduced)=Fusion Protein 5; Lanes 5 (non-reduced) and 6 (reduced)=Fusion Protein 3.

Coding sequences of Fusion Proteins 1 and 2 having the amino acid sequences of SEQ ID NOs: 38 and 40, respectively, were transfected into and expressed in human embryonic kidney cell line (HEK293F). The secreted fusion proteins were purified from the cell culture supernatant using one-step Protein G chromatography. The proteins were captured by Protein G affinity column (Thermo-Fisher Scientific), eluted with low pH (3.5) buffer, and neutralized with Tris-HCl. As shown in FIGS. 2A-2C greater than 90% purity was achieved using the single step purification method. FIGS. 2A-2C also show that purified Fusion Proteins 1, 2, 3 and 5 have the predicted weight (MW~180 kDa) and properly dimerized when expressed in mammalian cells.

During development, the coding sequence of Fusion Protein 1, SEQ ID NO: 37, was incorporated into an expression vector. The results of competition binding assays of purified Fusion Protein 1 against PDGF and of a PDGF-dependent BALB/3T3 cell growth inhibition assay of Fusion Protein 1 indicate that there is a positional effect on the binding ability of Fusion Protein 1, e.g., it binds PDGF-BB with much lower affinity (see, e.g., Tables 4 and 6).

Therefore, Fusion Protein 2 was constructed by rearranging the orientation of VID and PID. The coding sequence of Fusion Protein 2, SEQ ID NO 39, was incorporated into an expression vector. HEK293F host cells were transfected with the expression vector using a suitable amount of expression vector DNA. A stable clone was selected based on protein expression levels evaluated by an anti-Fc ELISA, and a research cell bank (RCB) was generated from the clone with the optimal levels of fusion protein expression. The Fusion Protein 2 RCB was used for shake flask protein production, and the protein was purified from the culture supernatant using Protein A affinity resin. The protein was buffer-exchanged to phosphate buffer with excipients. The final concentration of the purified Fusion Protein 2 was approximately 20 mg/mL.

Mutagenesis of Fusion Protein 2 was carried out to generate a variant of Fusion Protein 2, i.e., Fusion Protein 3, which comprises a deleted lysine residue (K528) at the C-terminus of IgG1 Fc and a phenylalanine-to-serine (F150S) mutation in the PID of Fusion Protein 2. A 2-step PCR mutagenesis method was used to first delete the lysine and then change the phenylalanine to a serine. The final construct comprises a coding sequence of SEQ ID NO 43. CHO-S host cells were transfected with the expression vector using a suitable amount of expression vector DNA. A first stable clone was selected based on protein expression levels evaluated by an anti-Fc ELISA. This was used to produce Fusion Protein 3 having the amino acid sequence of amino acids 21-769 of SEQ ID NO: 44 (amino acids 1-20 of SEQ ID NO: 44 is a signal peptide sequence that was cleaved off during protein synthesis). Monoclonality issues were detected by FACS, so a round of re-cloning was performed. A second stable clone was selected based on expression levels, and the clone was used to generate a Fusion Protein 4 RCB. The Fusion Protein 4 RCB was used for both shake flask studies and bioreactor production. A vial of Fusion Protein 4 RCB was thawed and expanded in a 1 L shake flask to produce Fusion Protein 4, which has the same amino acid sequence of Fusion Protein 3. Six batches of purified protein were prepared using Protein A affinity resin (one step purification). The protein was buffer-exchanged to histidine buffer with excipients. The final concentration of Fusion Protein 4 was approximately 20 mg/mL.

To obtain a sufficient amount of Fusion Protein 4, a 7 L bioreactor (BR) was run with a final working volume of about 5 L. Platform operation procedures, parameter settings, and control strategies were used, and the medium type and feed schedule were followed. The final product titer was 0.21 g/L.

Purified fusion proteins samples were further processed by clarification, protein A affinity chromatography, a first ultrafiltration step, size exclusion chromatography, a second ultrafiltration step, dialysis, and a third ultrafiltration step to obtain the final product.

To generate Fusion Protein 5, which has the amino acid sequence of amino acids 20-768 of SEQ ID NO: 50 (amino acids 1-19 of SEQ ID NO: 50 is a signal peptide sequence that was cleaved off during protein synthesis), the DNA sequence encoding Fusion Protein 5 was codon-optimizing for expression in CHO cells. The synthesized codon-optimized DNA, with a nucleic acid sequence of SEQ ID NO: 49, was cloned into an expression vector. CHO K1 host cells were seeded at 2×105 cells/mL in CD CHO (Gibco 12490-003) containing 4 mM Glutamine (J. T Baker 2078-06) and 1% HT Supplement (Gibco 11067-030) 72 hours before transfection. The host cells were incubated in an Infors shaker (36.5° C., 75% humidity, 6% CO2, 110 RPM) and counted for cell density before use. A suitable amount of expression plasmid DNA was added into the host cells (1 L or 5 L working volume), and polymer-based transfection reagent was added. The transfected cultures were incubated in an Infors shaker (36.5° C., 75% humidity, 6% CO2, 110 RPM) for 4 hours and a proprietary feed solution was added. The transfected cultures were then incubated in an Infors shaker (32° C., 75% humidity, 6% CO2, 110 RPM). The transfected cultures were harvested on day 10 after transfection. The supernatants were purified for generation of research materials. The purification process included clarification, Protein A affinity chromatography, concentration by Amicon Ultracel, size exclusion chromatography, dialysis by Slide-A-Lyzer, and final concentration by Amicon Ultracel in the formulation buffer.

Fusion Protein 6, having the amino acids 20-766 of SEQ ID NO: 42, was derived from Fusion Protein 5 by deleting the first two amino acids (QG) of Fusion Protein 5, wherein amino acids 1-19 of SEQ ID NO: 42 is a signal peptide sequence that was cleaved off during protein synthesis. The DNA insert was generated by PCR using Fusion Protein 5 expression vector as a template, and the DNA sequence encoding Fusion Protein 6, with a nucleic acid sequence of SEQ ID NO: 41, was cloned into an expression vector. The culturing and purification procedures were the same as for Fusion Protein 5. The final concentration of Fusion Protein 6 was approximately 80 mg/mL in the designated formulation buffer (based on the absorption at 280 nm).

Collectively, these data indicate that fusion proteins having simultaneous anti-VEGF and anti-PDGF activities have been constructed, expressed, purified and characterized.

Example 2: Binding Affinity of the Fusion Proteins to $VEGF_{165}$

A direct binding enzyme-linked immunosorbent assay (ELISA) was used to measure the binding affinity of fusion proteins of the invention to $VEGF_{165}$, a splice variant of VEGF-A. A synthesized VEGF Trap was used as Positive Control 1.

VEGF Trap is a soluble VEGF receptor that was engineered for therapeutic use and is currently approved by FDA to treat AMD. VEGF Trap contains the second Ig-like domain (D2) of VEGFR1 fused to the third Ig-like domain (D3) of VEGFR2 fused to the Fc region of human IgG1 (Holash, J., et al, Proc Natl Acad Sci USA. 2002 Aug. 20; 99(17):11393-8). VEGF Trap targets VEGF-A, VEGF-B, and PlGF.

100 μL of a coating solution (1 μg/mL $VEGF_{165}$ in 1× phosphate buffered saline (PBS), pH 7.2) were added to each well of a 96-well ELISA plate, and the plate was incubated overnight at 4° C. The wells were washed twice with 400 μL of 1×PBS buffer, and excess liquid was carefully removed with a paper towel.

400 μL of a blocking solution (5 g non-fat skim milk in 100 mL 1×PBS) were added to each well, and the plate was incubated at room temperature for 1 hour. The wells were washed twice with 1×PBS buffer.

Fusion protein and control samples were serially diluted three-fold in blocking solution, with a highest protein concentration of 10 mM. 100 μL of the serially diluted samples were added to each well. The plate was covered and incubated on a plate shaker (~100 rpm) for 1 hour at room temperature. The wells were washed three times with wash buffer (1×PBS, 0.05% Tween-20).

100 μL of 1:2500 diluted horseradish peroxidase-conjugated goat anti-human IgG Fc specific antibodies in blocking solution were added to each well. The plates were sealed and incubated on a plate shaker for 1 hour at room temperature. The plates were washed three times with wash buffer.

100 μL of 3,5,3',5'-Tetramethylbenzidine (TMB) were added to each well, and the plates were incubated for 3 to 5 minutes to allow for the reaction to take place. To stop the reaction, 100 μL of stop solution (1N HCl) were added to each well.

The optical density (OD) of each well was determined using an ELISA plate reader at an absorbance wavelength of 450 nm. The absorbance was plotted against the protein concentration of the fusion protein or the control, and the concentration at which the signal was half the maximal effective concentration ($EC_{50}$) was determined.

The binding affinity, expressed as the $EC_{50}$ value, was between 0.22 and 0.93 nM for the tested fusion proteins of the invention. The ELISA results are shown in Table 1.

TABLE 1

| Test Material | $EC_{50}$ (nM) |
|---|---|
| Positive Control 1 | 0.087 |
| Fusion Protein 1 (SEQ ID NO: 38) | 0.220 |
| Fusion Protein 2 (SEQ ID NO: 40) | 0.928 |
| Fusion Protein 3 (aa 21-769 SEQ ID NO: 44) | 0.477 |
| Fusion Protein 4 (aa 21-769 SEQ ID NO: 44) | 0.384 |
| Fusion Protein 5 (aa 20-768 SEQ ID NO: 50) | 0.388 |

Figure 3:
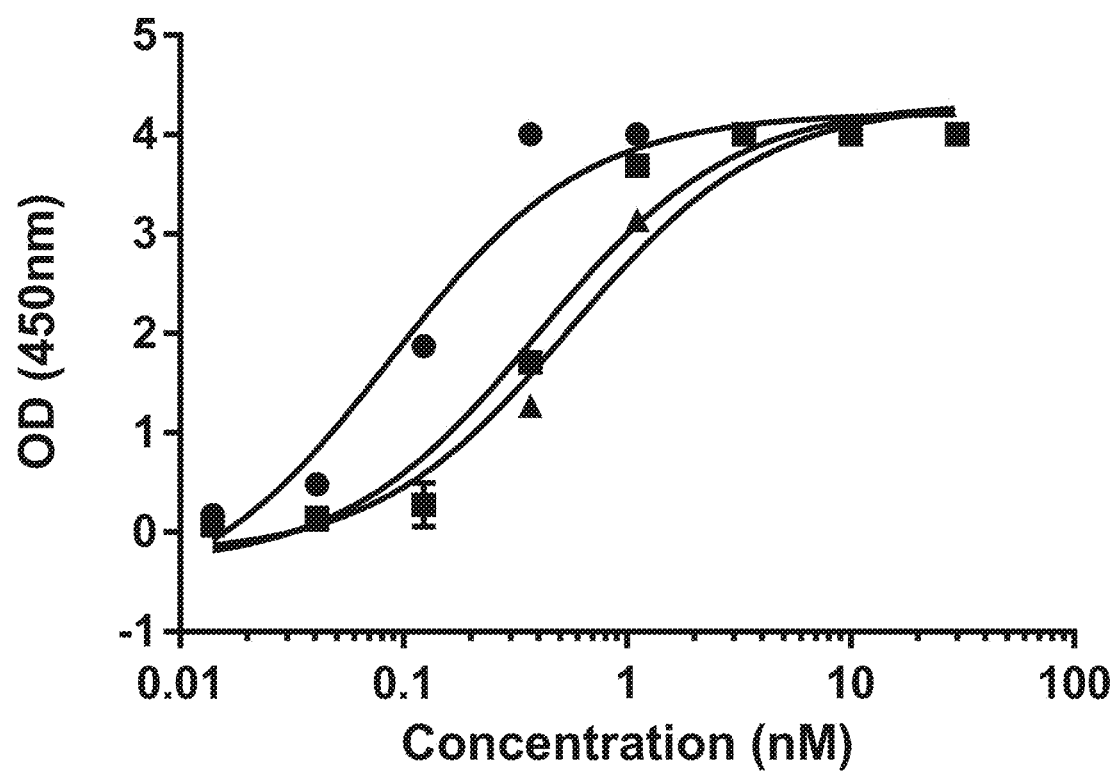
FIG. 3 shows the results of a direct ligand binding assay of three test samples: purified Positive Control 1 (●), Fusion Protein 3 (▲), and Fusion Protein 5 (■) against $VEGF_{165}$. Wells were pre-coated with $VEGF_{165}$ and incubated with various concentrations of test samples; the amount of bound test sample was detected using HRP conjugated goat anti-human IgG1 Fc specific antibody, and the $OD_{450}$ readings were plotted against test sample concentrations.

Results from this Example showed that fusion proteins according to embodiments of the invention, such as Fusion Proteins 1 to 5, bind $VEGF_{165}$ with a high affinity. See also FIG. 3.

Example 3—Binding Affinity of the Fusion Proteins to PDGF

A direct binding ELISA was used to measure the binding affinity of fusion proteins of the invention to PDGF. A synthesized PDGF Trap was used as Positive Control 2.

PDGF Trap is a soluble PDGF receptor that was engineered for use as a positive control. PDGF Trap contains the second Ig-like domain (D1 to D3) of PDGFRβ fused to the Fc region of human IgG1. (Lu et al. Am J Obstet Gynecol., 2008, 198(4): 477.e1-e10). PDGF Trap targets PDGF-BB, PDGF-DD, and PDGF-AB.

100 μL of a coating solution (1 μg/mL PDGF-BB in 1× phosphate buffered saline (PBS), pH 7.2) were added to each well of a 96-well ELISA plate, and the plate was incubated overnight at 4° C. The wells were washed twice with 400 μL of 1×PBS buffer, and excess liquid was carefully removed with a paper towel.

400 μL of a blocking solution (1 g bovine serum albumin in 100 mL of 1×PBS) were added to each well, and the plate was incubated at room temperature for 1 hour. The wells were washed twice with 1×PBS buffer.

Fusion protein and control samples were serially diluted three-fold in blocking solution, with a highest protein concentration of 10 mM. 100 μL of the serially diluted samples were added to each well. The plate was covered and incubated on a plate shaker (~100 rpm) for 1 hour at room temperature. The wells were washed three times with wash buffer (1×PBS, 0.05% Tween-20).

100 μL of 1:2500 diluted horseradish peroxidase-conjugated goat anti-human IgG Fc specific antibodies in blocking solution were added to each well. The plates were sealed and incubated on a plate shaker for 1 hour at room temperature. The plates were washed three times with wash buffer.

100 μL of 3,5,3',5'-Tetramethylbenzidine (TMB) were added to each well, and the plates were incubated for 3 to 5 minutes to allow for the reaction to take place. To stop the reaction, 100 μL of stop solution (1N HCl) were added to each well.

The optical density (OD) of each well was determined using an ELISA plate reader at an absorbance wavelength of 450 nm. The absorbance was plotted against the protein concentration of the fusion protein or the control, and the concentration of the fusion protein at which the signal was half the maximal effective concentration ($EC_{50}$) was determined.

The binding affinity, expressed as the $EC_{50}$ value, was approximately 0.16 to 2.5 nM for the tested fusion proteins of the invention. The ELISA results are shown in Table 2.

TABLE 2

| Test Material | $EC_{50}$ (nM) |
|---|---|
| Positive Control 2 | 1.354 |
| Fusion Protein 1 | 0.160 |
| Fusion Protein 2 | 0.939 |
| Fusion Protein 3 | 2.285 |
| Fusion Protein 4 | 2.538 |
| Fusion Protein 5 | 2.286 |

Figure 4:
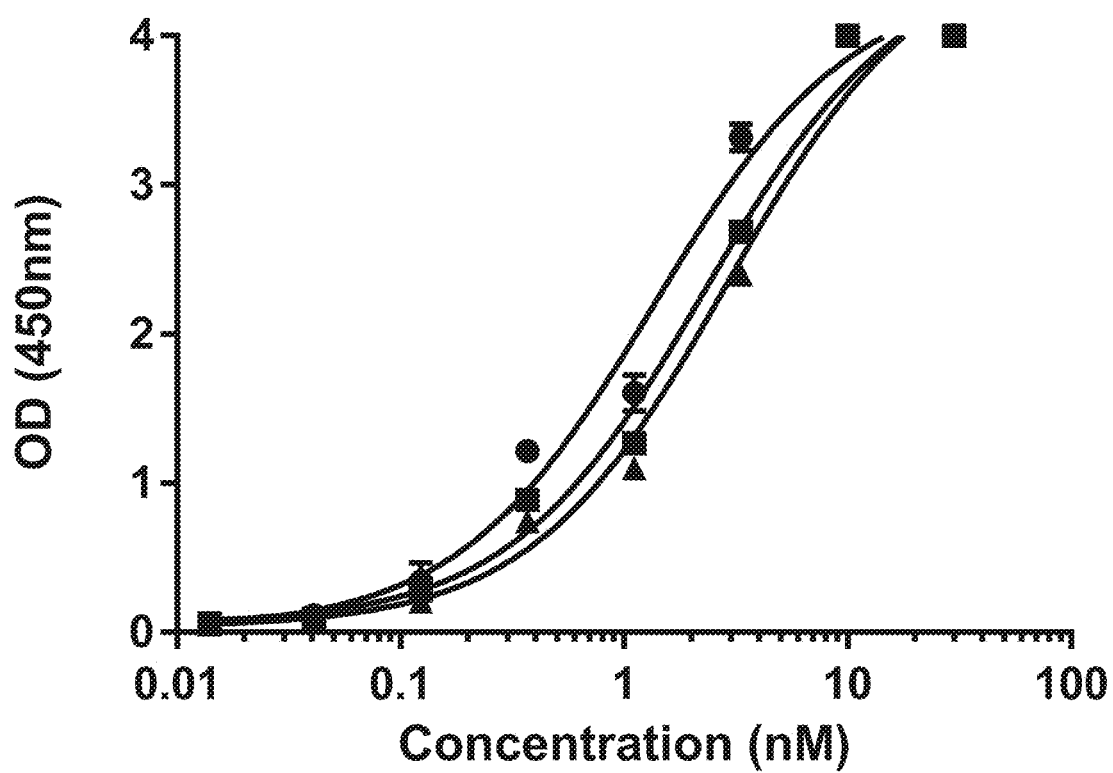
FIG. 4 shows the results of a direct ligand binding assay of three test samples: purified Positive Control 2 (●), Fusion Protein 3 (▲), and Fusion Protein 5 (■) against PDGF-BB. Wells were pre-coated with PDGF-BB and incubated with various concentrations of test sample; the amount of test sample was detected using HRP conjugated goat anti-human IgG1 Fc specific antibody, and the $OD_{450}$ readings were plotted against test sample concentrations.

Results from this Example showed that fusion proteins of the invention, e.g., Fusion Proteins 1 to 5, bind PDGF with a high affinity. See also FIG. 4.

Example 4—Competitive Binding of the Fusion Proteins to $VEGF_{165}$

A competitive binding assay was used to assess the binding affinity of fusion proteins of the invention to $VEGF_{165}$. A synthesized VEGF Trap was used as Positive Control 1.

Fusion protein and control samples were serially diluted three-fold in blocking solution, with a highest protein concentration of 10 mM. Equal volumes of the diluted samples were incubated with 10 pM of $VEGF_{165}$ for a final concentration of 5 pM VEGF-A (R&D System) overnight at room temperature.

50 μL of assay diluent from the Quantikine ELISA Human VEGF kit (R&D Systems, Inc.) were added to each well of a 96-well plate. 200 μL of the standards, controls, or fusion proteins were added to the appropriate wells in duplicate. The plates were sealed and incubated for 2 hours at room temperature and then washed three times with wash buffer.

200 μL of $VEGF_{165}$ conjugate provided in the kit was added to each well, and the plates were sealed and incubated for 2 hours at room temperature. The plates were washed three times.

200 μL of substrate solution provided in the kit were added to each well, and the plates were sealed and incubated for 20 minutes at room temperature. To stop the reaction, 50 µL of stop solution provided in the kit were added to each well.

The OD of each well was determined using an ELISA plate reader at an absorbance wavelength of 450 nm and 540 nm (or 570 nm). The concentration of unbound $VEGF_{165}$ (free $VEGF_{165}$) was plotted against the protein concentration of the fusion protein or the control, and the concentration of the fusion protein at which the signal from the free $VEGF_{165}$ was reduced by 50% ($IC_{50}$) was determined.

The $IC_{50}$ value of the fusion protein of the invention was determined to be approximately 3.78 to 4.67 pM. The results of the competitive binding assay are shown in Table 3.

TABLE 3

| Test Material | $IC_{50}$ (pM) |
| --- | --- |
| Positive Control 1 | 5.173 |
| Fusion Protein 1 | 4.670 |
| Fusion Protein 2 | 3.780 |
| Fusion Protein 3 | 3.775 |

Figure 5A:
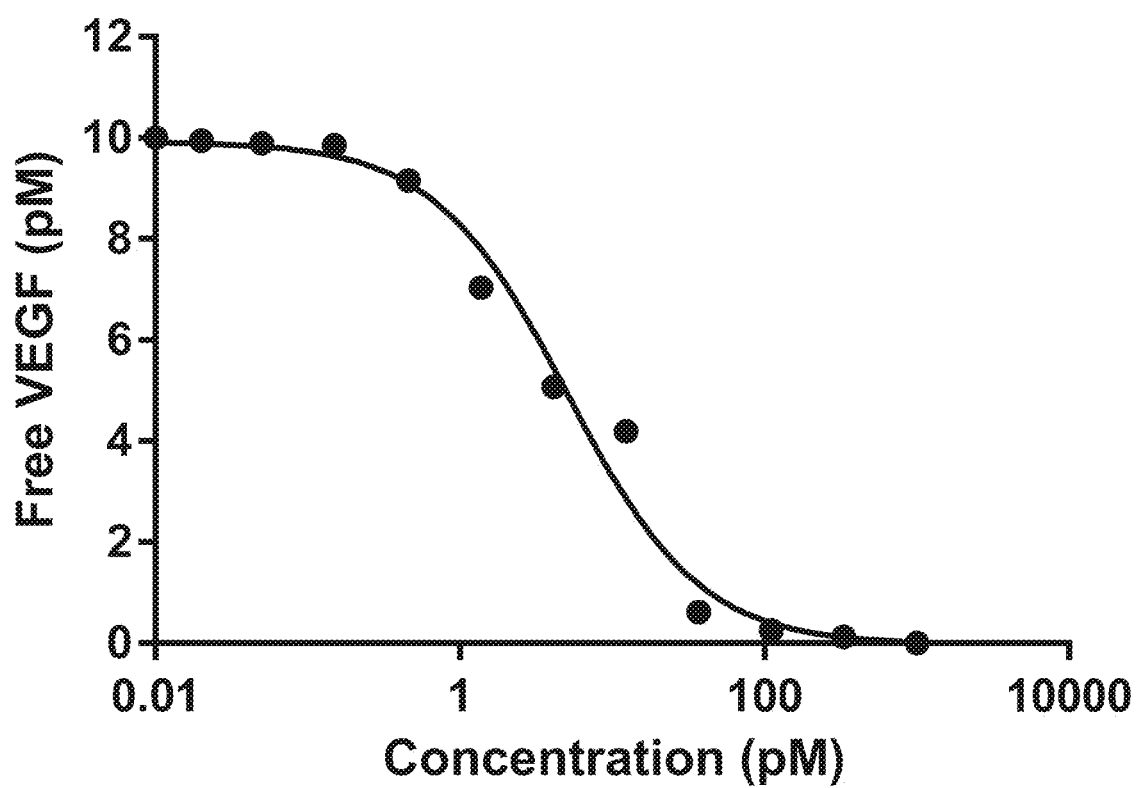
FIG. 5A and FIG. 5B show the affinity assessment of Fusion Protein 1 against $VEGF_{165}$ and PDGF-BB in solution, respectively, in a competitive binding assay. Various concentrations of Fusion Protein 1 were incubated overnight in solution with a fixed concentration of either $VEGF_{165}$ or PDGF-BB, the concentrations of free $VEGF_{165}$ or PDGF-BB were determined using a quantitative sandwich enzyme-linked immunoassay (ELISA) assay, and plotted against Fusion Protein 1 concentrations.
Figure 6A:
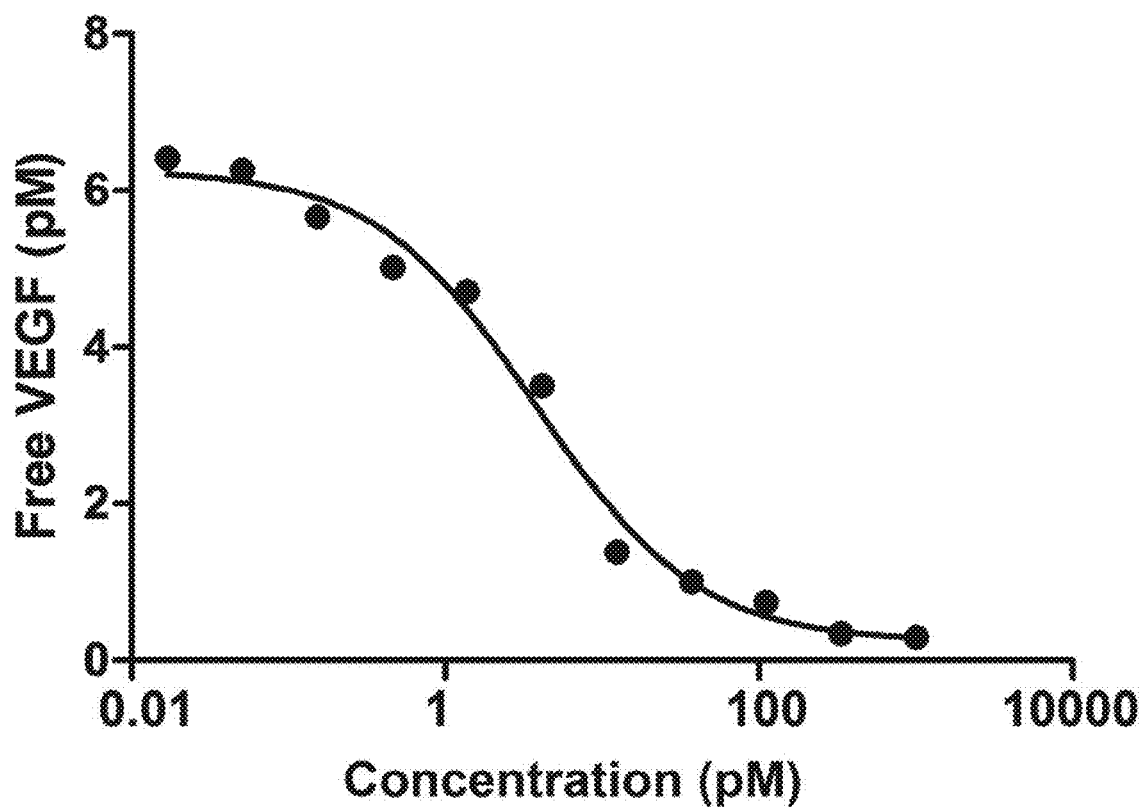
FIG. 6A and FIG. 6B show the affinity assessment of Fusion Protein 2 against $VEGF_{165}$ and PDGF-BB in solution, respectively, in a competitive binding assay. Various concentrations of Fusion Protein 2 were incubated overnight in solution with a fixed concentration of either $VEGF_{165}$ or PDGF-BB; the concentrations of free $VEGF_{165}$ or PDGF-BB were determined using a quantitative sandwich ELISA assay and plotted against Fusion Protein 2 concentrations.

Results from this Example confirmed that fusion proteins of the invention, e.g., Fusion Proteins 1, 2 and 3, bind $VEGF_{165}$ with a high affinity. See also FIGS. 5A and 6A.

Example 5—Competitive Binding of the Fusion Proteins to PDGF-BB

A competitive binding assay was used to assess the binding affinity of fusion proteins of the invention to PDGF-BB. A synthesized PDGF Trap was used as Positive Control 2.

Fusion protein and control samples were serially diluted three-fold in blocking solution, with a highest protein concentration of 10 mM. Equal volumes of the diluted samples were incubated with 20 pM of PDGF-BB for a final concentration of 10 pM overnight at room temperature.

100 µL of assay diluent from the Quantikine ELISA Human PDGF-BB kit were added to each well of a 96-well plate. 100 µL of the standards, controls, or fusion proteins were added to the appropriate wells in duplicate. The plates were sealed and incubated for 2 hours at room temperature and then washed four times with wash buffer.

200 µL of PDGF-BB conjugate provided in the kit were added to each well, and the plates were sealed and incubated for 1.5 hours at room temperature. The plates were washed four times.

200 µL of substrate solution provided in the kit were added to each well, and the plates were sealed and incubated for 20 minutes at room temperature. To stop the reaction, 50 µL of stop solution provided in the kit were added to each well.

The OD of each well was determined using an ELISA plate reader at an absorbance wavelength of 450 nm and 540 nm (or 570 nm). Free PDGF-BB was plotted against the protein concentration of the fusion protein or the control, and the concentration of the fusion protein at which the signal from the free PDGF-BB was reduced by 50% ($IC_{50}$) was determined.

The $IC_{50}$ value of the fusion protein of the invention was determined to be approximately 0.125-200 nM. The results of the competitive binding assay are shown in Table 4.

TABLE 4

| Test Material | $IC_{50}$ (nM) |
| --- | --- |
| Positive Control 2 | 1.015 |
| Fusion Protein 1 | 200 |
| Fusion Protein 2 | 0.125 |
| Fusion Protein 3 | 1.371 |

Figure 5B:
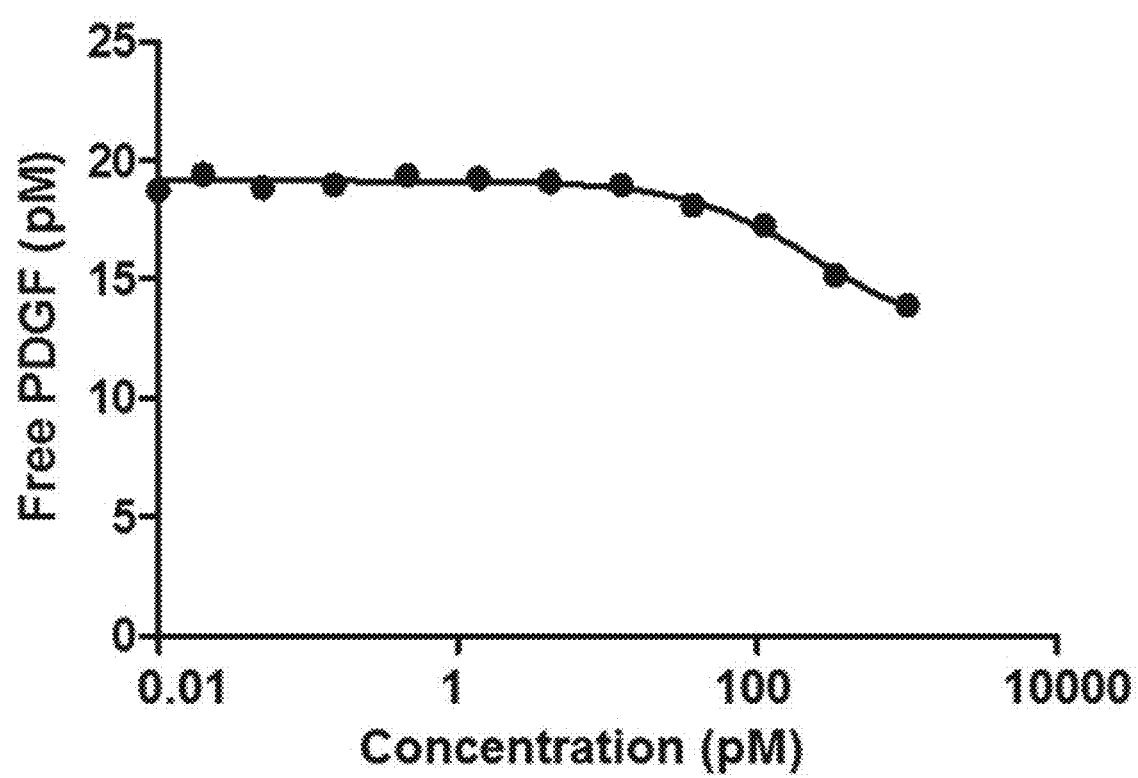
Figure 6B:
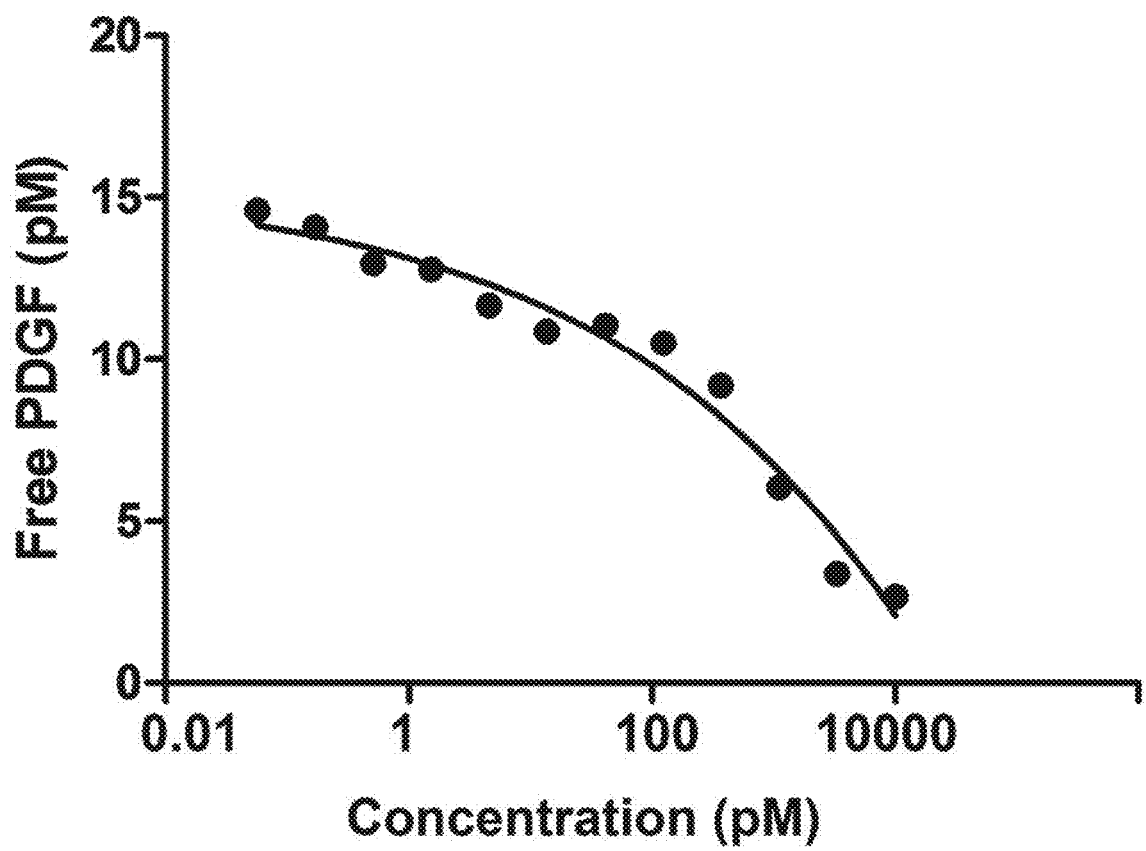

Results from this Example confirmed that fusion proteins of the invention, e.g., Fusion Proteins 2 and 3, bind PDGF with a high affinity. See also FIGS. 5B and 6B.

Example 6—Inhibition of HUVEC Proliferation by the Fusion Proteins

A human umbilical vein endothelial cell (HUVEC) proliferation assay was carried out to test the functionality of the fusion proteins of the invention. A synthesized VEGF Trap was used as Positive Control 1.

100 µL of a coating solution (1% gelatin in double distilled water) were added to each well of a 96-well ELISA plate, and the plate was incubated for 2 hours or overnight at 37° C. The wells were washed twice with 1×PBS buffer.

3500 counts of human umbilical vein endothelial cells in endothelial cell growth medium were added to each well, and the plate was incubated overnight at 37° C.

Fusion protein samples were diluted in assay buffer (Medium-199 1× Earle's Salts, 10% fetal bovine serum, 10 mM HEPES, 1× antibiotic/antimycotic), with a highest protein concentration of 300 nM. The fusion protein samples were mixed with $VEGF_{165}$ (8 ng/mL), and the mixtures were incubated overnight at room temperature. The wells were then washed with 200 µL of 1×PBS.

100 µL of the $VEGF_{165}$/sample mixture were added to each well, and the plates were incubated for 72 hours at 37° C. with 5% $CO_2$. Following incubation, 10 µL MTS detection reagent (3-(4,5-dimethylthiazol-2-yl)-5-(3-carboxymethoxyphenyl)-2-(4-sulfophenyl)-2H-tetrazolium)+ phenazine methosulfate in distilled PBS) were added to each well, and the plates were incubated at 37° C. for 2.5 hours.

The OD of each well was determined using an ELISA plate reader at an absorbance wavelength of 490 nm. The absorbance was plotted against the protein concentration of the fusion protein or the control, and the concentration at which the cell proliferation was inhibited by 50% ($IC_{50}$) was determined.

The inhibition of cell proliferation ($IC_{50}$) was determined to be between 0.058 and 0.285 nM for the tested fusion proteins of the invention. The results of the proliferation assay are shown in Table 5.

TABLE 5

| Test Material | $IC_{50}$ (nM) |
| --- | --- |
| Positive Control 1 | 0.068 |
| Fusion Protein 1 | 0.058 |
| Fusion Protein 2 | 0.202 |
| Fusion Protein 3 | 0.153 |
| Fusion Protein 4 | 0.285 |
| Fusion Protein 5 | 0.112 |

Figure 7:
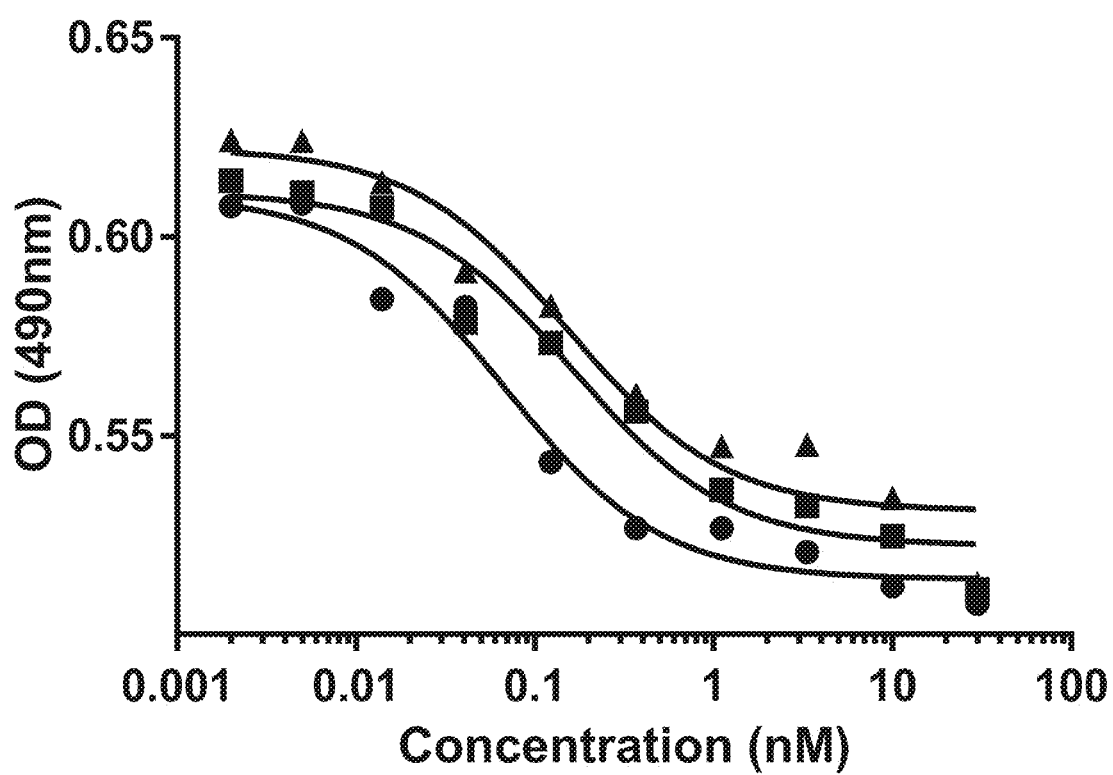
FIG. 7 shows the inhibitory effect of Positive Control 1 (●), Fusion Protein 3 (▲), and Fusion Protein 5 (■) on the VEGF-dependent growth of HUVEC cells. $OD_{490}$ readings were plotted against test sample concentrations.

Results from this Example showed that fusion proteins of the invention, e.g., Fusion Proteins 1 to 5, inhibited VEGF-dependent growth of HUVEC cells. See also FIG. 7.

Example 7—Inhibition of BALB/3T3 Proliferation by the Fusion Proteins

A cell proliferation assay using 3T3 fibroblasts derived from BALB mice was carried out to test the functionality of the fusion proteins of the invention. A synthesized PDGF Trap was used as Positive Control 2.

4000 counts of mouse 3T3 fibroblast cells in DMEM (1 mM sodium pyruvate, 4 mM L-glutamine, 10% bovine serum albumin, 1× antibiotic/antimycotic) were added to each well, and the plate was incubated overnight at 37° C.

Fusion protein samples were diluted in assay buffer (1 mM sodium pyruvate, 4 mM L-glutamine, 0.5% bovine serum albumin, 1× antibiotic/antimycotic), with a highest protein concentration of 300 nM. The fusion protein samples were mixed with PDGF (8 ng/mL), and the mixtures were incubated overnight at room temperature. The wells were then washed with 200 μL of 1×PBS.

Cells were starved with assay buffer at 37° C. with 5% $CO_2$ for 4 hours. 100 μL of the PDGF/sample mixture were added to each well, and the plates were incubated for 72 hours at 37° C. with 5% $CO_2$. Following incubation, 10 μL MTS detection reagent were added to each well, and the plates were incubated at 37° C. for 2.5 hours.

The OD of each well was determined using an ELISA plate reader at an absorbance wavelength of 490 nm. The absorbance was plotted against the protein concentration of the fusion protein or the control, and the concentration at which the cell proliferation was inhibited by 50% ($IC_{50}$) was determined.

The $IC_{50}$ was calculated determined to be between 0.45 and 1000 nM for the tested fusion proteins of the invention. The results of the proliferation assay are shown in Table 6.

TABLE 6

| Test Material | $IC_{50}$ (nM) |
| --- | --- |
| Positive Control 2 | 0.260 |
| Fusion Protein 1 | 1000 |
| Fusion Protein 2 | 0.669 |
| Fusion Protein 3 | 0.1992 |
| Fusion Protein 4 | 0.708 |
| Fusion Protein 5 | 0.275 |

Figure 8:
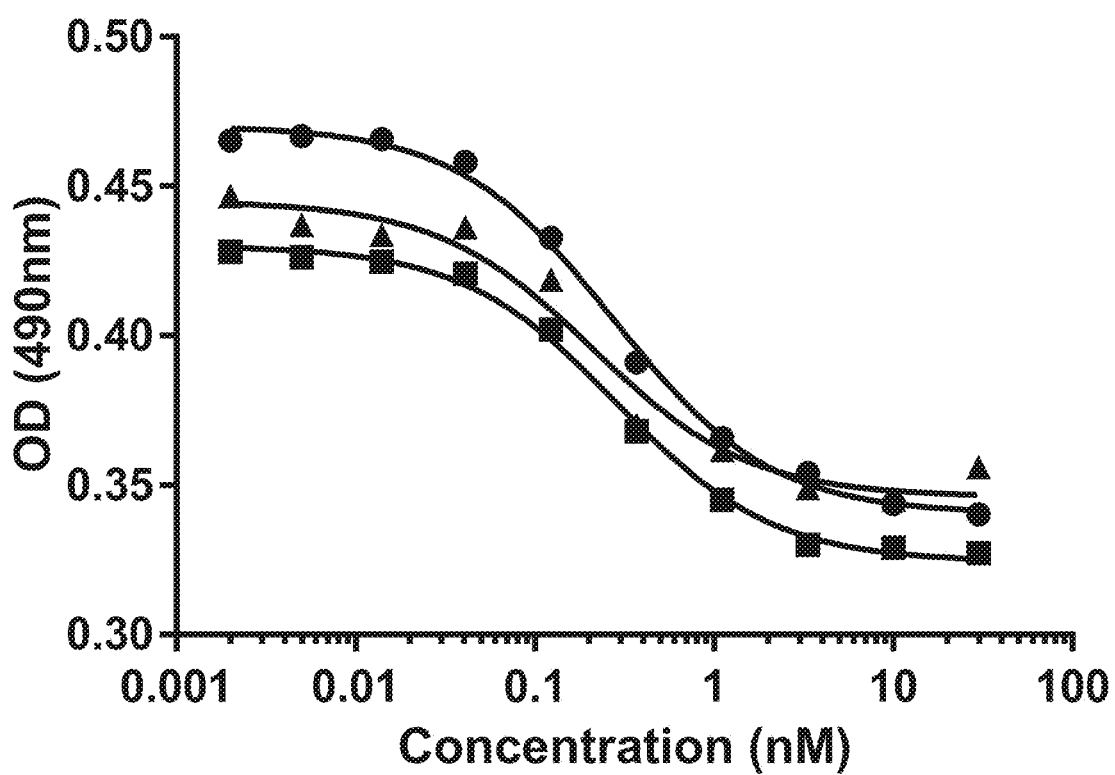
FIG. 8 shows the inhibitory effect of Positive Control 2 (●), Fusion Protein 3 (▲), and Fusion Protein 5 (■) on the PDGF-dependent growth of BALB/3T3 cells; $OD_{490}$ readings were plotted against test sample concentrations.

Results from this Example showed that fusions of the invention, e.g., Fusion Proteins 1 to 5, inhibited PDGF-dependent growth of BALB/3T3 cells. See also FIG. 8.

Example 8—Inhibition of VEGF-Induced Leakage in Dutch Belted Rabbits by the Fusion Proteins Fusion proteins of the invention were tested in an in vivo model of retinal neovascularization to determine their efficacy in preventing vascular leakage. In this model, VEGF is intravitreally injected to the vitreous of rabbit eyes to induce uncontrolled neovascularization of the retina and subsequent leakage. Avastin®, a recombinant humanized monoclonal antibody that blocks angiogenesis by inhibiting VEGF-A, and Eylea, a recombinant fusion protein consisting of portions of human VEGFR1 and VEGFR2 fused to the Fc portion of human IgG1, were used as Positive Controls 3 and 4.

Dutch Belted rabbits were anesthetized using isoflurane (3-5%), and their eyes were treated with ophthalmic Betadine solution. The rabbits' eyes were then washed with sterile saline, and lidocaine hydrochloride (2% injectable) or proparacaine (0.5%) was applied to the ocular surface.

On Day 1, Dutch Belted rabbits were intravitreally injected with fusion proteins of the invention, vehicle (negative) control, or reference (positive) controls at predetermined doses using a BD 300 μL insulin syringe (31 ga×5/16 inch). The needle was inserted through the dorsotemporal quadrant of the eye, approximately 3-4 mm poseterior to the limb and 3-4 mm lateral to the dorsal rectus muscles, and 50 μL of solution was delivered. On Day 3, $VEGF_{165}$ was injected into the same eyes.

Fluorescein angiograms (FAs) were conducted on all dosage groups 3 days after VEGF-induction (Day 6) to assess leakiness and tortuosity using a scale from 0 (normal) to 4 (severe).

Signs of ocular irritation were scored using the Draize scoring system prior to fusion protein dosing, prior to VEGF induction, and prior to FA assessments. According to the Draize analysis, all of the rabbit eyes were normal prior to the initiation of dosing, and no drug-related findings were evident during the course of the study. The findings that were scored using the Draize system were transient and observed in all of the dose groups, and were thus likely due to the procedure associated with the intravitreal dose administration.

FAs associated with the vehicle control group had the highest mean score (2.58) associated with retinal vasculature leakiness and tortuosity. The two reference positive control groups had mean scores of 0.25 and 0, indicating a significant reduction in retinal vasculature leakiness and tortuosity. The tested fusion proteins of the invention had a mean score of 0.167, showing effectiveness in reducing VEGF-induced retinal leakiness and tortuosity comparable to the positive controls. The results of the in vivo assay are shown in Table 7.

TABLE 7

| Test Material | Dose (μg) | No. of Scores | Day 6 Mean Leakage Score |
| --- | --- | --- | --- |
| Vehicle | 0 | 12 | 2.583 |
| Positive Control 3 (Avastin ®) | 1250 | 12 | 0.250 |
| Positive Control 4 (Eylea ®) | 625 | 12 | 0 |
| Fusion Protein 4 | 1000 | 12 | 0.167 |
| Fusion Protein 5 | 1000 | 12 | 0.167 |

Example 9—Dose-Response Inhibition of VEGF-Induced Leakage in Dutch Belted Rabbits by the Fusion Proteins Fusion proteins of the invention were tested in an in vivo model of retinal neovascularization at varying doses to determine their dose-response effectiveness in preventing vascular leakage. In this model, $VEGF_{165}$ is intravitreally injected to the vitreous of rabbit eyes to induce uncontrolled neovascularization of the retina and subsequent leakage.

On Day 1, Dutch Belted rabbits were intravitreally injected with Fusion Protein 5 according to an embodiment of the invention at various doses, vehicle (negative) control, or reference (positive) controls. VEGF-induction was carried out on day 3.

FAs were conducted on all dosage groups 3 days after the VEGF-induction (Day 6) to assess leakiness and tortuosity using a scale from 0 (normal) to 4 (severe).

Signs of ocular irritation were noted using the Draize scoring system prior to fusion protein dosing, prior to VEGF-induction, and prior to FA assessments. According to the Draize analysis, all of the rabbit eyes were normal prior to the initiation of dosing, and no drug-related findings were evident during the course of the study. The findings that were scored using the Draize system were transient and observed in all of the dose groups, and were thus likely due to the procedure associated with the intravitreal dose administration.

For the first VEGF-induction, FAs associated with vehicle control group had the highest mean score (3.4) associated with retinal vasculature leakiness and tortuosity. The two reference positive control groups had mean scores of 0, indicating a significant reduction in retinal vasculature leakiness and tortuosity. The tested fusion protein of the invention (Fusion Protein 5) had scores of 0.08, 0.42, and 0.17 at doses of 100, 500 and 1000 µg, respectively, showing effectiveness in reducing VEGF-induced retinal leakiness and tortuosity comparable to the positive controls.

The results of the dose-response in vitro assay are shown in Table 8.

TABLE 8

| Test Material | Dose (µg) | No. of Scores | Day 6 Mean Leakage Score |
|---|---|---|---|
| Vehicle | 0 | 12 | 3.400 |
| Positive Control 3 (Avastin ®) | 1250 | 10 | 0 |
| Positive Control 4 (Eylea ®) | 625 | 12 | 0 |
| Fusion Protein 5 | 1000 | 12 | 0.167 |
| Fusion Protein 5 | 500 | 12 | 0.417 |
| Fusion Protein 5 | 100 | 12 | 0.083 |

Example 10—Reduction of Lesion Size in Laser-Induced Choroidal Neovascularization (CNV) in Rats by the Fusion Proteins The eyes of Brown Norway will be dilated with a 1% Cyclogyl solution and protected from light. Following dilation, the rats will be anesthetized using a ketamine and xylazine mixture. Three lesion burns will be introduced to the retina of each eye using a laser at 532 nm on Day 1.

On Day 3, the animals will be anesthetized with a ketamine and xylazine mixture, their eyes will be dilated, and 5 µL of fusion proteins according to embodiments of the invention, vehicle (negative) control, or reference (positive) controls at predetermined doses will be intravitreally injected into both eyes of an animal using a Hamilton syringe with 33 gauge needle.

On Day 22, the animals will receive an IP injection of 10% fluorescein sodium at 1 µL/g of body weight. Fundus images will be taken prior to lesion introduction, after lesion burns to confirm successful lesions, and on Day 22 using a Micron III small animal funduscope (Phoenix Research). Lesion size will be determined and compared across dosage groups.

Example 11—Reduction of Lesion Size in Laser-induced CNV in Monkeys by the Fusion Proteins A laser-induced CNV model will be established in monkeys. Six to nine burns will be introduced around the macula of each eye using 532 nm diode laser photocoagulation, and 0.5 mg of fusion proteins of the invention will be intravitreally injected on the same day.

The animals will be sedated with intravenous 2.5% soluble pentobarbitone (1 mL/kg) 20 days later. The eyelids will be fixed to keep the eyes open, and color photographs will be taken using a fundus camera.

Fluorescein dye (20% fluorescein sodium; 0.05 mL/kg) will then be injected into a vein of a lower extremity. Photographs will be taken at several time points after injection of the dye, including the arterial phase, early arteriovenous phase, and several late arteriovenous phases, to monitor leakage of fluorescein associated with CNV lesions.

Example 12—Inhibition of Human Tumor Growth in Xenograft Mice by the Fusion Proteins Various human cancer cells, such as human hepatocellular carcinoma Hep3B cells (ATCC #HB-8064) and human colorectal cancer LoVo cells (ATCC #CCL-229), can be used to establish xenograft models in nude mice.

In order to assess the inhibitory effects of the fusion proteins of the invention on the tumor growth, tumor cells will be implanted into nude mice, and various concentrations of fusion proteins according to embodiments of the invention, ranging from 0.1 to 10 mg/kg, will be administered to the mice intravenously twice weekly. The tumor growth will be measured weekly for up to 7 weeks.

Example 13—Pharmacokinetic Assessment of the Fusion Proteins in Rats and Monkeys The pharmacokinetics of the fusion proteins of the invention will be assessed in animals. A range of 10 to 300 mg/kg fusion proteins according to embodiments of the invention will be administered to rats or monkeys via subcutaneous injection or intravenous injection. Blood samples will be obtained at different time points after the injection for up to 15 days. The concentrations of the fusion proteins in the blood samples will be determined using an ELISA method, and pharmacokinetic parameters will be calculated.

Example 14—Ocular Pharmacokinetic Assessment of the Fusion Proteins in Rabbits and Monkeys The pharmacokinetics of the fusion proteins of the invention will be assessed in animals. A range of 0.1 to 4 mg per eye of fusion proteins according to embodiments of the invention will be administered to rabbits or monkeys via intravitreal injection. Ocular tissues and blood samples will be obtained at different time points after the injection for up to 28 days. The concentrations of the fusion proteins in the ocular tissues and blood samples will be determined using an ELISA method, and pharmacokinetic parameters will be calculated.

While the invention has been described in detail, and with reference to specific embodiments thereof, it will be apparent to one of ordinary skill in the art that various changes and modifications can be made therein without departing from the spirit and scope of the invention.

We claim:

1. A fusion protein consisting of:
    a. a first peptide consisting of an Ig-like domain D2 of a VEGFR1 and an Ig-like domain D3 of a VEGFR2,
    b. an Fc region of an antibody consisting of a CH2 and a CH3 region of IgG1,
    c. a second peptide consisting of Ig-like domains D1 to D3 of a PDGFRβ, and
    d. a linker peptide;
wherein the fusion protein is arranged from N-terminus to C-terminus in an order selected from (a)-(b)-(d)-(c) or (c)-(b)-(d)-(a); and
wherein the fusion protein is capable of binding to a VEGF and a PDGF and inhibiting the activity of the VEGF and the activity of the PDGF.

2. The fusion protein of claim 1, wherein:
    a. the Ig-like domain D2 of the VEGFR1 and the Ig-like domain D3 of the VEGFR2 consists of an amino acid sequence having at least 90% identity to SEQ ID NO: 7;
    b. the Fc region of the antibody consists of an amino acid sequence having at least 90% identity to SEQ ID NO: 12; and
    c. the Ig-like domains D1 to D3 of the PDGFRβ consists of an amino acid sequence having at least 90% identity to SEQ ID NO: 2.

3. The fusion protein of claim 2, wherein:
    a. the Ig-like domain D2 of the VEGFR1 and the Ig-like domain D3 of the VEGFR2 consists of an amino acid sequence selected from the group consisting of SEQ ID NOs: 7 and 10;
    b. the Fc region of the antibody consists of an amino acid sequence selected from the group consisting of SEQ ID NOs: 12 and 15; and
    c. the Ig-like domains D1 to D3 of the PDGFRβ consists of an amino acid sequence selected from the group consisting of SEQ ID NOs: 2 and 5.

4. The fusion protein of claim 1, wherein the linker peptide consists of the amino acid sequence of SEQ ID NO: 20 or 24.

5. A fusion protein consisting of an amino acid sequence selected from the group consisting of SEQ ID NO: 38, SEQ ID NO: 40, amino acids 20-766 of SEQ ID NO: 42, amino acids 21-769 of SEQ ID NO: 44 and amino acids 20-768 of SEQ ID NO: 50.

6. The fusion protein of claim 5, consisting of an amino acid sequence selected from amino acids 21-769 of SEQ ID NO: 44 or amino acids 20-768 of SEQ ID NO: 50.

7. An isolated nucleic acid molecule encoding the fusion protein of claim 1.

8. A host cell comprising a nucleic acid molecule encoding the fusion protein of claim 1.

9. A method of producing the fusion protein of claim 1, comprising:
    a. culturing a host cell comprising a nucleic acid molecule encoding the fusion protein of claim 1, under a condition that the fusion protein is produced; and
    b. recovering the fusion protein produced by the host cell.

10. A pharmaceutical composition comprising the fusion protein of claim 1 and a pharmaceutically acceptable carrier.

11. A method of inhibiting the activity of at least one of a VEGFR and a PDGFR in a subject in need thereof, comprising administering to a subject in need thereof an effective amount of the fusion protein of claim 1.

12. The method of claim 11, wherein the subject is in need of a treatment of an ocular neovascular disorder selected from the group consisting of choroidal neovascularization (CNV), wet age-related macular degeneration, geographic atrophy, and diabetic retinopathy.

13. A pharmaceutical composition comprising the fusion protein of claim 6, wherein the fusion protein consists of amino acids 21-769 of SEQ ID NO: 44.

14. A method of inhibiting the activity of at least one of a VEGFR and a PDGFR in a subject in need thereof, comprising administering to the subject an effective amount of the pharmaceutical composition of claim 13.

15. The method of claim 14, wherein the subject is in need of a treatment of an ocular neovascular disorder selected from the group consisting of choroidal neovascularization (CNV), wet age-related macular degeneration, geographic atrophy, and diabetic retinopathy.

16. A pharmaceutical composition comprising the fusion protein of claim 6, wherein the fusion protein consists of amino acids 20-768 of SEQ ID NO: 50.

17. A method of inhibiting the activity of at least one of a VEGFR and a PDGFR in a subject in need thereof, comprising administering to the subject an effective amount of the pharmaceutical composition of claim 16.

18. The method of claim 17, wherein the subject is in need of a treatment of an ocular neovascular disorder selected from the group consisting of choroidal neovascularization (CNV), wet age-related macular degeneration, geographic atrophy, and diabetic retinopathy.

* * * * *